US006368791B1

(12) United States Patent
Felix et al.

(10) Patent No.: US 6,368,791 B1
(45) Date of Patent: Apr. 9, 2002

(54) METHODS AND KITS FOR ANALYSIS OF CHROMOSOMAL REARRANGEMENTS ASSOCIATED WITH LEUKEMIA

(75) Inventors: Carolyn A. Felix, Ardmore, PA (US); Douglas H. Jones, Iowa City, IA (US); Eric Rappaport, Blackwood, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/026,033

(22) Filed: Feb. 19, 1998

Related U.S. Application Data

(60) Provisional application No. 60/038,624, filed on Feb. 19, 1997, provisional application No. 60/056,938, filed on Aug. 25, 1997, and provisional application No. 60/065,911, filed on Nov. 17, 1997.

(51) Int. Cl.[7] ............................. C12Q 1/68; C12P 19/34
(52) U.S. Cl. ......................... 435/6; 435/91.1; 435/91.2
(58) Field of Search .................. 435/6, 91.2; 536/23.1, 536/24.3

(56) References Cited

U.S. PATENT DOCUMENTS 5,411,875 A    5/1995    Jones

OTHER PUBLICATIONS

Amersham Life Sciences Catalog, p. 85, 1995.*
Bernard et al., 1994, Oncogene 9:1039–1045.
Borkhardt et al., 1997, Oncogene 14:195–202.
Broeker et al., 1996, Blood 87:1912–1922.
Caligiuri et al., 1996, Cancer Res. 56:1418–1425.
Chaplin et al., 1995, Blood 85:1435–1441.
Chaplin et al., 1995, Blood 86:2073–2076.
Chen et al., 1984, J. Biol. Chem. 259:13560–13566.
Chen et al., 1994, Annu. Rev. Pharmacol. Toxicol. 84:191–218.
Chen et al., 1993, Blood 81:2386–2393.
Cimino et al., 1993, Blood 82:544–546.
Corbett et al., 1993, Chem. Res. Toxicol. 6:585–597.
Corral et al., 1993, Proc. Natl. Acad. Sci. USA 90:8538–8542.
Djabali et al., 1992, Nature Genet. 2:113–118.
Domer et al., 1993, Proc. Natl. Acad. Sci. USA 90:7884–7888.
Epstein, 1988, Lancet 1:521–524.
Felix et al., 1993, Cancer Res. 53:2954–2956.
Felix et al., 1995, Blood, 85:3250–3256.
Felix et al., 1995, Cancer Res. 55:4287–4292.
Felix et al., 1990, J. Clin. Oncol. 8:431–442.
Gale et al., 1997, Proc. Natl. Acad. Sci. USA 94:13950–13954.
Gu et al., 1992, Cell 71:701–708.
Gu et al., 1994, Cancer Res. 54:2327–2330.
Gu et al., 1992, Proc. Natl. Acad. Sci. USA 89:10464–10468.
Hilden et al., 1995, Blood 86:3876–3882.
Hilden et al., 1997, Blood 89:3801–3805.
Jones et al., 1991, BioTechniques 10:62–66.

(List continued on next page.)

*Primary Examiner*—W. Gary Jones
*Assistant Examiner*—Jehanne Souaya
(74) *Attorney, Agent, or Firm*—Dann, Dorfman, Herrell and Skillman

(57) ABSTRACT

The invention relates to kits and methods for panhandle PCR amplification of a region of DNA having an unknown nucleotide sequence, wherein the region flanks a region of a leukemia-associated gene having a known nucleotide sequence in a human patient. Amplification of an unknown region flanking a known region of a leukemia-associated gene permits identification of a translocation partner of the gene or identification of a duplicated sequence within the gene. The invention further relates to kits useful for performing the methods of the invention, to an isolated polynucleotide, and to primers derived from such an isolated polynucleotide.

14 Claims, 27 Drawing Sheets

OTHER PUBLICATIONS

Jones et al., 1993, PCR Meth. Applicat. 2:197–203.
Jones, 1995, PCR Meth. Applicat. 4:S195–S201.
Jones et al., 1992, Nucl. Acids Res. 20:595–600.
Kingma et al., 1995, J. Biol. Chem. 270:21441–21444.
Kingma et al., 1997, Biochemistry 36:5934–5939.
Kobayashi et al., 1993, Genes Chromosomes Cancer 7:204–208.
Liu et al., 1991, In: DNA Topoisomerases in Cancer, Oxford University Press, New York, pp. 13–22.
Long et al., 1985, Cancer Res. 45:3106–3112.
Look et al., 1997, In: *Principles and Practices of Pediatric Oncology*, 3rd ed., Pizzo et al., Eds, Lippincott–Raven Publishers, Philadelphia, PA, Chapter 3.
Ma et al., 1993, Proc. Natl. Acad. Sci USA 90:6350–6354.
Martinez–Climent et al., 1993, Leukemia 9:1299–1304.
Mullis, 1984, PCR Meth. Applicat. 1:1–4.
Nakamura et al., 1993, Proc. Natl. Acad. Sci. USA 90:4631–4635.
Nakao et al., 1996, Leukemia 10:1911–1918.
Negrini et al., 1993, Cancer Res. 53:4489–4492.
Osheroff et al., 1991, In: *DNA Topoisomerases in Cancer*, Potmesil et al., Eds., Oxford University Press, New York, pp. 230–239.
Osheroff, 1989, Biochemistry 28:6157–61604.
Parry et al., 1994 Genes Chromosom. Cancer 11:79–84.
Pedersen–Bjergaard, 1992, Luekemia Res. 16:61–65.
Pedersen–Bjergaard, 1991, Blood 78:1147–1148.
Pommier et al., 1991, Nucl. Acids Res. 19:5973–5980.
Pommier, 1993, Cancer Chemother. Pharmacol. 32:103–108.
Prasad et al., 1993, Cancer Res. 53:5624–5628.
Pui et al., 1990 Lancet 336:417–42.
Pui et al., 1995, Leukemia 9:762–769.
Pui et al., 1991, N. Engl. J. Med. 325:1682–1687.
Raimondi, 1993, Blood 81:2237–2251.
Sambrook et al., 1989, *Molecular Cloning: A Laboratory Manual*, Cold Spring Harbor Laboratory, New York (too voluminous to submit.
Schichman et al., 1994, Cancer Res. 54:4277–4280.
Schichman et al., 1994, Proc. Natl. Acad. Sci USA 91:6236–6239.
So et al., 1997, Proc. Natl. Acad. Sci USA 99:2563–2568.
So et al., 1997, Cancer Res. 57:117–122.
Sobulo et al., 1997, Proc. Natl. Acad. Sci. USA 94:8732–8737.
Sorenson et al., 1992, Blood 80:255a.
Taki et al., 1997, Blood 89:3945–3950.
Thirman et al., 1994, Proc. Natl. Acad. Sci. USA 91:12110–12114.
Tkachuk et al., 1992, Cell 71:691–700.
Tse et al., 1995, Blood 85:650–656.
Wang et al., 1990, Cell 62:403–406.
Winick et al., J. Clin. Oncol. 11:209–217.
Yamamoto et al., 1997, Am. J. Hematol. 55:41–45.
Yamamoto et al., 1994, Blood 83:2912–2921.
Yu et al., 1995, Nature 378:505–508.

* cited by examiner

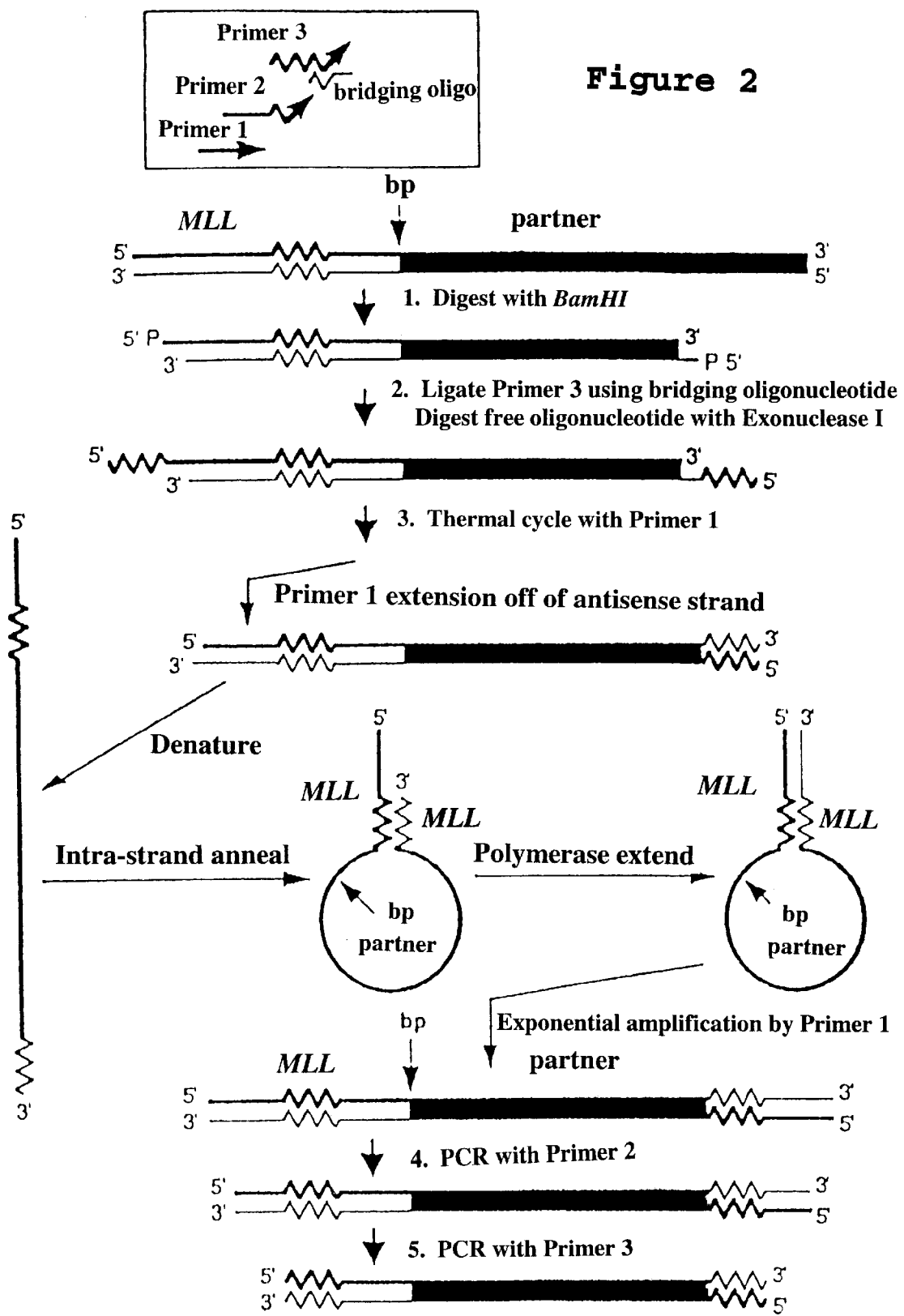

Fig. 4A

```
DEFINITION  Homo sapiens MLL/AF4 translocation breakpoint
t(4;11)(q21;23).
ACCESSION   AF031403
KEYWORDS
SOURCE      human.
  ORGANISM  Homo sapiens
            Eukaryota; Metazoa; Chordata; Vertebrata;
            Mammalia; Eutheria; Primates; Catarrhini; Hominidae; Homo.
REFERENCE   1  (bases 1 to 6990)
  AUTHORS   Felix,C.A., Kim,C.S., Megonigal,M.D., Slater,D.J.,
            Jones,D.H., Spinner,N.B., Stump,T., Hosler,M.R., Nowell,P.C.,
            Lange,B.J. and Rappaport,E.F.
  TITLE     Panhandle polymerase chain reaction amplifies MLL genomic
            translocation breakpoint involving unknown partner gene
  JOURNAL   Blood 90 (12), 4679-4686 (1997) In press
REFERENCE   2  (bases 1 to 6990)
  AUTHORS   Felix,C.A., Kim,C.S., Megonigal,M.D. and Rappaport,E.F.
  TITLE     Direct Submission
JOURNAL     Submitted (24-OCT-1997) Pediatrics, Joseph Stokes, Jr.
      Research Institute, The Children's Hospital of Philadelphia,
      University of Pennsylvania School of Medicine, Division of
      Oncology, Leonard and Madlyn Abramson Pediatric Research
      Center, Rm. 902B, 324 South 34th Street,
            Philadelphia, PA 19104-4318, USA
FEATURES             Location/Qualifiers
     source          1..6990
                     /organism="Homo sapiens"
                     /db_xref="taxon:9606"
                     /note="plasmid subclones 34-1; 34-6; 34-15"
                     /of panhandle PCR product containing genomic
                     t(4;11)(q21;q23) der 11 translocation breakpoint in
                     de novo ALL involving MLL intron 8 and AF-4"
                     /chromosome="4, 11"
                     /map="4q21, D4S1542; 11q23"

BASE COUNT     2093 a   1312 c   1644 g   1941 t
ORIGIN
GGATCCGTGG TCATCCCGCC TCAGCCACCT ACTACAGGAC CGCCAAGAAA AGAAGTTCCC     60

AAAACCACTC CTAGTGAGCC CAAGAAAAAG CAGCCTCCAC CACCAGAATC AGGTGAGTGA    120

GGAGGGCAAG AAGGAATTGC TGACCCACAA GTACTAACAA AAAAGCACTG ATGTCTCAAA    180

CAGCATTTGA AAGCAGGAAA TGTATGATTT GAAGTCTTCA GTTCAAGAAA ATCAGCTCTC    240

TTTCTAACTA TTATGTTTAA TAATAAAGAA ACAGAAACAA AAAAAACAGT TAAATTGGAG    300

GTATTGTTTT AATTTCCTGT TCGAAGCCTA GAGTTTAAAT AGTTTTTTTT TTTTTTTCT    360

AATGGCCCTT TCTTCACAGG TCAGTCAGTA CTAAAGTAGT CGTTGCCAGC ATCTGACTGC    420

AATTTATTCT GAATTTTTTA GGTCCAGAGC AGAGCAAACA GAAAAAGTG GCTCCCCGCC    480

CAAGTATCCC TGTAAAACAA AAACCAAAAG AAAAGGTGAG GAGAGATTTG TTTCTCTGCC    540
```

Fig. 4B

```
ATTTCTCAGG GATGTATTCT ATTTTGTAGG GAAAAGCCTT ATCCTTGACT TCTATGTAGA    600
TGGCAGTGGA ATTTCTTAAA ATTAAGAAAC TTCAAGTTTA GGCTTTTAGC TGGGCACGGT    660
GGCTCACGCT GGTAATCCCA ACACTTAGTG AGGCTGAGGT GGGAGGATTG CTTGAGGCCA    720
GCAGTTCAAG ACCAGCCTGG GCAACATAGC AAGACCCTGT CTTTATTTAA ACCAAAAAAA    780
AAAAAAGAAG AAGAAGAAGT TAGCCAGGCA TGGTGGCAGT TGCGTGTAGT CCCAGGTACT    840
CAGGAGGCTG AGATAGAAGG ATTGTCTTGA GCCCAGGAAT TCAAGGCTGT AGTGAGCTAT    900
GATTGTACCA CTGCAGTCCA GCCTGGGTGA CAAAGCAAAA CACTGTCTCC AAAAAAAATT    960
TAGGCTTGGC AAGGCGCAGC GGCTCACGCC TGTGATCCCA GCACTTTGGG AAGCCGAAGC   1020
AGGCAGATCA CTTGAGGTCA GGAGTTGGAG ACCAGCCTGG CCAACATGGT GAAACCCTGT   1080
CTCTACTGAA AATACAAAAA TTAGCCGGTT GTGGTAGTGG GTGCTTGGTA ATCCTAGCTA   1140
CTTGGGAGGC TGAGGCAGGG GGAATTGCCT GAAACCTGCG AGGCGGAGGC TGCAGTGAGC   1200
CGAGATTGCA TCATTGCACT CTAGCCTGGA CAACAGAGCT AGACTCCATC CCAAAAAAAA   1260
AAAAAAAAAG TAGCCGGGCA CGGTGGCTCA CGCCTGTAAT CCCAGCACTT TGGGAGGCCG   1320
AGGCGGGCGG ATCATGAGGG CAGGAGATCG AGACCATCCT GGCTAACACG GTGAAACCCT   1380
GTCTCTACTA AAAATACAAA AAATTAGCCC GGCGAGGTGG CGGGCGCCTG TAGTCCCAGC   1440
TACTCAGGAG AGTGAGCCAG GAGAATGGCG TGAACCCGGG GGGCGGAGCC TGCAGTGAGC   1500
CGAGATCGCG CCACTGCACT CCAGCTTGGG TGACACCGAG ACTCCGTCTC AAAAAAAAAT   1560
AAAAAGTTTA GGCTTTAGCC TGTTTCTTTT TTGGTTTCTT CCTTGTTGCT TTTCCCTTCT   1620
TTGTGGCCCC ACATGTTCTA GCCTAGGAAT CTGCTTATTC TAAAGGCCAT TTGGCGTAAT   1680
TATTTTTTGA CCCCAACATC CTTTAGCAAT TATTTGTCTG TAAAAATCAC CCTTCCCTGT   1740
ATTCACTATT TTTATTTATT ATGGATAAAG AGATAGTGTG GTGGCTCACA TCTATAATCC   1800
CAGCACTTTG GGGCCCAAG GCGGGAGGAT CACTTGAGGG CAGGAGCTGG AGACCAGCCT   1860
GGGCAGCACA GTGACACACA GTTGCTATAA AAAATTTAAA ACCCAACTAG GCATGGTGGC   1920
ATGCACCTGT AGTCCCAGCT ACTCTTGAGA AGCTGAGGCA GGAGGATCAC GAGCCCACAA   1980
GGTCTAGGCT GCAGTGAGCT GTGACTGTGC CACTGTATTG CAGCCTAGGC AACAAAGCAA   2040
GACCCAGTCT CTTTTAAAAA AAAATTCAAA GATTATTGTT TATGTTGGAA ACATGTTTTT   2100
TAGATCTATT AATAAAATTT GTCATTTGCA TTATTATCTG TTGCAAATGT GAAGGCAAAT   2160
AGGGTGTGAT TTTGTTCTAT ATTCATCTTT TGTCTCCTTA GGAAAAACCA CCTCCGGTCA   2220
ATAAGCAGGA GAATGCAGGC ACTTTGAACA TCCTCAGCAC TCTCTCCAAT GGCAATAGTT   2280
CTAAGCAAAA AATTCCAGCA GATGGAGTCC ACAGGATCAG AGTGGACTTT AAGGTAAAGG   2340
```

Fig. 4C

```
CCAAAGGTGT TGAAAGAGGA AATCAGCACC AACTGGGGGA ATGAATAAGA ACTCCCATTA    2460
GCAGGTGGGT TTAGCGCTGG GAGAGCTTTG GACAGTGTTG TTAGGTCACT GTTTGTGAAC    2520
TGACTGCAGA ACATACATAA TGAAACATTC CTATCCATCC TGAGGAGTAT CAGAGGAAGT    2580
AATTCCTTCA CATGGAAAGT ATCAAACCAT GATGATTCCT TGAGTCAGCA AAACTGTAAG    2640
AGAAATTCAA TCCCAGTGTA TTTTCGCAAT ATCTTCACTA TGAATTGAAC AACTAGGTGA    2700
GCCTTTTAAT AGTCCGTGTC TGAGATTAAA ACTTTTTAAA GCAGCAGTTA TTTTTGGACT    2760
CATTGAAATG AAATACTCTG ACATTGTGAT GTCACACTAA TTTTATGCTT TTCATCCTTA    2820
TTTTCCATCC AAAGTTGTGT AATTGTAAAA CTTTCCTAAG TGACCTTTCT CTCTCCACAG    2880
GAGGATTGTG AAGCAGAAAA TGTGTGGGAG ATGGGAGGCT TAGGAATCTT GACTTCTGTT    2940
CCTATAACAC CCAGGGTGGT TTGCTTTCTC TGTGCCAGTA GTGGGCATGT AGAGGTAAGG    3000
CATCCTGCTT CTTTGTACCC CAGGAAGTAC ATAAATGATT GATCTGGGGA TGAGATTACT    3060
ATAGTCTGTT TTGTTGGTAT TTAGCAGGTA CTATTCCCTG TTTAAACCAG CTAAAGAAAT    3120
GTTTTGAAGT ATTTTAGAGA TTTTAGGAAG GAATCTGCTA TTAGAGTAGC AAAGTTATTG    3180
AGAGTGAAAA GATCAATAAT CCCATCTCTC TTAAATTCAG TCTTTATTAG AGTTCTGATC    3240
TTTCTGTTAG ATGTCTAAAT AAGAGAAAAA ATTATACAGT GGTCTATTAA AAGGGATGCT    3300
ATTGATGGTT ATTTTATATT GTATATCAAA GCCTCTTCAT CTATAAGGAG CTCTTACCAA    3360
TTAATAAGAA AAAGGAATGA CATCCAGAAA AAAAAATAGG CAAAAGACAG AAATAGATAA    3420
TTCACAAAAT TAGAAATAAA TACATGTTGG GTGGCAGGGG GAGGTGAAGG GAGGGTGTCT    3480
GTTTTTTAGC CCTCTAGTGA CCAAAAACTG GAAATTAAAG CATGATAAAA AAAGAATCCT    3540
GAATAAATGG GGACTTTCTG TTGGTGGAAA GAAATATAGA TTAGTTACAA TCTTTCTTTC    3600
TGAGGGAATT ATTTGGAAAT ATATATATCT ATCTTTAAAA TAGGTATATC CGAATATTAT    3660
GGCTTTAAGA AAATATGAGT GGGAAATAAT GTTCTAATG GACAGAGCTA TGGAGTTAGA    3720
ATGCATGGGT TCATTCTACT TCACATTTAA ATGGGACAGT ATTTCCTGAG CTAGAGGGCT    3780
GTTGTGAGAA TTAAATGGGA TATGTTTGCC TGACATTTAG TATATTGTGA GATATACCAC    3840
CTTTCCTTGA CATATTGTGT TAGTAAAAGA AAATTTATGC TGTAGGAAAA TTGTATATTA    3900
TCCATCTTCA AGTAGTCTGT ATAGATGTTA CAGCTGTGCC TAGAAGTCAG CAGAATCCCA    3960
AGAAATATCT TTGTGTTTTA GGTTGGTTTG CTGGTGTTTC ACAGTTGTTG TGATGAAGTA    4020
ATGAAACTCT GTGTCATGGA TTTAATTTTA GTCAAGTTTT TAAATGTTAC ACTTTTTCAA    4080
TAAGAGACTT GAATAGATAT TTTATGCCCT AATAAAGTAC TGAATACTTG CTGTAGTTTC    4140
AGGATTCCAG AATTGCATTA GTTGTGAGAA GTATATGGGG CAAGGGCTAG TGTGTAAAGG    4200
```

Fig. 4D

```
GCTTTTTGAG CCCCGTCACA TTTGAGCATT GTGACAAATA GAAAAAATTA TAGTACTGAA    4260

CTGAACACTG ATGTATAAAG TGTTAATTCT GTGACCTGGG TCACAAATTT AGTAAGGAAA    4320

GGTGTAAGAT TAAACATATT TTCATGGAAT CTCTGAAGGT TCCTGAATCC AATATAGAAG    4380

ATAGGCAACA TTTGTATTGA CTGATAGAGT AAGATGGTTT TACAGGGTAG GAAGCTGGAA    4440

TGTCCCAAGA TATTCATTCA GTTTTTGGTT CACATAGTAT TGATGAGTAT ATAAACTTCT    4500

TTAAAATAGT ATGGAGGCCA GGCACAGTGG CTCACGCCTG TAATCCCAAC ACTTTGGGAA    4560

GCCGAGGCAG GAGGATTCCT CGAGCCCAGG AGTTTGAGAC CAACCTGGAC AACATGGTGA    4620

GACTGTCTCT ACAAAACATT TTAAAAATTA GCGGCTGGGC ACGGTGGCTC ATGTCTATAA    4680

TCTCAGCACT TTGGGAGGCT GAGGTGGGTG GATCATCTGA GGTCAGGAAT TCGAGACCAG    4740

CCTGGGCAAC AGGGTGAAAC CCTGTCTCTA CTAAAAATGC AAAAATTAGC CAGGCATGGT    4800
```

Fig. 5A

```
GGATCCGGAA AAGAGTGAAG AAGGGAATGT CTCGGCCCCT GGGCCTGAAT CCAAACAGGC
CACCACTCCA GCTTCGATCC TGGCTCTAGG GGATGAGGAT GAAAGGAGCC AGGGCAGAGG
CTGAGGTGCT GTCCACCAGG AAAGTGCTGA TAAACCTTCA GGGTTGGGTT GAGAATGCCT
CCAAGATACC CCTCAAGTCA AGCCATTTAT TAGACAAGAA GAAGGAACAA AAAACCTTTC
CCTGTGGAGA GTTCCAGGGC TGAGAGGGGA AAGTAAAGAC AGGCCATGTC AGTACTACCC
TTCTCCTTGT CTCTCCCTAC CTGTTTTTGT TTTTGTTTTT GTTTTGAGAC AGGGTCTCAC
TGTGTTGCCC AGGCTGGAGT TCACTGGTGC AATCATATAG CTCACTGTAA CCTCAAGCTC
TTGAGCTGAA GTGATCCTCT CACCTCAGCC TCCTCAGCAG CTAAGACTAC AAGCACACAC
ACCATTATGC TCAGCTAATT GTTAAATATT TATAGGGATG GGGGCGGTC TATGTTGCCT
AGGCTAGTCT CAAAACTCCT GGCCTACAGT AATCCTCCCA CCTCAGCCTG GCATGACCCC
CTACACCCAG CCAAACTGTC CCATTACAGA GTCTGCAGGG CAATGACCGG TCACTAGAAA
GCCAAACATC AGGGCTTACT TAACCAACTA ATAAAGCATT ATTAAAATTT TCTCCATTCT
AAGGCTTTTG ATGAGACCTG CTTATTAGGA TGGATGTCAC GATCTTGGCC CACAGTGCCA
ATCAATAAGT AAAAATGATT AGGTCTACAA GCAATGGAAA CATGGGTATT ATCATGCAGT
GAAACCCTGC CCTGTTCTGG TACCATGAAG GAAATCTCCA TGAACCCTGT GTCATCTTCA
CCTCTGAAAA TGTTTGAACA GACTCCAGCC TCAATCTCCT TTGAACCTAT ATATCTAATA
ACCTGCTGGC ATAGTTAAAA ATAAATTTAA AAGTTATCAT CATAAAAGCC TTCTAAAAAC
TATTCCTCAC TCAAGAAAAA TTTCTACAGG ATGGTATTAG CAGGAGCAGC AGTAGTCAGT
ACCAAAAACA TTTATTAAGG GGCAGAGAGG TTGCACAGAG AAAGGGGGGG GAAAAATAAT
GGGCAAAATT TAATTCTCAA CTGTTTAAGT TCTTTAAGCA CAAGGAAGCC ATCCGCTGGT
AAGGCAAGAA AATGTTTAAA ATTACCTCCG GCCTAAAACT TATTTTTCTT CTGACACTGC
CCCATCTTTA ACCAGTCTTT CCTCCATGAT ATGAGGACAG TCCAAAACAG TTTTTCCCAA
ACTTCGGTCA TTTCTATACT ACTTTGATAG CGGCACTGCG TCATAATACT ACTTGTACTA
TTTTTTTAGA TCAGTTTATG ATCAACCCAC TTTTTTTTTT TAACCTCACC TCATCCTAAG
```

Fig. 5B

```
CAATATTTGT GAAACCCTAG GTTTGTTTGA TATGCTGGTT TATATTTCTT CCTAATTCAC
ATGACATGAT TTGGCTGTGT CCCCACCCAA ATCTCATCTT GAATTCCCAT GTGTTGTGGG
AGGGAGCTGG TGGGAGGTAA TTCGATCATG GGGGCAGGTC TTTCCCGTGC TGTTCTTGTA
ACAGTGAGTC TCATGAGATC TGATGGTTTT AAAAACAGGA GTTTCCCTGC ACAACCTCTC
TCTTTGCCGC CACTCACGTA GACGTGACCT GCTCCTCCTT GCCTTCCGCA TGACTGTGAG
GCTTCCATGT GGAACTGTGA GTTCTCCACT AAACCTCTTT CCTTTGTAAA TTGCCCAGTC
TCAGGTATGT CTTTATCAGC AGTGTGAAAG CAGACTAATG CACCACATTA AGACACATAA
AATAAAGGTT GGTGTCCCCA CACTATATTA TTTTTTCTTG TGACAGAGTC TGTCAGCCAG
GCTGGAGTGC AGTGGCACGA ACACAGCTCA CTGCAGCCTA CACTTCCTGT GCTCAAGTGA
TCCTCCTACC TCAGCCTCCT GAGCAGCTGG GACCGCAGGT GCATGCCACA ACACCCGGCT
TTTTTTTTTT TTTCTTTTGA GACGGAATTT CACTCTTGTT GCCCAGGCTG GAGTGCAATG
ACGCGATCTC GACTTTACTG CAACCTCCGC TTCCTGGGTT CAAGCAATTC TCCTTCCTCA
GCCTCCTGAG GATTACAGGC ACCCACCACC ATGCCTGGCT AATTTTTGCA TTTTTAGTAG
AGACAGGGTT TCACCCTGTT GCCCAGGCTG GTCTCGAATT CCTGACCTCA GATGATCCAC
CCACCTCAGC CTCCCAAAGT GCTGAGATTA TAGACATGAG CCACCGTGCC CAGCCGCTAA
TTTTTAAAAT GTTTTGTAGA GACAGTCTCA CCATGTTGTC CAGGTTGGTC TCAAACTCCT
GGGCTCGAGG AATCCTCCTG CCTCGGCTTC CCAAAGTGTT GGGATTACAG GCGTGAGCCA
CTGTGCCTGG CCTCCATACT ATTTTAAAGA AGTTTATATA CTCATCAATA CTATGTGAAC
CAAAAACTGA ATGAATATCT TGGGACATTC CAGCTTCCTA CCCTGTAAAA CCATCTTACT
CTATCAGTCA ATACAAATGT TGCCTATCTT CTATATTGGA TTCAGGAACC TTCAGAGATT
CCATGAAAAT ATGTTTAATC TTACACCTTT CCTTACTAAA TTTGTGACCC AGGTCACAGA
ATTAACACTT TATACATCAG TGTTCAGTTC AGTACTATAA TTTTTTCTAT TTGTCACAAT
GCTCAAATGT GACGGGCTC AAAAGCCCT TTACACACTA GCCCTTGCCC CATATACTTC
TCACAACTAA TGCAATTCTG GAATCCTGAA ACTACAGCAA GTATTCAGTA CTTTATTAGG
GCATAAAATA TCTATTCAAG TCTCTTATTG AAAAGTGTA ACATTTAAAA ACTTGACTAA
AATTAAATCC ATGACACAGA GTTTCATTAC TTCATCACAA CAACTGTGAA ACACCAGCAA
```

ACCAACCTAA AACACAAAGA TATTTCTTGG GATTCTGCTG ACTTCTAGGC ACAGCTGTAA

CATCTATACA GACTACTTGA AGATGGATAA TATACAATTT TCCTACAGCA TAAATTTTCT

TTTACTAACA CAATATGTCA AGGAAAGGTG GTATATCTCA CAATATACTA AATGTCAGGC

AAACATATCC CATTTAATTC TCACAACAGC CCTCTAGCTC AGGAAATACT GTCCCATTTA

AATGTGAAGT AGAATGAACC CATGCATTCT AACTCCATAG CTCTGTCCAT TAGAAACATT

ATTTCCCACT CATATTTTCT TAAAGCCATA ATATTC

```
GAATATTATG GCTTTAAGAA AATATGAGTG GGAAATAATG TTTCTAATGG ACAGAGCTAT
GGAGTTAGAA TGCATGGGTT CATTCTACTT CACATTTAAA TGGGACAGTA TTTCCTGAGC
TAGAGGGCTG TTGTGAGAAT TAAATGGGAT ATGTTTGCCT GACATTTAGT ATATTGTGAG
ATATACCACC TTTCCTTGAC ATATTGTGTT AGTAAAAGAA AATTTATGCT GTAGGAAAAT
TGTATATTAT CCATCTTCAA GTAGTCTGTA TAGATGTTAC AGCTGTGCCT AGAAGTCAGC
AGAATCCCAA GAAATATCTT TGTGTTTTAG GTTGGTTTGC TGGTGTTTCA CAGTTGTTGT
GATGAAGTAA TGAAACTCTG TGTCATGGAT TTAATTTTAG TCAAGTTTTT AAATGTTACA
CTTTTTCAAT AAGAGACTTG AATAGATATT TTATGCCCTA ATAAAGTACT GAATACTTGC
TGTAGTTTCA GGATTCCAGA ATTGCATTAG TTGTGAGAAG TATATGGGGC AAGGGCTAGT
GTGTAAAGGG CTTTTTGAGC CCCGTCACAT TTGAGCATTG TGACAAATAG AAAAAATTAT
AGTACTGAAC TGAACACTGA TGTATAAAGT GTTAATTCTG TGACCTGGGT CACAAATTTA
GTAAGGAAAG GTGTAAGATT AAACATATTT TCATGGAATC TCTGAAGGTT CCTGAATCCA
ATATAGAAGA TAGGCAACAT TTGTATTGAC TGATAGAGTA AGATGGTTTT ACAGGGTAGG
AAGCTGGAAT GTCCCAAGAT ATTCATTCAG TTTTTGGTTC ACATAGTATT GATGAGTATA
TAAACTTCTT TAAAATAGTA TGGAGGCCAG GCACAGTGGC TCACGCCTGT AATCCCAACA
CTTTGGGAAG CCGAGGCAGG AGGATTCCTC GAGCCCAGGA GTTTGAGACC AACCTGGACA
ACATGGTGAG ACTGTCTCTA CAAAACATTT TAAAAATTAG CGGCTGGGCA CGGTGGCTCA
TGTCTATAAT CTCAGCACTT TGGGAGGCTG AGGTGGGTGG ATCATCTGAG GTCAGGAATT
CGAGACCAGC CTGGGCAACA GGGTGAAACC CTGTCTCTAC TAAAAATGCA AAAATTAGCC
AGGCATGGTG GTGGGTGCCT GTAATCCTCA GGAGGCTGAG GAAGGAGAAT TGCTTGAACC
CAGGAAGCGG AGGTTGCAGT AAAGTCGAGA TCGCGTCATT GCACTCCAGC CTGGGCAACA
AGAGTGAAAT TCCGTCTCAA AAGAAAAAAA AAAAAAGCC GGGTGTTGTG GCATGCACCT
GCGGTCCCAG CTGCTCAGGA GGCTGAGGTA GGAGGATCAC TTGAGCACAG GAAGTGTAGG
CTGCAGTGAG CTGTGTTCGT GCCACTGCAC TCCAGCCTGG CTGACAGACT CTGTCACAAG
AAAAAATAAT ATAGTGTGGG GACACCAACC TTTATTTTAT GTGTCTTAAT GTGGTGCATT
AGTCTGCTTT CACACTGCTG ATAAAGACAT ACCTGAGACT GGGCAATTTA CAAAGGAAAG
AGGTTTAGTG GAGAACTCAC AGTTCCACAT GGAAGCCTCA CAGTCATGCG GAAGGCAAGG
```

FIGURE 6B

```
AGGAGCAGGT CACGTCTACG TGAGTGGCGG CAAAGAGAGA GGTTGTGCAG GGAAACTCCT
GTTTTTAAAA CCATCAGATC TCATGAGACT CACTGTTACA AGAACAGCAC GGGAAAGACC
TGCCCCCATG ATCGAATTAC CTCCCACCAG CTCCCTCCCA CAACACATGG GAATTCAAGA
TGAGATTTGG GTGGGGACAC AGCCAAATCA TGTCATGTGA ATTAGGAAGA AATATAAACC
AGCATATCAA ACAAACCTAG GGTTTCACAA ATATTGCTTA GGATGAGGTG AGGTTAAAAA
AAAAAAGTGG GTTGATCATA AACTGATCTA AAAAATAGT ACAAGTAGTA TTATGACGCA
GTGCCGCTAT CAAAGTAGTA TAGAAATGAC CGAAGTTTGG GAAAACTGT TTGGACTGT
CCTCATATCA TGGAGGAAAG ACTGGTTAAA GATGGGGCAG TGTCAGAAGA AAAATAAGTT
TTAGGCCGGA GGTAATTTTA AACATTTTCT TGCCTTACCA GCGGATGGCT TCCTTGTGCT
TAAAGAACTT AAACAGTTGA GAATTAAATT TTGCCCATTA TTTTTCCCCC CCCTTTCTCT
GTGCAACCTC TCTGCCCCTT AATAAATGTT TTTGGTACTG ACTACTGCTG CTCCTGCTAA
TACCATCCTG TAGAAATTTT TCTTGAGTGA GGAATAGTTT TTAGAAGGCT TTTATGATGA
TAACTTTTAA ATTTATTTTT AACTATGCCA GCAGGTTATT AGATATATAG GTTCAAAGGA
GATTGAGGCT GGAGTCTGTT CAAACATTTT CAGAGGTGAA GATGACACAG GGTTCATGGA
GATTTCCTTC ATGGTACCAG AACAGGGCAG GGTTTCACTG CATGATAATA CCCATGTTTC
CATTGCTTGT AGACCTAATC ATTTTTACTT ATTGATTGGC ACTGTGGGCC AAGATCGTGA
CATCCATCCT AATAAGCAGG TCTCATCAAA AGCCTTAGAA TGGAGAAAAT TTTAATAATG
CTTTATTAGT TGGTTAAGTA AGCCCTGATG TTTGGCTTTC TAGTGACCGG TCATTGCCCT
GCAGACTCTG TAATGGGACA GTTTGGCTGG GTGTAGGGGG TCATGCCAGG CTGAGGTGGG
AGGATTACTG TAGGCCAGGA GTTTTGAGAC TAGCCTAGGC AACATAGACC GCCCCCCATC
CCTATAAATA TTTAACAATT AGCTGAGCAT AATGGTGTGT GTGCTTGTAG TCTTAGCTGC
TGAGGAGGCT GAGGTGAGAG GATCACTTCA GCTCAAGAGC TTGAGGTTAC AGTGAGCTAT
ATGATTGCAC CAGTGAACTC CAGCCTGGGC AACACAGTGA GACCCTGTCT CAAAACAAAA
ACAAAAACAA AAACAGGTAG GGAGAGACAA GGAGAAGGGT AGTACTGACA TGGCCTGTCT
TTACTTTCCC CTCTCAGCCC TGGAACTCTC CACAGGGAAA GGTTTTTTGT TCCTTCTTCT
TGTCTAATAA ATGGCTTGAC TTGAGGGGTA TCTTGGAGGC ATTCTCAACC CAACCCTGAA
GGTTTATCAG CACTTTCCTG GTGGACAGCA CCTCAGCCTC TGCCCTGGCT CCTTTCATCC
TCATCCCCTA GAGCCAGGAT CGAAGCTGGA GTGGTGGCCT GTTTGGATTC AGGCCCAGGG
GCCGAGACAT TCCCTTCTTC ACTCTTTTCC GGATCC
```

FIGURE 7A

```
GGATCCGTGG TCATCCCGCC TCAGCCACCT ACTACAGGAC CGCCAAGAAA AGAAGTTCCC
AAAACCACTC CTAGTGAGCC CAAGAAAAAG CAGCCTCCAC CACCAGAATC AGGTGAGTGA
GGAGGGCAAG AAGGAATTGC TGACCCACAA GTACTAACAA AAAAGCACTG ATGTCTCAAA
CAGCATTTGA AAGCAGGAAA TGTATGATTT GAAGTCTTCA GTTCAAGAAA ATCAGCTCTC
TTTCTAACTA TTATGTTTAA TAATAAAGAA ACAGAAACAA AAAAAACAGT TAAATTGGAG
GTATTGTTTT AATTTCCTGT TCGAAGCCTA GAGTTTAAAT AGTTTTTTTT TTTTTTTCT
AATGGCCCTT TCTTCACAGG TCAGTCAGTA CTAAAGTAGT CGTTGCCAGC ATCTGACTGC
AATTTATTCT GAATTTTTTA GGTCCAGAGC AGAGCAAACA GAAAAAGTG GCTCCCCGCC
CAAGTATCCC TGTAAAACAA AAACCAAAAG AAAAGGTGAG GAGAGATTTG TTTCTCTGCC
ATTTCTCAGG GATGTATTCT ATTTTGTAGG GAAAAGCCTT ATCCTTGACT TCTATGTAGA
TGGCAGTGGA ATTTCTTAAA ATTAAGAAAC TTCAAGTTTA GGCTTTTAGC TGGGCACGGT
GGCTCACGCT GGTAATCCCA ACACTTAGTG AGGCTGAGGT GGGAGGATTG CTTGAGGCCA
GCAGTTCAAG ACCAGCCTGG GCAACATAGC AAGACCCTGT CTTTATTTAA ACCAAAAAAA
AAAAAGAAG AAGAAGAAGT TAGCCAGGCA TGGTGGCAGT TGCGTGTAGT CCCAGGTACT
CAGGAGGCTG AGATAGAAGG ATTGTCTTGA GCCCAGGAAT TCAAGGCTGT AGTGAGCTAT
GATTGTACCA CTGCAGTCCA GCCTGGGTGA CAAAGCAAAA CACTGTCTCC AAAAAAATT
TAGGCTTGGC AAGGCGCAGC GGCTCACGCC TGTGATCCCA GCACTTTGGG AAGCCGAAGC
AGGCAGATCA CTTGAGGTCA GGAGTTGGAG ACCAGCCTGG CCAACATGGT GAAACCCTGT
CTCTACTGAA AATACAAAAA TTAGCCGGTT GTGGTAGTGG GTGCTTGGTA ATCCTAGCTA
CTTGGGAGGC TGAGGCAGGG GGAATTGCCT GAAACCTGCG AGGCGGAGGC TGCAGTGAGC
CGAGATTGCA TCATTGCACT CTAGCCTGGA CAACAGAGCT AGACTCCATC CCAAAAAAAA
AAAAAAAAG TAGCCGGGCA CGGTGGCTCA CGCCTGTAAT CCCAGCACTT TGGGAGGCCG
AGGCGGGCGG ATCATGAGGG CAGGAGATCG AGACCATCCT GGCTAACACG GTGAAACCCT
GTCTCTACTA AAAATACAAA AAATTAGCCC GGCGAGGTGG CGGGCGCCTG TAGTCCCAGC
TACTCAGGAG AGTGAGCCAG GAGAATGGCG TGAACCCGGG GGGCGGAGCC TGCAGTGAGC
CGAGATCGCG CCACTGCACT CCAGCTTGGG TGACACCGAG ACTCCGTCTC AAAAAAAAT
AAAAGTTTA GGCTTTAGCC TGTTTCTTTT TTGGTTTCTT CCTTGTTGCT TTTCCCTTCT
TTGTGGCCCC ACATGTTCTA GCCTAGGAAT CTGCTTATTC TAAAGGCCAT TTGGCGTAAT
TATTTTTTGA CCCCAACATC CTTTAGCAAT TATTTGTCTG TAAAAATCAC CCTTCCCTGT
```

FIGURE 7B

```
ATTCACTATT TTTATTTATT ATGGATAAAG AGATAGTGTG GTGGCTCACA TCTATAATCC
CAGCACTTTG GGGGCCCAAG GCGGGAGGAT CACTTGAGGG CAGGAGCTGG AGACCAGCCT
GGGCAGCACA GTGACACACA GTTGCTATAA AAAATTTAAA ACCCAACTAG GCATGGTGGC
ATGCACCTGT AGTCCCAGCT ACTCTTGAGA AGCTGAGGCA GGAGGATCAC GAGCCCACAA
GGTCTAGGCT GCAGTGAGCT GTGACTGTGC CACTGTATTG CAGCCTAGGC AACAAAGCAA
GACCCAGTCT CTTTTAAAAA AAAATTCAAA GATTATTGTT TATGTTGGAA ACATGTTTTT
TAGATCTATT AATAAAATTT GTCATTTGCA TTATTATCTG TTGCAAATGT GAAGGCAAAT
AGGGTGTGAT TTTGTTCTAT ATTCATCTTT TGTCTCCTTA GGAAAAACCA CCTCCGGTCA
ATAAGCAGGA GAATGCAGGC ACTTTGAACA TCCTCAGCAC TCTCTCCAAT GGCAATAGTT
CTAAGCAAAA AATTCCAGCA GATGGAGTCC ACAGGATCAG AGTGGACTTT AAGGTAAAGG
TGTTCAGTGA TCATAAAGTA TATTGAGTGT CAAAGACTTT AAATAAAGAA AATGCTACTA
CCAAAGGTGT TGAAAGAGGA AATCAGCACC AACTGGGGGA ATGAATAAGA ACTCCCATTA
GCAGGTGGGT TTAGCGCTGG GAGAGCTTTG GACAGTGTTG TTAGGTCACT GTTTGTGAAC
TGACTGCAGA ACATACATAA TGAAACATTC CTATCCATCC TGAGGAGTAT CAGAGGAAGT
AATTCCTTCA CATGGAAAGT ATCAAACCAT GATGATTCCT TGAGTCAGCA AAACTGTAAG
AGAAATTCAA TCCCAGTGTA TTTTCGCAAT ATCTTCACTA TGAATTGAAC AACTAGGTGA
GCCTTTTAAT AGTCCGTGTC TGAGATTAAA ACTTTTTAAA GCAGCAGTTA TTTTTGGACT
CATTGAAATG AAATACTCTG ACATTGTGAT GTCACACTAA TTTTATGCTT TTCATCCTTA
TTTTCCATCC AAAGTTGTGT AATTGTAAAA CTTTCCTAAG TGACCTTTCT CTCTCCACAG
GAGGATTGTG AAGCAGAAAA TGTGTGGGAG ATGGGAGGCT TAGGAATCTT GACTTCTGTT
CCTATAACAC CCAGGGTGGT TTGCTTTCTC TGTGCCAGTA GTGGGCATGT AGAGGTAAGG
CATCCTGCTT CTTTGTACCC CAGGAAGTAC ATAAATGATT GATCTGGGGA TGAGATTACT
ATAGTCTGTT TTGTTGGTAT TTAGCAGGTA CTATTCCCTG TTTAAACCAG CTAAAGAAAT
GTTTTGAAGT ATTTTAGAGA TTTTAGGAAG GAATCTGCTA TTAGAGTAGC AAAGTTATTG
AGAGTGAAAA GATCAATAAT CCCATCTCTC TTAAATTCAG TCTTTATTAG AGTTCTGATC
TTTCTGTTAG ATGTCTAAAT AAGAGAAAAA ATTATACAGT GGTCTATTAA AAGGGATGCT
ATTGATGGTT ATTTTATATT GTATATCAAA GCCTCTTCAT CTATAAGGAG CTCTTACCAA
TTAATAAGAA AAAGGAATGA CATCCAGAAA AAAAAATAGG CAAAAGACAG AAATAGATAA
```

FIGURE 7C

```
TTCACAAAAT TAGAAATAAA TACATGTTGG GTGGCAGGGG GAGGTGAAGG GAGGGTGTCT
GTTTTTTAGC CCTCTAGTGA CCAAAAACTG GAAATTAAAG CATGATAAAA AAAGAATCCT
GAATAAATGG GGACTTTCTG TTGGTGGAAA GAAATATAGA TTAGTTACAA TCTTTCTTTC
TGAGGGAATT ATTTGGAAAT ATATATATCT ATCTTTAAAA TAGGTATATC CGAATATTAT
GGCTTTAAGA AAATATGAGT GGGAAATAAT GTTTCTAATG GACAGAGCTA TGGAGTTAGA
ATGCATGGGT TCATTCTACT TCACATTTAA ATGGGACAGT ATTTCCTGAG CTAGAGGGCT
GTTGTGAGAA TTAAATGGGA TATGTTTGCC TGACATTTAG TATATTGTGA GATATACCAC
CTTTCCTTGA CATATTGTGT TAGTAAAAGA AAATTTATGC TGTAGGAAAA TTGTATATTA
TCCATCTTCA AGTAGTCTGT ATAGATGTTA CAGCTGTGCC TAGAAGTCAG CAGAATCCCA
AGAAATATCT TTGTGTTTTA GGTTGGTTTG CTGGTGTTTC ACAGTTGTTG TGATGAAGTA
ATGAAACTCT GTGTCATGGA TTTAATTTTA GTCAAGTTTT TAAATGTTAC ACTTTTTCAA
TAAGAGACTT GAATAGATAT TTTATGCCCT AATAAAGTAC TGAATACTTG CTGTAGTTTC
AGGATTCCAG AATTGCATTA GTTGTGAGAA GTATATGGGG CAAGGGCTAG TGTGTAAAGG
GCTTTTTGAG CCCCGTCACA TTTGAGCATT GTGACAAATA GAAAAAATTA TAGTACTGAA
CTGAACACTG ATGTATAAAG TGTTAATTCT GTGACCTGGG TCACAAATTT AGTAAGGAAA
GGTGTAAGAT TAAACATATT TTCATGGAAT CTCTGAAGGT TCCTGAATCC AATATAGAAG
ATAGGCAACA TTTGTATTGA CTGATAGAGT AAGATGGTTT TACAGGGTAG GAAGCTGGAA
TGTCCCAAGA TATTCATTCA GTTTTTGGTT CACATAGTAT TGATGAGTAT ATAAACTTCT
TTAAAATAGT ATGGAGGCCA GGCACAGTGG CTCACGCCTG TAATCCCAAC ACTTTGGGAA
GCCGAGGCAG GAGGATTCCT CGAGCCCAGG AGTTTGAGAC CAACCTGGAC AACATGGTGA
GACTGTCTCT ACAAAACATT TTAAAAATTA GCGGCTGGGC ACGGTGGCTC ATGTCTATAA
TCTCAGCACT TTGGGAGGCT GAGGTGGGTG GATCATCTGA GGTCAGGAAT TCGAGACCAG
CCTGGGCAAC AGGGTGAAAC CCTGTCTCTA CTAAAAATGC AAAAATTAGC CAGGCATGGT
GGTGGGTGCC TGTAATCCTC AGGAGCTGA GGAAGGAGAA TTGCTTGAAC CCAGGAAGCG
GAGGTTGCAG TAAAGTCGAG ATCGCGTCAT TGCACTCCAG CCTGGGCAAC AAGAGTGAAA
TTCCGTCTCA AAGAAAAAA AAAAAAAGC CGGGTGTTGT GGCATGCACC TGCGGTCCCA
GCTGCTCAGG AGGCTGAGGT AGGAGGATCA CTTGAGCACA GGAAGTGTAG GCTGCAGTGA
GCTGTGTTCG TGCCACTGCA CTCCAGCCTG GCTGACAGAC TCTGTCACAA GAAAAAATAA
TATAGTGTGG GGACACCAAC CTTTATTTTA TGTGTCTTAA TGTGGTGCAT TAGTCTGCTT
TCACACTGCT GATAAAGACA TACCTGAGAC TGGGCAATTT ACAAAGGAAA GAGGTTTAGT
```

FIGURE 7D

```
GGAGAACTCA CAGTTCCACA TGGAAGCCTC ACAGTCATGC GGAAGGCAAG GAGGAGCAGG
TCACGTCTAC GTGAGTGGCG GCAAAGAGAG AGGTTGTGCA GGGAAACTCC TGTTTTTAAA
ACCATCAGAT CTCATGAGAC TCACTGTTAC AAGAACAGCA CGGGAAAGAC CTGCCCCCAT
GATCGAATTA CCTCCCACCA GCTCCCTCCC ACAACACATG GAATTCAAG ATGAGATTTG
GGTGGGGACA CAGCCAAATC ATGTCATGTG AATTAGGAAG AAATATAAAC CAGCATATCA
AACAAACCTA GGGTTTCACA AATATTGCTT AGGATGAGGT GAGGTTAAAA AAAAAAGTG
GGTTGATCAT AAACTGATCT AAAAAAATAG TACAAGTAGT ATTATGACGC AGTGCCGCTA
TCAAAGTAGT ATAGAAATGA CCGAAGTTTG GGAAAAACTG TTTTGGACTG TCCTCATATC
ATGGAGGAAA GACTGGTTAA AGATGGGGCA GTGTCAGAAG AAAAATAAGT TTTAGGCCGG
AGGTAATTTT AAACATTTTC TTGCCTTACC AGCGGATGGC TTCCTTGTGC TTAAAGAACT
TAAACAGTTG AGAATTAAAT TTTGCCCATT ATTTTTCCCC CCCCTTTCTC TGTGCAACCT
CTCTGCCCCT TAATAAATGT TTTTGGTACT GACTACTGCT GCTCCTGCTA ATACCATCCT
GTAGAAATTT TTCTTGAGTG AGGAATAGTT TTTAGAAGGC TTTTATGATG ATAACTTTTA
AATTTATTTT TAACTATGCC AGCAGGTTAT TAGATATATA GGTTCAAAGG AGATTGAGGC
TGGAGTCTGT TCAAACATTT TCAGAGGTGA AGATGACACA GGGTTCATGG AGATTTCCTT
CATGGTACCA GAACAGGGCA GGGTTTCACT GCATGATAAT ACCCATGTTT CCATTGCTTG
TAGACCTAAT CATTTTTACT TATTGATTGG CACTGTGGGC CAAGATCGTG ACATCCATCC
TAATAAGCAG GTCTCATCAA AAGCCTTAGA ATGGAGAAAA TTTTAATAAT GCTTTATTAG
TTGGTTAAGT AAGCCCTGAT GTTTGGCTTT CTAGTGACCG GTCATTGCCC TGCAGACTCT
GTAATGGGAC AGTTTGGCTG GGTGTAGGGG GTCATGCCAG GCTGAGGTGG GAGGATTACT
GTAGGCCAGG AGTTTGAGA CTAGCCTAGG CAACATAGAC CGCCCCCCAT CCCTATAAAT
ATTTAACAAT TAGCTGAGCA TAATGGTGTG TGTGCTTGTA GTCTTAGCTG CTGAGGAGGC
TGAGGTGAGA GGATCACTTC AGCTCAAGAG CTTGAGGTTA CAGTGAGCTA TATGATTGCA
CCAGTGAACT CCAGCCTGGG CAACACAGTG AGACCCTGTC TCAAAACAAA AACAAAAACA
AAAACAGGTA GGGAGAGACA AGGAGAAGGG TAGTACTGAC ATGGCCTGTC TTTACTTTCC
CCTCTCAGCC CTGGAACTCT CCACAGGGAA AGGTTTTTTG TTCCTTCTTC TTGTCTAATA
AATGGCTTGA CTTGAGGGGT ATCTTGGAGG CATTCTCAAC CCAACCCTGA AGGTTTATCA
GCACTTTCCT GGTGGACAGC ACCTCAGCCT CTGCCCTGGC TCCTTTCATC CTCATCCCCT
AGAGCCAGGA TCGAAGCTGG AGTGGTGGCC TGTTTGGATT CAGGCCCAGG GGCCGAGACA
TTCCCTTCTT CACTCTTTTC CGGATCC
```

FIGURE 11

```
LOCUS       AF024540      228 bp    mRNA           PRI      24-OCT-1997
DEFINITION  Homo sapiens rearranged MLL protein mRNA, partial cds.
ACCESSION   AF024540
NID         g2558905
KEYWORDS    .
SOURCE      human.
  ORGANISM  Homo sapiens
            Eukaryotae; Metazoa; Chordata; Vertebrata; Mammalia; Eutheria;
            Primates; Catarrhini; Hominidae; Homo.
REFERENCE   1  (bases 1 to 228)
  AUTHORS   Megonigal,M.D., Rappaport,E.F., Jones,D.H., Kim,C.S., Nowell,P.C.,
            Lange,B.J. and Felix,C.A.
  TITLE     Panhandle PCR strategy to amplify MLL genomic breakpoints in
            treatment-related leukemias
  JOURNAL   Proc. Natl. Acad. Sci. U.S.A. 94 (21), 11583-11588 (1997)
  MEDLINE   97471010
REFERENCE   2  (bases 1 to 228)
  AUTHORS   Megonigal,M.D., Rappaport,E.F. and Felix,C.A.
  TITLE     Direct Submission
  JOURNAL   Submitted (10-SEP-1997) Pediatrics, Joseph Stokes, Jr. Research
            Institute, Children's Hospital of Philadelphia, University of
            Pennsylvania School of Medicine, Leonard and Madlyn Abramson
            Pediatric Research Center, Rm. 902B, Children's Hospital of
            Philadelphia, 324 South 34th Street, Philadelphia, PA 19104, USA
FEATURES             Location/Qualifiers
     source          1..228
                     /organism="Homo sapiens"
                     /db_xref="taxon:9606"
                     /chromosome="11"
                     /map="11q23"
                     /note="genomic exon 6 - exon 2 breakpoint junction of MLL
                     partial duplication in treatment-related AML"
     CDS             <1..>228
                     /note="exon 6 - exon 2 fusion"
                     /codon_start=3
                     /product="rearranged MLL protein"
                     /db_xref="PID:g2558906"
                     /translation="PEQSKQKKVAPRPSIPVKQKPKEKDEQFLGFGSDEEVRVRSPTR
                     SPSVKTSPRKPRGRPRSGSDRNSAILSDPSV"
BASE COUNT       76 a     55 c     50 g     47 t
ORIGIN
        1 gtccagagca gagcaaacag aaaaaagtgg ctccccgccc aagtatccct gtaaaacaaa
       61 aaccaaaaga aaaggatgag caattcttag gttttggctc agatgaagaa gtcagagtgc
      121 gaagtccacc aaggtctcct tcagttaaaa ctagtcctcg aaaacctcgt gggagaccta
      181 gaagtggctc tgaccgaaat tcagctatcc tctcagatcc atctgtgt
```

FIGURE 12

```
LOCUS       AF024541       495 bp    mRNA            PRI       24-OCT-1997
DEFINITION  Homo sapiens MLL-AF4 fusion protein mRNA, partial cds.
ACCESSION   AF024541
NID         g2558907
KEYWORDS    .
SOURCE      human.
  ORGANISM  Homo sapiens
            Eukaryotae; Metazoa; Chordata; Vertebrata; Mammalia; Eutheria;
            Primates; Catarrhini; Hominidae; Homo.
REFERENCE   1  (bases 1 to 495)
  AUTHORS   Megonigal,M.D., Rappaport,E.F., Jones,D.H., Kim,C.S., Nowell,P.C.,
            Lange,B.J. and Felix,C.A.
  TITLE     Panhandle PCR strategy to amplify MLL genomic breakpoints in
            treatment-related leukemias
  JOURNAL   Proc. Natl. Acad. Sci. U.S.A. 94 (21), 11583-11588 (1997)
  MEDLINE   97471010
REFERENCE   2  (bases 1 to 495)
  AUTHORS   Megonigal,M.D., Rappaport,E.F. and Felix,C.A.
  TITLE     Direct Submission
  JOURNAL   Submitted (10-SEP-1997) Pediatrics, Joseph Stokes, Jr. Research
            Institute, Children's Hospital of Philadelphia, University of
            Pennsylvania School of Medicine, Leonard and Madlyn Abramson
            Pediatric Research Center, Rm. 902B, Children's Hospital of
            Philadelphia, 324 South 34th Street, Philadelphia, PA 19104, USA
FEATURES             Location/Qualifiers
     source          1..495
                     /organism="Homo sapiens"
                     /db_xref="taxon:9606"
                     /chromosome="4, 11"
                     /map="t(4;11)(q21;q23)"
                     /note="genomic t(4;11)(q21;q23) translocation breakpoint
                     in treatment related AML involving MLL exon 6 and AF-4"
     CDS             <1..>495
                     /codon_start=3
                     /product="MLL-AF4 fusion protein"
                     /db_xref="PID:g2558908"
```

/translation="KQKKVAPRPSIPVKQKPKEKQTYSNEVHCVEEILKEMTHSWPPP

LTAIHTPSTAEPSKFPFPTKDSQHVSSVTQNQKQYDTSSKTHSNSQQGTSSMLEDDLQ

LSDSEDSDSEQTPEKPPSSSAPPSAPQSLPEPVASAHSSSAESESTSDSDSSSDSESE
                    SSSS"

```
BASE COUNT      165 a    143 c      92 g      95 t
ORIGIN
        1 gcaaacagaa aaaagtggct ccccgcccaa gtatccctgt aaaacaaaaa ccaaaagaaa
       61 agcagaccta ctccaatgaa gtccattgtg ttgaagagat tctgaaggaa atgacccatt
      121 catggccgcc tcctttgaca gcaatacata cgcctagtac agctgagcca tccaagtttc
      181 ctttccctac aaaggactct cagcatgtca gttctgtaac ccaaaaccaa aaacaatatg
      241 atacatcttc aaaaactcac tcaaattctc agcaggaac gtcatccatg ctcgaagacg
      301 accttcagct cagtgacagt gaggacagtg acagtgaaca acccccagag aagcctccct
      361 cctcatctgc acctccaagt gctccacagt cccttccaga accagtggca tcagcacatt
      421 ccagcagtgc agagtcagaa agcaccagtg actcagacag ttcctcagac tcagagagcg
      481 agagcagttc aagtg
```

FIGURE 13A

```
LOCUS       AF024542     3441 bp    DNA              PRI       21-OCT-1997
DEFINITION  Homo sapiens MLL breakpoint junction region chromosome 11q23.
ACCESSION   AF024542
NID         g2547404
KEYWORDS
SOURCE      human.
  ORGANISM  Homo sapiens
            Eukaryotae; Metazoa; Chordata; Vertebrata; Mammalia; Eutheria;
            Primates; Catarrhini; Hominidae; Homo.
REFERENCE   1  (bases 1 to 3441)
  AUTHORS   Megonigal,M.D., Rappaport,E.F., Jones,D.H., Kim,C.S.,
Nowell,P.C.,
            Lange,B.J. and Felix,C.A.
  TITLE     Panhandle PCR strategy to amplify MLL genomic breakpoints in
            treatment-related leukemias
  JOURNAL   Proc. Natl. Acad. Sci. U.S.A. 94 (21), 11583-11588 (1997)
  MEDLINE   97471010
REFERENCE   2  (bases 1 to 3441)
  AUTHORS   Megonigal,M.D., Rappaport,E.F. and Felix,C.A.
  TITLE     Direct Submission
  JOURNAL   Submitted (10-SEP-1997) Pediatrics, Joseph Stokes, Jr. Research
            Institute, Children's Hospital of Philadelphia, University of
            Pennsylvania School of Medicine, Leonard and Madlyn Abramson
            Pediatric Research Center, Rm. 902B, Children's Hospital of
            Philadelphia, 324 South 34th Street, Philadelphia, PA 19104,
USA
FEATURES             Location/Qualifiers
     source          1..3441
                     /organism="Homo sapiens"
                     /db_xref="taxon:9606"
                     /chromosome="11"
                     /map="11q23; D11S2060, 11q23.3"
                     /sub_clone="plasmid subclone 35-1"
                     /clone_lib="panhandle PCR products containing genomic
                     intron 6 - intron 1 breakpoint junction of MLL partial
                     duplication in treatment-related AML"
BASE COUNT      970 a    719 c    778 g    974 t
ORIGIN
        1 ggatccgtgg tcatcccgcc tcagccacct actacaggac cgccaagaaa agaagttccc
       61 aaaaccactc ctagtgagcc caagaaaaag cagcctccac caccagaatc aggtgagtga
      121 ggagggcaag aaggaattgc tgaaccacaa gtactaacaa aaaagcactg atgtctcaaa
      181 cagcatttga aagcaggaaa tgtatgattt gaagtcttca gttcaagaaa atcagctctc
      241 tttctaacta ttatgtttaa taataaagaa acagaaacaa aaaaacagtt aaattggagg
      301 tattgtttta atttcctgtt cgaagcctag agtttaaata gttttttttt ttttttttcta
      361 atggcccttt cttcacaggt cagtcagtac taaagtagtc gttgccagca tctgactgca
      421 atttattctg aatttttag gtccagagca gagcaaacag aaaaaagtgg ctccccgccc
```

FIGURE 13B

```
 481 aagtatccct gtaaaacaaa aaccaaaaga aaaggtgagg agagatttgt ttctctgcca
 541 tttctcaggg gtgtattcta ttttgtagga aaagccttat ccttgacttc tatgtagatg
 601 gcagtggaat ttcttaaaat taagaaactt caagtttagg cttttagctg ggcacggtgg
 661 ctcacgctgg taatcccaac acttagtgag gctgaggtgg gaggattgct tgaggccagc
 721 agttcaagac cagcctgggc aacatagcaa gaccctgtct ttatttaaac aaaaaaaaaa
 781 aaagaagaag aagaagaagt tagccaggca tggtggcagt tgcgtgtagt cccaggtact
 841 caggaggctg agatagaagg attgccttga gcccaggaat tcaaggctgt agtgagctat
 901 gattgtacca ctgcagtcca gcctggtgca caaagcaaaa cactgtctcc aaaaaaaatt
 961 taggcttggc aaggcgcagc ggctcacgcc tgtgatccca gcactttggg aagccgaagc
1021 aggcagatca cttgaggtca ggagttggag accagcctgg ccaacatggt gaaaccctgt
1081 ctctactgaa aatacaaaaa ttagccggtt gtggtagtgg gtgcttgtaa tcctagctac
1141 ttgggaggct gaggcagggg aattgcctga acctgcgagg cggaggctgc agtgagccga
1201 gattgcatca ttgcactcta gcctggacaa cagagctaga ctccatccca aaaaaaaaaa
1261 agtagccggg cacggtggct cacgcctgta atcccagcac tttgggaggc cgaggcgggc
1321 ggatcatgag ggcacctcat gtgagccacc tcgtcctgcc cctatacatt cttaaaagta
1381 agaatcatat tgtgtaattc tttgaagtcc ctcagtattt tctactatag tactattacc
1441 acagtaggta tttaatgttc ttaaaacaag tttattgcat ttcttttatt ttcattttac
1501 aaacatttat tgggtgccaa atttgtgcta gatattagaa atacaaaaat gaataggaaa
1561 actgtttcta tcctcagagt acacactcta aagaagacaa atgtgtgaac acattttta
1621 aaattccttc tgctaatact agtaattatg tgagcatgtc tttaaggtgc aacattaaga
1681 ccttggtatt ttgaagcttg tagcagtagc cacaagggga aatgtgccag ctgaagtgat
1741 agctacctgg aataaattcc caaggggaa gtggtattct ttttaaactt atcgctgcca
1801 agatgcacag tttgcctcct ggatatttct tcaactttag ttgttctcag taattttgtt
1861 agttctcctg tggcctcctc atttgatgga atgatatata atggtactag aagccttcaa
1921 aacaaagtat ttcaaaaaac aagtgcatca ggagtgattt tgatactgtc tatggtattg
1981 atgttatttt caattgattc attgaaattt gttttgtaat tgaagggatt tgatttttca
2041 aactcttttt tttccccct ttgagacaga tcttgctct gttacccagg ctggagtgca
2101 gtgcacaatc tcagctcact gcaacctctg cctctgggt tcaagtgatt cttgtgcatc
2161 agccacccaa gaagctggga ttaaaggcat gtgccactat gcccaccaaa tttttatttt
2221 tggtagagac agggtttcac catgttggcc aggctgatct tgaactctgg cctcaagtga
2281 tccatccatc tcagcctccc aaagtgctgg gattacaggt gtgagccacc atgccaggcc
2341 ctgatttttc ataagactaa aaattttgga aacagaagaa tgctaagata tagctgctaa
2401 agggcatgtt tgagatgcct accacttaat taagtgctgt gaagtaccta ggagtctctt
2461 gctagaaaag gaaggtgagg gtgtgagcaa agtcatccta ggctgtattc atctgaggcc
2521 aggagtattg gagcttattc aatagaggaa ttctcaaagt agctctggag cctccatctt
2581 agcctggtag gtaaagaact ctaggcgggt gatttttgct ctgactatgg tatattgaaa
2641 ataatttttt tttttgaaa tggagtcttg ctccgttgcc caggctggag tacagtggca
2701 tgagctcttg gctcactgca acctctaccc ggcctcccaa ccccccgccc cgggttcaag
2761 caattctcct tcctcagcct cccgagtagc taggattaca ggcgggcact accacgcccg
2821 gctaattttt gtattttgg tagagacagg gtttcaccat gtctctggtc atgtcaggat
2881 ggtctcaaac tcctgacctc aagtgatctg cctgccttgg cctcccaaag tgctggatt
2941 acaggcttga gccactgcct caggcccaat tgggaagaat ttaagggagg aactaaaagc
3001 tatgcatttt agttgggat agggaagaaa acattacagt ttatcagttg aaatttatc
3061 agatcagtgg tattactaga aactgtgtca catctagtta ctatagataa tttaggtctt
3121 gattgcctaa actctgattt ctagctctgg agtgcctagt tacaatactg aggaatggag
3181 atatacattg ccatcctttg gaagaatttt gaatttgaa tatttctcca tgaaccacat
3241 actaatatag aaggaagaat agacttttc ttttttctga gatagggact tgctttgtca
3301 cccaggctgg agtgcagtgg cacgatctca gcccactgca acctccgtcc cccaggctca
3361 gggatcgaag ctagagtggt ggcctgtttg gattcaggcc caggggccga gacattccct
3421 tcttcactct tttccggatc c
```

FIGURE 14A

```
LOCUS       AF024543    2598 bp    DNA              PRI      20-OCT-1997
DEFINITION  Homo sapiens MLL/AF4 translocation breakpoint t(4;11)(q21;q23).
ACCESSION   AF024543
VERSION     AF024543.1  GI:2547405
KEYWORDS
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 2598)
  AUTHORS   Megonigal,M.D., Rappaport,E.F., Jones,D.H., Kim,C.S., Nowell,P.C.,
            Lange,B.J. and Felix,C.A.
  TITLE     Panhandle PCR strategy to amplify MLL genomic breakpoints in
            treatment-related leukemias
  JOURNAL   Proc. Natl. Acad. Sci. U.S.A. 94 (21), 11583-11588 (1997)
  MEDLINE   97471010
REFERENCE   2  (bases 1 to 2598)
  AUTHORS   Megonigal,M.D., Rappaport,E.F. and Felix,C.A.
  TITLE     Direct Submission
  JOURNAL   Submitted (10-SEP-1997) Pediatrics, Joseph Stokes, Jr. Research
            Institute, Children's Hospital of Philadelphia, University of
            Pennsylvania School of Medicine, Leonard and Madlyn Abramson
            Pediatric Research Center, Rm. 902B, Children's Hospital of
            Philadelphia, 324 South 34th Street, Philadelphia, PA 19104, USA
FEATURES             Location/Qualifiers
     source          1..2598
                     /organism="Homo sapiens"
                     /db_xref="taxon:9606"
                     /chromosome="4, 11"
                     /map="t(4;11)(q21;q23)"
                     /sub_clone="plasmid subclone 38-1"
                     /clone_lib="panhandle PCR products containing genomic
                     t(4;11)(q21;q23) der 11 translocation breakpoint in
                     treatment-related ALL involving MLL and AF-4"
                     /note="4q21, D4S1542"
BASE COUNT        734 a    553 c    632 g    679 t
ORIGIN
        1 ggatccgtgg tcatcccgcc tcagccacct actacaggac cgccaagaaa agaagttccc
       61 aaaaccactc ctagtgagcc caagaaaaag cagcctccac caccagaatc aggtgagtga
      121 ggagggcaag aaggaattgc tgaaccacaa gtactaacaa aaaagcactg atgtctcaaa
      181 cagcatttga aagcaggaaa tgtatgattt gaagtcttca gttcaagaaa atcagctctc
      241 tttctaacta ttatgtttaa taataagaa acagaaacaa aaaaaacagt taaattggag
      301 gtattgtttt aatttcctgt tcgaagccta gagtttaaat agtttttttt tttttttcta
      361 atggcccttt cttcacaggt cagtcagtac taaagtagtc gttgccagca tctgactgca
      421 atttattctg aatttttag gtccagggca gagcaaacag aaaaaagtgg ctccccgccc
      481 aagtatccct gtaaaacaaa accaaaaga aaggtgagg agagatttgt ttctctgcca
      541 tttctcaggg atgtattcta ttttgtaggg aaaagcctta tccttgactt ctatgtagat
      601 ggcagtggaa tttcttaaaa ttaagaaact tcaagtttag gcttttagct gggcacggtg
      661 gctcatgctg gtaatcccaa cacttattga ggctgaggtg ggaggattgc ttgaggccag
      721 cagttcaaga ccagcctggg caacatagca agacctgtc tttatttaaa ccaaaaaaaa
      781 aaaaagaaga agaagaagaa gttagccagg catggtggca gttgcgtgta gtcccaggta
      841 ctcaggaggc tgagatagaa ggattgtctt gagcccagga attcaaggct gtagtgagct
      901 atgattgtac cactgcagtc cagcctgggt gacaaagcaa aacactgtct ccaaaaaaaa
```

FIGURE 14B

```
 961 tttaggcttg gcaaggcgca gcggctcacg cctgtgatcc cagcactttg ggaagccgaa
1021 gcaggcagat cacttgaggt caggagttgg agaccagcct ggccaacatg gtgaaaccct
1081 gtctctactg aaaatacaaa aattagccgg ttgtggtagt gggtgcttgt aatcctagct
1141 acttgggagg ctgaggcagg ggaattgcct gaacctgcga ggcggaggct gcagtgagcc
1201 gagattgcat cattgcactc tagcctggac aacagagcta gactccatcc caaaaaaaaa
1261 aagtagccgg gcacggtggc tcacgcctgt aatcccagca ctttgggagg ccgaggcggg
1321 cggatcatga gggcaggaga tcgagaccat cctggctaac acggtgaaac cctgtctcta
1381 ctaaaaatac aaaaaattag cccggcgagg tggcgggcgc ctgtagtccc agctactcag
1441 gagagtgagg caggagaatg gcgtgaaccc gggggggcgga gcctgcagtg agccgagatc
1501 gcgccactgc actccagctt gggtgacacc gagactccgt ctcaaaaaaa aataaaaagt
1561 ttaggcttta gcctgtttct ttttggttt cttccttgtt gcttttccct tctttgtggc
1621 cccacatgtt ctagcctagg aatctgctta ttctaaaggc catttggcgt aattattttt
1681 tgacccccaac atcctttagc aattatttgt ctgtaaaaat caccccttccc tgtattcact
1741 attttttattt attatggata aagagatagt gtggtggctc acatctataa tcccagcact
1801 ttggggggcc aaggcgggag gatcacttga gggcaggagc tggagaccag cctgggcagc
1861 acagtgacac acagttgcta taaaaaattt aaaaatcaac taggcatggt ggcatgcacc
1921 tgtagtccca gctactcttg agaagctgag gcaggaggat cacgagccca caaggtctag
1981 gctgcagtga gctgtgactg tggcaatctt tagagtttct ctctctcacc cgggctggaa
2041 tgcagtagca cgatcacagc tcacttcagc cttgaactcc tgggtccaag caatgcccac
2101 ttttccatcc tgagtagcta ggactgcagg cacatggcag catgcttggc tgatttattt
2161 ttatttttg tagagacaag gtcttggggt gttgcccagg ctgaacctgg caatcttatg
2221 aagaaacact ttaaactctg aaggaaactt tttaagtaat atagacacaa tattttttgaa
2281 aagctcttaa attgctaaaa attaatgcaa agaatagaat tgcttatagt agcccaagag
2341 gaaagcataa aattgaaact ggaagaactt tttgggtggt attaattgga gttgttttta
2401 ctttgtgcat ttcactttct attccttctc ggaaatgcca gaagtacatt tgctaccagg
2461 atgagaaatt cctgttcctc cttgttttca cacttgagat gtttgtggat ggttattgga
2521 tcggaagctg gagtggtggc ctgtttggat tcaggcccag gggccgagac attcccttct
2581 tcactctttt ccggatcc
```

METHODS AND KITS FOR ANALYSIS OF CHROMOSOMAL REARRANGEMENTS ASSOCIATED WITH LEUKEMIA

CROSS REFERENCE TO RELATED APPLICATIONS

This application claims priority pursuant to 35 U.S.C. §119(e) to each of the following provisional patent applications: U.S. Application No. 60/038,624, filed Feb. 19, 1997, U.S. Application No. 60/056,938, filed Aug. 25, 1997, and U.S. Application No. 60/065,911, filed Nov. 17, 1997.

STATEMENT REGARDING FEDERALLY SUPPORTED RESEARCH AND DEVELOPMENT

The invention was supported in part by funds from the U.S. Government (National Institutes of Health Grant No. 1R29CA66140-02), and the U.S. Government may therefore have certain rights in the invention.

FIELD OF THE INVENTION

The field of the invention is diagnosis of and therapy for leukemia.

BACKGROUND OF THE INVENTION

Leukemias including, but not limited to, acute leukemias such as acute lymphoblastic leukemia (ALL) and acute myeloid leukemia (AML) are among the most common malignancies in children. Myelodysplastic syndrome is a designation for a group of syndromes similar to preleukemia (see, e.g. *The Merck Manual,* 16th ed., Berkow et al., Eds., Merck Research Laboratories, Rahway, N.J., pp. 1243–1245). Leukemias are also a serious cause of morbidity and mortality among adult humans, although MLL gene translocations are present in perhaps only a small proportion of adult acute leukemias. The incidences of ALL and AML in the United States are, respectively, 20 and 10.6 per million individuals per year in infants less than one year old. The aggressiveness with which a leukemia is treated depends, in part, on whether the leukemia has as its genesis a rearrangement of a portion of a chromosome at one or more particular sites. Some translocations may be detected by karyotype analysis, and others cannot be detected by such analysis.

Translocation of the MLL gene (which is alternately designated ALL-1, Htrx1, or HRX) at chromosome band 11q23 is associated with most cases of ALL which occur during infancy and with most monoblastic variants of AML which occur during the first four years of life (Cimino et al., 1993, Blood 82:544–546; Pui et al., 1995, Leukemia 9:762–769; Hilden et al., 1995, Blood 86:3876–3882; Chen et al., 1993, Blood 81:2386–2393; Martinez-Climent et al., 1993, Leukemia 9:1299–1304). About five percent of de novo cases of adult acute leukemia and most DNA topoisomerase II inhibitor-related leukemias are associated with similar translocations (Pui et al., 1995, supra; Martinez-Climent et al., 1993, supra; Raimondi, 1993, Blood 81:2237–2251; Felix et al., 1995, supra).

The MLL gene is 90 kilobases long, comprises 36 exons, and encodes a 3969 amino acid residue protein (Rasio et al., 1996, Cancer Res. 56:1766–1769). The MLL gene is believed to be involved in hematopoiesis and leukemogenesis. The MLL gene product contains several structural motifs important in the regulation of transcription (Domer et al., 1993, Proc. Natl. Acad. Sci. USA 90:7884–7888; Djabali et al., 1992, Nature Genet. 2:113–118; Gu et al., 1992, Cell 71:701–708; Tkachuk et al., 1992, Cell 71:691–700; Ma et al., 1993, Proc. Natl. Acad. Sci. USA 90:6350–6354) and functions as a positive regulator of Hox gene expression (Yu et al., 1995, Nature 378:505–508). Translocation of the MLL gene at chromosome band 11q23 disrupts an 8.3 kilobase breakpoint cluster region (bcr) which is interposed between exons 5 and 11 of MLL. Approximately thirty different translocation partner genes of MLL have been recognized (Martinez-Climent et al., 1993, supra; Raimondi, Blood 81:2237–2251; Felix et al., 1995, Blood 85:3250–3256). Many of these partner genes have not been cloned or characterized.

MLL gene translocations may be detected by karyotype analysis as terminal 11q23 deletions (Shannon et al., 1993, Genes Chromosomes Cancer 7:204–208; Prasad et al., 1993, Cancer Res. 53:5624–5628; Yamamoto et al., 1994, Blood 83:2912–2921). About one third of ALL cases are associated with MLL rearrangements that cannot be detected by karyotype analysis. (Sorenson et al., 1992, Blood 80:255a; Schichman et al., 1994, Proc. Natl. Acad. Sci. USA 91:6236–6239; Schichman et al., 1994, Cancer Res. 54:4277–4280).

Sites of chromosome rearrangement (hereinafter, "breakpoint regions") have been localized to introns within the bcr of MLL in several de novo cases of leukemia (Gu et al., 1992, Proc. Natl. Acad. Sci. USA 89:10464–10468; Negrini et al., 1993, Cancer Res. 53:4489–4492; Domer et al., 1993, Proc. Natl. Acad. Sci. USA 90:7884–7888; Corral et al., 1993, Proc. Natl. Acad. Sci. USA 90:8538–8542; Gu et al., 1994, Cancer Res. 54:2327–2330). The location of breakpoint regions within MLL and the identity of the nucleotide sequences located at such breakpoint regions are believed to vary according to etiology and pathogenesis of the leukemia. Fewer than half of the about thirty known MLL translocation partner genes have been cloned and identified, although for many of these partner genes, only partial or cDNA sequences are known.

One determinant of the location of a breakpoint region may be the nucleotide sequence preference attributable to either DNA topoisomerase II or a complex comprising DNA topoisomerase II and an agent which interacts with DNA topoisomerase II (Liu et al., 1991, In: *DNA Topoisomerases in Cancer,* Oxford University Press, New York, pp. 13–22; Ross et al., 1988, In: *Important Advances in Oncology,* pp. 65–79; Pommier et al., 1991, Nucl. Acids Res. 19:5973–5980; Pommier, 1993, Cancer Chemother. Pharmacol. 32:103–108). For example, epipodophyllotoxins form a complex with DNA and DNA topoisomerase II, whereby chromosomal breakage can be effected at the site of complex formation (Corbett et al., 1993, Chem. Res. Toxicol. 6:585–597). Epipodophyllotoxins and other DNA topoisomerase II inhibitors have been associated with leukemias characterized by heterogenous translocations throughout the bcr of MLL at chromosome band 11q23 (Pui et al., 1991, N. Engl. J. Med. 325:1682–1687; Pui et al., 1990 Lancet 336:417–421; Winick et al., J. Clin. Oncol. 11:209–217; Broeker et al., 1996, Blood 87:1912–1922; Felix et al., 1993, Cancer Res. 53:2954–2956; Felix et al., 1995, Blood, 85:3250–3256; Pedersen-Bjergaard, 1992, Leukemia Res. 16:61–65; Pedersen-Bjergaard, 1991, Blood 78:1147–1148).

DNA topoisomerase II catalyzes transient double-strand breakage and religation of genomic DNA, and is involved in regulating DNA topology by relaxation of supercoiled genomic DNA. It is believed that agents which interact with DNA topoisomerase II and which are associated with leukemias inhibit the ability of DNA topoisomerase II to catalyze religation following double-strand breakage. One suggested model for translocations involving MLL entails DNA topoisomerase II-mediated chromosome breakage within the bcr, followed by fusion of DNA free ends from different chromosomes mediated by cellular DNA repair mechanisms (Felix et al., 1995, Cancer Res. 55:4287–4292). Although not strictly inhibitors in the enzymatic sense, epipodophyllotoxins are designated DNA topoisomerase II inhibitors because they decrease the rate of chromosomal religation catalyzed by DNA topoisomerase II and stabilize the DNA topoisomerase II-DNA covalent intermediate (Chen et al., 1994, Annu. Rev. Pharmacol. Toxicol. 84:191–218; Osheroff, 1989, Biochemistry 28:6157–6160; Chen et al., 1984, J. Biol. Chem. 259:13560–13566; Wang et al., 1990, Cell 62:403–406; Long et al., 1985, Cancer Res. 45:3106–3112; Epstein, 1988, Lancet 1:521–524; Osheroff et al., 1991, In: *DNA Topoisomerases in Cancer*, Potmesil et al., Eds., Oxford University Press, New York, pp. 230–239).

Chromatin structure and scaffold attachment regions may also affect the location of a breakpoint within bcr (Broeker et al., 1996, Blood 87:1912–1922).

Abasic sites are produced by oxidative DNA damage, ionizing radiation, alkylating agents, and spontaneous DNA hydrolysis (Kingma et al., 1995, J. Biol. Chem. 270:21441–21444). Abasic sites are the most common form of spontaneous DNA damage. Abasic sites resulting from exposure to environmental toxins or spontaneous abasic sites may be important mediators of leukemogenesis and provide another explanation of how chromosomal breakage is initiated in leukemia in infants (Kingma et al., 1997, Biochemistry 36:5934–5939), because abasic sites increase DNA topoisomerase II-mediated breakage.

Panhandle PCR methods have been described, and can be used to amplify genomic DNA having a nucleotide sequence comprising a known sequence which flanks an unknown sequence located 3' with respect to the known sequence (Jones et al., 1993, PCR Meth. Applicat. 2:197–203; U.S. Pat. No. 5,411,875). The panhandle PCR methods comprise generation of a single-stranded DNA having a sequence comprising a region of known sequence at the 5'-end of the single-stranded DNA followed by a region of unknown sequence and having a region complementary to known region DNA at the 3'-end of the single-stranded DNA. The complementary region is complementary to a portion of DNA within the region of known sequence. Thus, the template comprises regions at each end having known sequences. Using primers complementary to each of these regions, the section of the template comprising region of unknown sequence may be amplified, and the nucleotide sequence of this section may be determined. Panhandle PCR has not been used to identify translocation breakpoints or to clone translocation partner genes.

There remains a need for a method of identifying and characterizing MLL rearrangement in individual patients afflicted with leukemia. Identification and characterization of such a rearrangement in the genome of a patient indicates the type and aggressiveness of therapy which may be provided to the patient to treat the leukemia and symptoms associated therewith. The present invention provides such a method.

BRIEF SUMMARY OF THE INVENTION

The invention includes a method of amplifying an unknown region which flanks a known region of a leukemia-associated DNA sequence. The method comprises (a) providing a template polynucleotide comprising a sense strand which comprises the known region and the unknown region, wherein the unknown region is nearer the 3'-end of the sense strand than is the known region, wherein the known region comprises a first portion and a second portion, and wherein the first portion is nearer the unknown region than is the second portion; (b) ligating a loop-forming oligonucleotide to the 3'-end of the sense strand, wherein the loop-forming oligonucleotide is complementary to the first portion; (c) annealing the loop-forming oligonucleotide with the first portion to generate a panhandle structure; (d) subjecting the panhandle structure to extension, whereby an additional region complementary to the second portion is generated at the free end of the loop-forming oligonucleotide; and (e) subjecting the panhandle structure to PCR in the presence of a first primer homologous with the second portion, whereby the unknown region is amplified.

In one aspect, the leukemia-associated DNA sequence comprises MLL.

In a preferred embodiment, the known region comprises a portion of the breakpoint cluster region of MLL.

In another preferred embodiment, the known region comprises a portion of an exon of MLL selected from the group consisting of exon 5 and exon 11.

In another aspect, the loop-forming oligonucleotide has a nucleotide sequence comprising SEQ ID NO: 4.

In yet another aspect, the first primer has a nucleotide sequence selected from the group consisting of SEQ ID NO: 5–8.

In yet a further aspect, the panhandle structure is subjected to PCR in the presence of the first primer and further in the presence of a second primer, wherein the second primer is nested with respect to the first primer.

In a preferred embodiment, each of the first primer and the second primer independently has a nucleotide sequence selected from the group consisting of SEQ ID NO: 5–8.

In another aspect, the template polynucleotide further comprises an antisense strand, wherein the 5'-end of the antisense strand overhangs the 3'-end of the sense strand, and wherein a portion of the loop-forming oligonucleotide is complementary to the overhanging region of the antisense strand.

In yet another aspect, the template polynucleotide is provided by obtaining genomic DNA from a patient; contacting the genomic DNA with a restriction endonuclease, whereby a genomic DNA fragment is generated, the genomic DNA fragment comprising the known region and the unknown region, whereby the genomic DNA is the template polynucleotide.

The invention also includes a variant method of amplifying an unknown region which flanks a known region of a leukemia-associated DNA sequence. This method comprises (a) providing a template polynucleotide comprising an antisense strand which comprises a region complementary to the known region and a region complementary to the unknown region, wherein the region complementary to the unknown region is nearer the 5'-end of the antisense strand than is the region complementary to the known region, wherein the known region comprises a first portion and a second portion, and wherein the first portion is nearer the unknown region than is the second portion; (b) ligating a first oligonucleotide to the 5'-end of the antisense strand, wherein the first oligonucleotide is homologous with the first portion; (c) annealing a pre-template polynucleotide with the antisense strand, the pre-template polynucleotide being homologous with the second portion; (d) subjecting the pre-template polynucleotide to extension, whereby a sense strand is generated, the sense strand comprising the known region, the unknown region, and a loop-forming oligonucleotide at the 3'-end thereof, the loop-forming oligonucleotide being complementary to the first portion; (e) annealing the loop-forming oligonucleotide with the first portion to generate a panhandle structure; (f) subjecting the panhandle structure to extension, whereby an additional region complementary to the second portion is generated at the free end of the loop-forming oligonucleotide; and (g) subjecting the panhandle structure to PCR in the presence of a first primer homologous with the second portion, whereby the unknown region is amplified.

In one aspect of this aspect of the invention, prior to ligating the first oligonucleotide to the antisense strand, a bridging oligonucleotide is annealed with a portion of the antisense strand adjacent the 5'-end thereof and the first oligonucleotide is annealed with the bridging oligonucleotide.

Also included in the invention is a method of identifying a translocation partner of a leukemia-associated DNA sequence, the translocation partner comprising an unknown region, and the leukemia-associated DNA sequence comprising a known region. This method comprises (a) providing a template polynucleotide comprising a sense strand which comprises the known region and the unknown region, wherein the unknown region is nearer the 3'-end of the sense strand than is the known region, wherein the known region comprises a first portion and a second portion, and wherein the first portion is nearer the unknown region than is the second portion; (b) ligating a loop-forming oligonucleotide to the 3'-end of the sense strand, wherein the loop-forming oligonucleotide is complementary to the first portion; (c) annealing the loop-forming oligonucleotide with the first portion to generate a panhandle structure; (d) subjecting the panhandle structure to extension, whereby an additional region complementary to the second portion is generated at the free end of the loop-forming oligonucleotide; (e) subjecting the panhandle structure to PCR in the presence of a first primer homologous with the second portion, whereby the unknown region is amplified; and (f) identifying a portion of a human DNA sequence homologous with the unknown region, whereby the human DNA sequence is identified as the translocation partner.

The invention further includes a variant method of identifying a translocation partner of a leukemia-associated DNA sequence, the translocation partner comprising an unknown region, and the DNA sequence comprising a known region. This method comprises (a) providing a template polynucleotide comprising an antisense strand which comprises a region complementary to the known region and a region complementary to the unknown region, wherein the region complementary to the unknown region is nearer the 5'-end of the antisense strand than is the region complementary to the known region, wherein the known region comprises a first portion and a second portion, and wherein the first portion is nearer the unknown region than is the second portion; (b) ligating a first oligonucleotide to the 5'-end of the antisense strand, wherein the first oligonucleotide is homologous with the first portion; (c) annealing a pre-template polynucleotide with the antisense strand, the pre-template polynucleotide being homologous with the second portion; (d) subjecting the pre-template polynucleotide to extension, whereby a sense strand is generated, the sense strand comprising the known region, the unknown region, and a loop-forming oligonucleotide at the 3'-end thereof, the loop-forming oligonucleotide being complementary to the first portion; (e) annealing the loop-forming oligonucleotide with the first portion to generate a panhandle structure; (f) subjecting the panhandle structure to extension, whereby an additional region complementary to the second portion is generated at the free end of the loop-forming oligonucleotide; (g) subjecting the panhandle structure to PCR in the presence of a first primer homologous with the second portion, whereby the unknown region is amplified; and (h) identifying a portion of a human DNA sequence homologous with the unknown region, whereby the human DNA sequence is identified as the translocation partner.

Also included in the invention is a kit for panhandle PCR amplification of an unknown region of DNA which flanks a known region of the sense strand of a leukemia-associated DNA sequence. The kit comprises an oligonucleotide selected from the group consisting of an oligonucleotide which is complementary to the known region of the sense strand and an oligonucleotide which is homologous with the known region of the sense strand; and a first primer homologous with the known region of the sense strand.

In one aspect, the kit further comprises an internal primer, wherein the internal primer is nested with respect to the first primer, and wherein the internal primer is selected from the group consisting of a primer homologous with the known region of the sense strand.

In another aspect, the kit further comprises at least one recombination PCR primer.

In yet another aspect, the kit further comprises a restriction endonuclease; at least one reagent for ligating the oligonucleotide to a DNA strand obtained from a human patient; at least one reagent for extending a polynucleotide; and at least one reagent for performing PCR.

The invention also includes an isolated polynucleotide having a nucleotide sequence which comprises a sequence selected from the group consisting of SEQ ID NOs: 1–3.

In addition, the invention includes a primer derived from an isolated polynucleotide having a nucleotide sequence which comprises a sequence selected from the group consisting of SEQ ID NOs: 1–3.

BRIEF DESCRIPTION OF THE DRAWINGS

FIG. 2 is a diagram of a 'variant' panhandle PCR method described herein.

FIGS. 4A–4D is the nucleotide sequence of a translocation breakpoint region described herein in Example 1 (SEQ ID NO: 23).

FIGS. 5A–5C is a preliminary nucleotide sequence of a portion of the gene sequence obtained from the unknown region of the amplified polynucleotide product derived from the infant patient described in Example 1 (SEQ ID NO: 1).

FIGS. 6A–6B is a preliminary antisense sequence corresponding to the nucleotide sequence in FIG. 5 (SEQ ID NO: 2).

FIGS. 7A–7D is a preliminary conglomerate nucleotide sequence of the translocation breakpoint region described herein in Example 1 (SEQ ID NO: 3).

FIG. 11 is a nucleotide sequence of a breakpoint junction of a partial duplication described in Examples 2 and 3 (SEQ ID NO: 15).

FIG. 12 is a nucleotide sequence of a translocation breakpoint junction described in Examples 2 and 3 (SEQ ID NO: 16).

FIGS. 13A–13B is a nucleotide sequence of a breakpoint junction of a partial duplication described in Examples 2 and 3 (SEQ ID NO: 17).

FIGS. 14A–14B is a nucleotide sequence of a translocation breakpoint junction described in Examples 2 and 3 (SEQ ID NO: 18).

DETAILED DESCRIPTION OF THE INVENTION

Figure 1A:
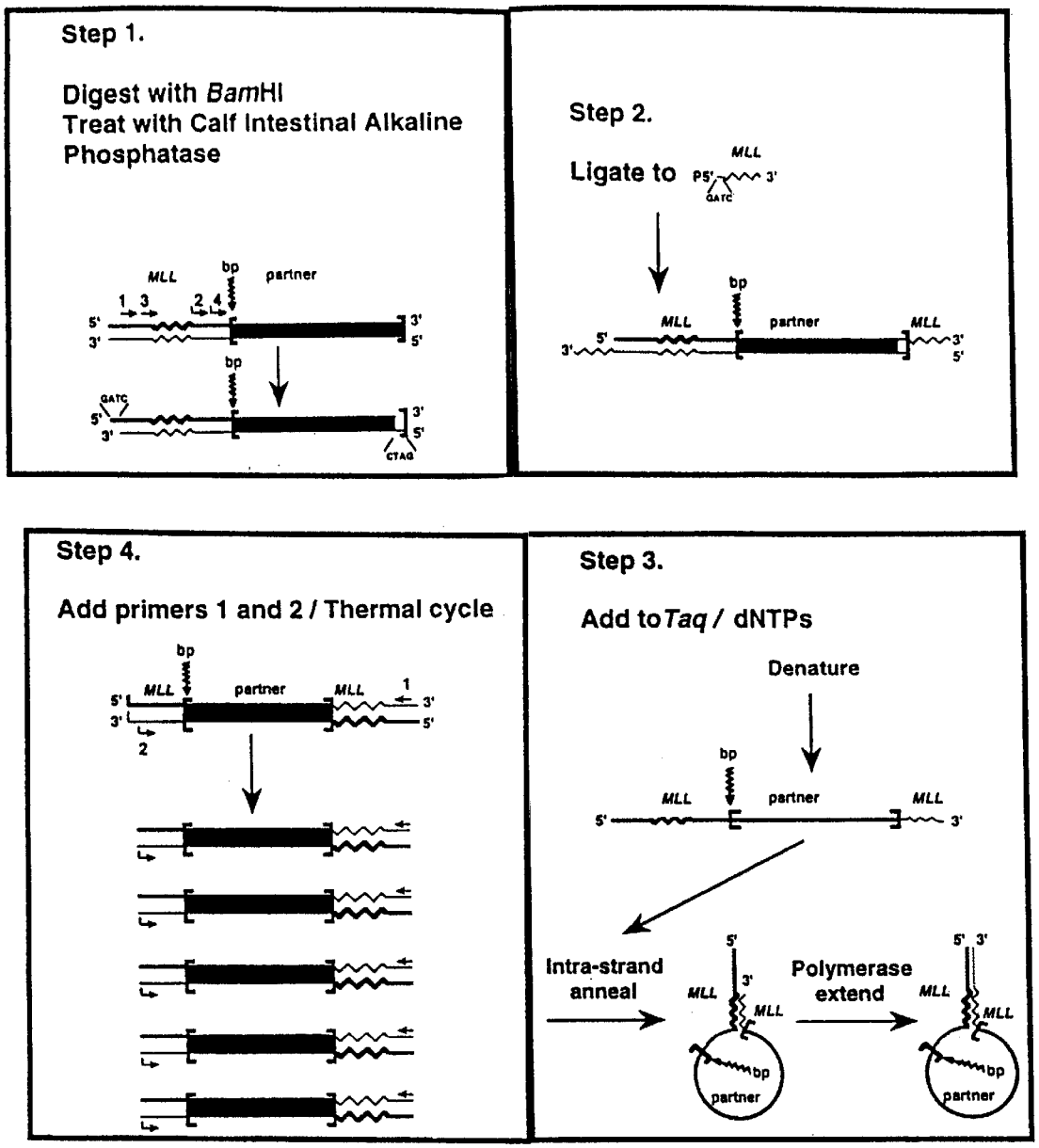
FIGS. 1A and 1B is a diagram of a 'basic' panhandle PCR method described herein.

The invention relates to kits and methods for panhandle PCR amplification of a region of DNA having an unknown nucleotide sequence, wherein the region flanks a region of a leukemia-associated gene having a known nucleotide sequence in the DNA of a human patient. Two different panhandle PCR methods have been discovered. Amplification of an unknown region flanking a known region of a leukemia-associated gene permits identification of a translocation partner of the gene or identification of a duplicated sequence within the gene. Identification of the translocation partner or the duplicated sequence permits a medical practitioner to predict the course of a leukemia associated with the presence of the translocation partner or the duplicated sequence, and further permits the practitioner to determine the aggressiveness of anti-leukemia therapy that will be required. The invention further relates to kits useful for performing the methods of the invention.

Definitions

As used herein, the following terms have the meanings described in the present application.

The "bcr" region of MLL means the breakpoint cluster region of the MLL gene, an approximately 8.3-kilobase region of the gene which extends from a BamHI cleavage site of the sense strand of MLL exon 5 to another BamHI cleavage site of the sense strand of MLL exon 11. The sequence of the bcr of MLL is known (GenBank Accession # HSU04737). Where nucleotide residues are numbered within the bcr, they are numbered from the 5'-end of the sense strand of the bcr of MLL. Where breakpoints are identified within the bcr of MLL, the location of the breakpoint refers to the nucleotide residue located immediately 5' of the site of breakage (i.e. the 3'-most residue of wild type MLL sequence following the translocation event).

A first region of a polynucleotide "flanks" a second region of the polynucleotide if the two regions are adjacent to one another, or if the two regions are separated by no more than about 1000 nucleotide residues, and preferably by no more than about 100 nucleotide residues.

A first region of a polynucleotide is "adjacent" to a second region of the polynucleotide if the two regions are attached to or positioned next to one another, having no intervening nucleotides. By way of example, the pentanucleotide region 5'-AAAAA-3' is adjacent to the trinucleotide region 5'-TTT-3' when the two are connected thus: 5'-AAAAATTT-3' or 5'-TTTAAAAA-3', but not when the two are connected thus: 5'-AAAAACTTT-3'.

"Complementary" refers to the broad concept of subunit sequence complementarity between regions of two polynucleotides or between two regions of the same polynucleotide. It is known that an adenine residue of a first polynucleotide region is capable of forming specific hydrogen bonds ("base pairing") with a residue of a second polynucleotide region which is antiparallel to the first region if the residue is thymine or uracil. Similarly, it is known that a cytosine residue of a first polynucleotide region is capable of base pairing with a residue of a second polynucleotide region which is antiparallel to the first region if the residue is guanine. A first region of a polynucleotide is complementary to a second region of the same or a different polynucleotide if, when the two regions are arranged in an antiparallel fashion, at least three nucleotide residues of the first region is capable of base pairing with three residues of the second region. Preferably, the first region comprises a first portion and the second region comprises a second portion, whereby, when the first and second portions are arranged in an antiparallel fashion, at least about 30%, and preferably at least about 75%, at least about 90%, or at least about 95% of the nucleotide residues of the first portion are capable of base pairing with nucleotide residues in the second portion. Such portions are said to exhibit 30%, 75%, 90%, and 95% complementarity, respectively. More preferably, all nucleotide residues of the first portion are capable of base pairing with nucleotide residues in the second portion (i.e. the first and second portions exhibit 100% complementarity).

A first polynucleotide region and a second polynucleotide region are "arranged in an antiparallel fashion" if, when the first region is fixed in space and extends in a direction from its 5'-end to its 3'-end, at least a portion of the second region lies parallel to the first region and extends in the same direction from its 3'-end to its 5'-end.

"Homologous" as used herein, refers to nucleotide sequence identity between two regions of the same polynucleotide or between regions of two different polynucleotides. When a nucleotide residue position in both regions is occupied by the same nucleotide residue, then the regions are homologous at that position. A first region is homologous to a second region if at least three nucleotide residue positions of each region are occupied by identical nucleotide residues. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' are 50% homologous. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. Such portions are said to exhibit 50%, 75%, 90%, and 95% homology, respectively More preferably, all nucleotide residue positions of each of the portions are occupied by the same nucleotide residue (i.e. the first and second portions exhibit 100% homologous).

A "leukemia-associated DNA sequence" means a DNA sequence of a human patient wherein translocation of genomic DNA into the DNA sequence or rearrangement of the DNA sequence is associated with onset, continuation, or relapse of leukemia in the patient. Leukemia-associated DNA sequences include, but are not limited to, genes, such as MLL, which are associated with onset, continuation, or relapse of acute leukemia. It is understood that changes in a leukemia-associated DNA sequence, such as a chromosomal translocation for example, may occur in a preleukemia phase before leukemia is clinically detected.

A "region" and a "portion" of a polynucleotide are used interchangeably to mean a plurality of sequential nucleotide residues of the polynucleotide.

A "polynucleotide" means a single strand or parallel and anti-parallel strands of a nucleic acid. Thus, a polynucleotide may be either a single-stranded or a double-stranded nucleic acid.

An "oligonucleotide" means a nucleic acid comprising at least two nucleotide residues.

A first polynucleotide is "ligated" to a second polynucleotide if an end of the first polynucleotide is covalently bonded to an end of the second polynucleotide.

By way of example, the covalent bond may be a phosphodiester bond. "Extending" a polynucleotide means the addition of nucleotide residues to an end of the polynucleotide, wherein the added nucleotide residues are complementary to nucleotide residues of a region of either the same or a different polynucleotide with which the polynucleotide is annealed. Extension of a polynucleotide typically occurs by template-directed polymerization or by template-directed ligation.

A first polynucleotide is "annealed" with a second polynucleotide when the two polynucleotides are arranged in an anti-parallel fashion and when at least three nucleotide residues of the first polynucleotide are base paired with a nucleotide residue of the second polynucleotide.

A "panhandle structure" is a polynucleotide comprising a first region and a second region, wherein when the first region and the second region are separated by at least several nucleotide residues and are annealed to each other in an anti-parallel fashion. The first and second regions may be separated by several hundred or even by several thousand nucleotide residues.

A "primer" is an oligonucleotide which can be extended when annealed with a complementary region of a nucleic acid strand.

"Amplification of a region of a polynucleotide" means production of a plurality of nucleic acid strands comprising the region.

A "product" of an amplification reaction such as PCR means an polynucleotide generated by extension of a primer used in the amplification reaction.

A first polynucleotide comprises an "overhanging region" if it has a double-stranded portion wherein either the 3'-end or the 5'-end of a strand of the polynucleotide extends beyond the 5'-end or the 3'-end, respectively, of the same or a different strand of the polynucleotide. By way of example, the 5'-end of an antisense strand overhangs the 3'-end of a sense strand with which it is annealed if the 5'-end of the antisense strand extends beyond the 3'-end of the sense strand.

A "genomic DNA" of a human patient is a DNA strand which has a nucleotide sequence homologous with or complementary to a portion of a chromosome of the patient. Included in this definition for the purposes of simplicity are both a fragment of a chromosome and a cDNA derived by reverse transcription of a human RNA.

A "translocation partner" of a human gene is a region of genomic DNA which does not normally flank the gene, but which flanks the gene following a translocation event.

A "translocation event" means fusion of a first region of a human chromosome with a second region of a human chromosome, wherein the first region and the second region are not normally fused. By way of example, breakage of a first and a second human chromosome and fusion of a part of the first chromosome with a part of the second chromosome is a translocation event. For the sake of simplicity, tandem duplications are herein included within the definition of translocation event, it being understood that tandem duplications and translocations occur by similar mechanisms of DNA recombination.

A polynucleotide is "derived from" a gene if the polynucleotide has a nucleotide sequence which is either homologous with or complementary to a portion of the nucleotide sequence of the gene.

A first polynucleotide anneals with a second polynucleotide "with high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g. Sambrook et al., 1989, *Molecular Cloning: A Laboratory Manual*, Cold Spring Harbor Laboratory, New York).

A third primer is "nested" with respect to a first primer and a second primer if amplification of a region of a first polynucleotide using the first primer and the second primer yields a second polynucleotide, wherein the third primer is complementary to an internal portion of the second polynucleotide, wherein the internal portion of the second polynucleotide to which it is complementary does not include a nucleotide residue at the corresponding end of the second polynucleotide.

A second primer is "nested" with respect to a first primer if amplification of a region of a first polynucleotide using the first primer yields a second polynucleotide, wherein the second primer is complementary to an internal portion of the second polynucleotide, and wherein the internal portion of the second polynucleotide to which the second primer is complementary does not include a nucleotide residue at the corresponding end of the second polynucleotide.

A portion of a polynucleotide is "near" the end of a region of the polynucleotide if at least one nucleotide residue of the portion is separated from the end of the region by no more than about one hundred nucleotide residues, and preferably by no more than about twenty-five nucleotide residues.

A restriction site is a portion of a polynucleotide which is recognized by a restriction endonuclease.

A portion of a polynucleotide is "recognized" by a restriction endonuclease if the endonuclease is capable of cleaving a strand of the polynucleotide at a fixed position with respect to the portion of the polynucleotide.

A strand of a polynucleotide is the "sense" strand with respect to unknown flanking DNA if the nucleotide sequence of a first portion of the strand is known, if the nucleotide sequence of a second portion of the strand is unknown, and if the first portion is located 5' with respect to the second portion.

Description

The invention includes a 'basic' panhandle PCR method and a 'variant' panhandle PCR method. Either of the basic panhandle PCR method of the invention or the variant panhandle PCR method of the invention can be used to amplify an unknown region which flanks a known region of a leukemia-associated gene or to identify a translocation partner of such a gene.

Basic Panhandle PCR Method

The basic panhandle PCR method of the invention can be used to amplify an unknown region which flanks a known region of a leukemia-associated DNA sequence as follows.

A template polynucleotide is provided, the template polynucleotide comprising a sense strand which comprises the known region of a leukemia-associated DNA sequence and an unknown region which flanks the DNA sequence. The unknown region is nearer the 3'-end of the sense strand of the template polynucleotide than is the known region of the DNA sequence. Two portions of the known region of the DNA sequence are designated a first portion and a second portion, the first portion being nearer the unknown region than is the second portion. The template polynucleotide preferably comprises a known region of at least about twenty nucleotides. The leukemia-associated DNA sequence is preferably MLL. The known region may be, for example, a portion of the breakpoint cluster region of MLL, a portion of MLL which flanks the breakpoint cluster region of MLL, a portion of an exon of MLL such as a portion of exon 5 or a portion of exon 11, or a portion of an intron of MLL.

The template polynucleotide may be provided in the form of single-stranded or double-stranded DNA. When the template polynucleotide is double-stranded DNA, the 5'-end of the antisense strand may overhang the 3'-end of the sense strand. The method used to obtain the template polynucleotide is not critical. Many methods are known for generating or isolating DNA suitable for use as template DNA. By way of example, the template polynucleotide may be provided by obtaining genomic DNA from a patient, contacting the genomic DNA with a restriction endonuclease, whereby a genomic DNA fragment is generated, the genomic DNA fragment comprising the known region. This fragment may be used as the template polynucleotide.

A loop-forming oligonucleotide is ligated to the 3'-end of the sense strand of the template polynucleotide, the loop-forming oligonucleotide being complementary to the first portion of the known region of the DNA sequence. After ligating the loop-forming oligonucleotide to the template polynucleotide, the unknown region is flanked on one side by the loop-forming oligonucleotide and on the other side by the known region of the gene. The loop-forming oligonucleotide is then annealed with the first portion of the known region to generate a panhandle structure. When the template polynucleotide is provided in the form of double-stranded DNA, ligation of the loop-forming oligonucleotide to the sense strand of the template polynucleotide may be more easily achieved if the overhanging portion of the antisense strand of the template polynucleotide is complementary to one or more nucleotide residues at the 5'-end of the loop-forming oligonucleotide. Furthermore, it is necessary to denature a double-stranded template polynucleotide prior to annealing the loop-forming oligonucleotide with the first portion of the known region.

In the panhandle structure, the known region of the leukemia-associated DNA sequence and the loop-forming oligonucleotide form a "handle" region" of duplex DNA, and the unknown region is located in a single-strand "pan" region of the structure which is bounded on each end by one of the two DNA strands of the "handle" region. If the panhandle structure is subjected to extension, then a third region, complementary to the second portion is attached to the free end of the loop-forming oligonucleotide, such that the double-stranded "handle" portion of the panhandle structure further comprises the second portion of the known region of the DNA sequence and its complement. Thus, a DNA strand having known nucleotide sequences at each end and the unknown region therebetween is generated.

The DNA strand thus generated may be amplified by conventional PCR techniques, using one or more primers, such that at least one primer is homologous with a portion of the known region. The conventional PCR techniques may be, for example, long distance PCR techniques. The loop-forming oligonucleotide and the third region are complementary to the first portion and the second portion, respectively, of the known region of the sense strand. A single primer which is homologous with the first or the second portion of the known region can be annealed with a first DNA strand generated by extension of the panhandle structure or a second DNA strand generated by amplification of the first strand and the strand complementary to the first strand. Primers which can be used to amplify the DNA strand include, but are not limited to, a primer homologous with the second portion of the known region, a primer homologous with the first portion of the known region, and a primer homologous with a known portion of the "pan" region of the sense strand. Amplification of the DNA strand results in amplification of the unknown region.

Variant Panhandle PCR Method

The variant panhandle PCR method of the invention is an embodiment of panhandle PCR, and can, like the basic panhandle PCR method of the invention, be used to amplify an unknown region which flanks a known region of a leukemia-associated DNA sequence as follows.

A template polynucleotide is provided, the template polynucleotide comprising an antisense strand which comprises a region complementary to the known region of a leukemia-associated DNA sequence and a region complementary to an unknown region which flanks the DNA sequence. The region complementary to the unknown region is nearer the 5'-end of the antisense strand of the template polynucleotide than is the region complementary to the known region of the DNA sequence. Two portions of the known region of the DNA sequence are designated a first portion and a second portion, the first portion being nearer the unknown region than is the second portion. The template polynucleotide preferably comprises at least about twenty nucleotides complementary to the known region of the sense strand. The leukemia-associated DNA sequence is preferably MLL. The known region may be, for example, a portion of the breakpoint cluster region of MLL, a portion of MLL which flanks the breakpoint cluster region of MLL, a portion of an exon of MLL such as a portion of exon 5 or a portion of exon 11, or a portion of an intron of MLL.

The template polynucleotide may be provided in the form of single-stranded or double-stranded DNA. When the template polynucleotide is double-stranded DNA, the 5'-end of the antisense strand may overhang the 3'-end of the sense strand or the 3'-end of the sense strand may overhang the 5'-end of the antisense strand. The method used to obtain the template polynucleotide is not critical. Many methods are known for generating or isolating DNA suitable for use as template DNA. By way of example, the template polynucleotide may be provided by obtaining genomic DNA from a patient, contacting the genomic DNA with a restriction endonuclease, whereby a genomic DNA fragment is generated, the genomic DNA fragment comprising the known region. This fragment may be used as the template polynucleotide.

A first oligonucleotide is ligated to the 5'-end of the antisense strand of the template polynucleotide, the first oligonucleotide being homologous with the first portion of the known region of the sense strand of the DNA sequence. After ligating the first oligonucleotide to the template polynucleotide, the unknown region of the antisense strand is flanked on one side by the first oligonucleotide and on the other side by a polynucleotide complementary to the known region of the gene. A pre-template polynucleotide is annealed with the antisense strand, the pre-template polynucleotide being homologous with at least part of the second portion of the known region of the DNA sequence. The pre-template polynucleotide may, for example, be a primer homologous with part of the second portion, or a sense strand of the template polynucleotide. The pre-template polynucleotide is subjected to extension, whereby a sense strand is generated, the sense strand comprising the known region, the unknown region, and a loop-forming oligonucleotide at the 3'-end thereof. The loop-forming oligonucleotide is the complement of the first oligonucleotide and is complementary to the first portion of the known region.

The loop-forming oligonucleotide is then annealed with the first portion of the known region of the sense strand to cause the sense strand to assume a panhandle structure. Ligation of the first oligonucleotide to the antisense strand may be easier if a bridging oligonucleotide is used, wherein the bridging oligonucleotide is complementary to a portion of the antisense strand at the 5'-end thereof, and wherein the bridging oligonucleotide is complementary to the first oligonucleotide. By annealing the antisense strand, the bridging oligonucleotide, and the first oligonucleotide, the 3'-end of the first oligonucleotide may be positioned adjacent the 5'-end of the antisense strand.

In the panhandle structure, the known region of the leukemia-associated DNA sequence and the loop-forming oligonucleotide form a "handle" region" of duplex DNA, and the unknown region is located in a single-strand "pan" region of the structure which is bounded on each end by one of the two DNA strands of the "handle" region. If the panhandle structure is subjected to extension, then a third region, complementary to the second portion is attached to the free end of the loop-forming oligonucleotide, such that the double-stranded "handle" portion of the panhandle structure further comprises the second portion of the known region of the DNA sequence and its complement. Thus, a DNA strand having known nucleotide sequences at each end and the unknown region therebetween is generated.

The DNA strand thus generated may be amplified by conventional PCR techniques, using one or more primers, such that at least one primer is homologous with a portion of the known region. The conventional PCR technique may, for example, be a long-distance PCR technique. The loop-forming oligonucleotide and the third region are complementary to the first portion and the second portion, respectively, of the known region. A single primer which is homologous with the second or the first portion of the known region can be annealed with a first DNA strand generated by extension of the panhandle structure or a second DNA strand generated by amplification of the first strand and the strand complementary to the first strand. Primers which can be used to amplify the DNA strand include, but are not limited to, a primer homologous with the first portion of the known region, a primer homologous with the second portion of the known region, and a primer homologous with a known portion of the "pan" region of the sense strand. Amplification of the DNA strand results in amplification of the unknown region.

Alternate Embodiments of the Panhandle PCR Methods of the Invention

Certain embodiments of the panhandle PCR methods of the invention are now described. It is understood that the methods of the invention are not limited to the particular embodiments illustrated herein, but should be construed to include equivalent methods and variations thereof which can be designed by those skilled in the art upon a reading of the present disclosure.

Cloning of MLL genomic breakpoint regions by PCR methods other than those of the invention has been difficult because, although each breakpoint region on the derivative 11 ("der(11)") chromosome comprises a known 5' sequence from MLL, PCR primers could not be designed which were consistently specific for all of the many 3' breakpoint region sequences derived from unknown partner DNA sequences, including sequences derived from coding regions of genes, sequences derived from non-coding regions of genes, and sequences derived from intergenic DNA sequences. It has been estimated that no fewer than thirty different partner genes are involved in MLL translocation (Pui et al., 1995, Leukemia 9:762–769). Although fourteen partner genes of MLL have been cloned, including those described herein, partner gene sequence information is, in many cases, limited to cDNA sequences (Bernard et al., 1994, Oncogene 9:1039–1045; Nakamura et al., 1993, Proc. Natl. Acad. Sci. USA 90:4631–4635; Rubnitz et al., 1994, Blood 84:1747–1752; Prasad et al., 1993, Cancer Res. 53:5624–5628; Thirman et al., 1994, Proc. Natl. Acad. Sci. USA 91:12110–12114; Tse et al., 1995, Blood 85:650–656; Chaplin et al., 1995, Blood 86:2073–2076; Chaplin et al., 1995, Blood 85:1435–1441; Parry et al., 1994, Genes Chromosom. Cancer 11:79–84; Taki et al., 1997, Blood 89:3945–3950; Sobulo et al., 1997, Proc. Natl. Acad. Sci. USA 94:8732–8737; So et al., 1997, Proc. Natl. Acad. Sci. USA 99:2563–2568; Hillion et al., 1997, Blood 9:3714–3719; Borkhardt et al., 1997, Oncogene 14:195–202). The nucleotide sequences of the remaining partner genes have not yet been determined and, thus, are not available for design of primers for genomic breakpoint region cloning.

In approximately one-third of patients who exhibit molecular MLL gene rearrangement by Southern blot analysis, karyotype analysis cannot detect the translocation or provide information about potential translocation partners. Other translocation events involve partial tandem duplication of one or more regions of MLL (Schichman et al., 1994, Proc. Natl. Acad. Sci. USA 91:6236–6239; Schichman et al., 1994, Cancer Res. 54:4277–4280), and are not detectable on karyotype analysis.

For these reasons, a set of conventional PCR primers cannot reasonably be designed such that the primers can be used to amplify all possible MLL genomic breakpoint regions.

The panhandle PCR methods of the invention overcome the limitations of conventional PCR methods for amplification of leukemia-associated gene breakpoint regions. The methods described herein have been used to clone breakpoint regions comprising the MLL bcr in numerous patients. Nonetheless, it is clear that the methods of the invention can be used analogously to clone breakpoint region(s) of any leukemia-associated gene and other genes involved in translocations, whether somatic or constitutional in nature, and whether involved in cancer or other disease states (e.g. Look et al., 1997, In: *Principles and Practices of Pediatric Oncology*, 3rd ed., Pizzo et al., Eds, Lippincott-Raven Publishers, Philadelphia, Pa., Chapter 3). In MLL, the bcr is located in an 8.3 kilobase region interposed between exons 5 and 11 and bounded by BamHI sites at either end. The length of the bcr of MLL is suitable for amplification by the panhandle PCR methods of the invention.

Gale et al. demonstrated that MLL gene rearrangements involving MLL and AF4 may be detectable at birth by conventional PCR, several months or even years before the onset of leukemia (Gale et al., 1997, Proc. Natl. Acad. Sci. USA 94:13950–13954). However, MLL has many translocation partners, and no PCR primer set could amplify all possible translocations. Furthermore other methods such as Southern blot analysis, fluorescent in situ hybridization, and cytogenetic methods are not as sensitive as PCR methods for detecting translocation events.

Latency to onset of clinical disease in both infants and in patients with treatment-related leukemias with MLL gene translocations provides an opportunity for leukemia prevention by pre-leukemia screening and detection before cells with the translocation establish clonal dominance. The panhandle PCR methods of the invention have the sensitivity necessary for diagnostic use to detect MLL gene rearrangements before the onset of leukemia. The diagnostic capability of the panhandle PCR methods of the invention represents a significant advance relative to prior art gene rearrangement detection methods.

A single diagnostic test using a panhandle PCR method can screen for a panoply of translocation events. Isolation of one of numerous breakpoints and partner sequences can yield sequence information that is informative with regard to both diagnosis and prognosis. For example, for MLL, with its many translocation partners, such a diagnostic test does not exist.

Preliminary experiments involving serial dilutions indicate that the panhandle PCR methods of the invention can be used to detect an MLL gene translocation in an amount of DNA equivalent to the amount of DNA in as few as about thirty cells. These results were obtained without optimization of the detection system used. Thus, it is believed that the panhandle PCR methods of the invention may be useful for detecting translocation events in fewer than thirty cells. Furthermore, the usefulness of the methods of identifying the partner gene involved in a leukemia-associated translocation event may become even more apparent as the methods described herein and other methods are used to gather data regarding clinical outcomes associated with the identities of various partner genes. As this information base develops, the methods of the invention can be used to predict clinical outcomes in individual patients, and to assist practitioners to select an appropriate course of treatment. The panhandle PCR methods of the invention have the advantage of amplifying all MLL gene rearrangements without the need for primers for the many partner genes of MLL, and thus for pre-clinical detection and characterization of leukemia once disease is evident, and subsequent monitoring of the disease.

The panhandle PCR methods of the invention have been devised to simplify PCR-based cloning of genomic DNA having unknown sequences flanking known sequences, which is the case with many MLL genomic breakpoint regions.

One Embodiment of the Panhandle PCR Methods of the Invention

In one embodiment represented in FIG. 2, the variant panhandle PCR method of the invention is performed as follows.

Genomic DNA is obtained from a patient afflicted with leukemia and is digested to completion using the restriction endonuclease BamHI. This treatment generates a plurality of genomic DNA fragments, each having an overhanging region, whereby the 5'-end of each strand overhangs the 3'-end of the strand with which it is annealed.

A single-stranded first oligonucleotide that is homologous to a known sense MLL genomic sequence (designated "Primer 3" in this embodiment) is ligated to the 5' ends of the BamHI-digested genomic DNA fragments. A bridging oligonucleotide which is complementary to the four-nucleotide-residue overhanging region at one end and complementary to the first oligonucleotide at its other end facilitates the ligation. Primer 3 may be, for example, a 31-nucleotide first oligonucleotide homologous to nucleotides 51 through 81 of the bcr of MLL, in MLL exon 5. The purpose of the bridging oligonucleotide is to position the 3'-end of the first oligonucleotide adjacent each 5'-end of the BamHI-digested genomic DNA fragment. BamHI-digested genomic DNA fragments are added directly to the ligation reaction mixtures, i.e., without purifying fragments from the digestion reaction mixture. After ligation is completed, the bridging oligonucleotide and non-ligated first oligonucleotide may be degraded by addition of exonuclease I to the ligation mixture, which results in digestion of these oligonucleotides.

As represented in step 3 in FIG. 2, a primer (designated "Primer 1" in this embodiment) is used to generate a sense strand by extension of Primer 1 in the presence of the antisense strand of the template polynucleotide. Primer 1 is homologous with a portion of MLL, such as for example, the portion of MLL consisting of nucleotide residues 34 to 55 of the bcr of MLL, in MLL exon 5. Thus, a sense strand (the upper strand in FIG. 2 following step 3) is generated, comprising the known region of the leukemia-associated DNA sequence, the unknown region, and a loop-forming oligonucleotide at the 3'-end thereof. The loop-forming oligonucleotide is complementary to the first portion of the known region.

Heat denaturation can be used to dissociate the antisense strand of the template polynucleotide from the sense strand. Thereafter, intrastrand annealing of the loop-forming oligonucleotide with the first portion generates a panhandle structure. Extension of the recessed 3'-end of the panhandle structure completes generation of the panhandle structure. The intrastrand "pan" portion of the panhandle structure comprises the breakpoint region and the unknown partner DNA, while the handle comprises a known region of the template polynucleotide homologous with the sense strand of MLL and a region complementary to the sense strand of MLL.

PCR amplification of the panhandle structure in the presence of Primer 1, which anneals both at the 3'-end of the sense strand and at the 3'-end of the antisense strand of the template polynucleotide, exponentially amplifies the template polynucleotide, including the breakpoint region and the unknown partner DNA.

As represented by steps 4 and 5 in FIG. 2, further PCR amplification using one or more primers, each of which is nested with respect to Primer 1, can be performed to increase the yield and the specificity of the method. For example, two sequential nested, single-primer PCR amplifications may be performed, the first amplification being performed in the presence of an internal primer designated "Primer 2" in this embodiment, and the second amplification being performed in the presence of Primer 3. Primer 2 may, for example, be homologous with positions 38–61 of the bcr of MLL, in MLL exon 5. Primer 3 may, for example, be homologous with nucleotide residues 51 to 81 of the bcr of MLL.

Subcloning of the amplified polynucleotide product generated by an embodiment of either the basic or the variant panhandle PCR method of the invention may be desirable if the yield of the amplified polynucleotide product is not considered sufficient. When subcloning is desired, a simple and efficient method, herein designated "recombination PCR" may be used. Recombination PCR relates to the fact that E. coli mediates DNA recombination and that DNA ends comprising short regions of homology can undergo intra- and intermolecular recombination in vivo in E. coli, including, but not limited to, in RecA-deficient strains such as those routinely used for subcloning (Jones et al., 1991, BioTechniques 10:62–66). To perform subcloning by recombination PCR, PCR is performed using a HindIII-digested pUC19 plasmid template and primers having 5'-ends complementary to the primer used to generate the basic or the variant panhandle PCR product (Jones et al., 1991, BioTechniques 10:62–66). PCR products from both the panhandle PCR reaction and the pUC19 amplification are combined, they undergo in vivo recombination when transformed into E. coli with the desired recombinant plasmid. To identify recombinant plasmids containing products of basic or variant panhandle PCR, genomic subclones are screened by PCR rather than by preparing and digesting miniprep DNAs, as in conventional methods. Preliminary results indicate that this approach is faster than conventional subcloning methods.

It is anticipated that the panhandle PCR methods of the invention will lead to discovery of new MLL translocation partner genes. The panhandle PCR methods of the invention can be used to identify partner genes in leukemias associated with cytogenetic translocations involving bands 10q 11 or Xq22 where no partner genes have yet been cloned.

One anomaly that may be anticipated in certain circumstances using the panhandle PCR methods of the invention is the generation of nonspecific products. It is believed that, where such generation of nonspecific products may occur, the explanation relates to nonspecific annealing of a PCR primer with regions of DNA with which the primer is not 100% complementary. Should such nonspecific priming occur, fully constituted polymerase reaction mixtures may be kept at or above 80° C. prior to the first annealing reaction of any PCR amplification to minimize nonspecific priming (Mullis, 1984, PCR Meth. Applicat. 1:1–4). If multiple bands are observed following PCR amplification using nested primers as described herein, raising the annealing temperature by 1 or 2° C. should eliminate the shorter products. Alternatively, reducing the amount of DNA polymerase used in the PCR is helpful if multiple bands are observed following PCR amplification using nested primers.

Panhandle PCR methods have been used to amplify polynucleotides from about 2 to about 4.4 kilobases in length (Jones et al., 1992, Nucl. Acids Res. 20:595–600; Jones, 1995, PCR Meth. Applicat. 4:S195–S201; Jones, et al., 1993, PCR Meth. Applicat. 2:197–203). The variant panhandle PCR method of the invention has been used to amplify polynucleotides comprising MLL gene translocations from about 3.9 to about 8.3 kilobases in length. The basic panhandle PCR method of the invention has been used to amplify products comprising MLL gene translocations from about 2.5 to about 8.3 kb in length. The maximum length of the polynucleotide that can be amplified using the panhandle PCR methods of the invention has not been determined. Products as long as 9.4 kilobases have been obtained using test genes and the variant method. If difficulty is encountered in amplifying longer regions, the time permitted for intrastrand annealing may be increased.

Alternately, the use of primers which are homologous to a portion of the known region of the leukemia-associated gene very near the unknown region may be useful.

The variant panhandle PCR method of the invention may have advantages relative to the basic panhandle PCR method of the invention. In the basic panhandle PCR method, template-directed primer extension of the loop-forming oligonucleotide completes formation of the handle. This has the disadvantage of frequently creating a long complementary sequences, which can impede PCR initiation. Long complementary sequences are not created during the polymerase extension step in the variant panhandle PCR method, because the initial polymerase extension generates only a short complementary sequence that extends only as far as Primer 1. It has also been demonstrated that single primers inhibit PCR amplification of short products and amplify long target sequences with greater specificity. The variant panhandle PCR method is designed to use single primers very effectively. Single primer amplifications will not impede the amplification of products >1 kb. However, single primers also may be used in the basic panhandle PCR method. Also, the variant panhandle PCR method does not require a phosphorylated polynucleotide. For these reasons, the variant panhandle PCR method of the invention may have advantages relative to the basic panhandle PCR method of the invention in certain circumstances. Both are advantageous with respect to conventional cloning methods.

Another Embodiment of the Panhandle PCR Methods of the Invention

In another embodiment represented in FIG. 1, the basic panhandle PCR method of the invention is performed as follows.

High molecular weight genomic DNA is isolated from a patient afflicted with leukemia by ultracentrifugation on 4 molar GITC/5.7 molar CsCl gradients as described (Felix et al., 1990, J. Clin. Oncol. 8:431–442). Before performing panhandle PCR, genomic DNA from the patient is examined by Southern blot analysis for rearrangement of the 8.3 kilobase BamHI fragment that comprises the bcr of MLL, as described (Felix et al., 1995, Blood 85:3250–3256). Size(s) of any rearrangement(s) detected by Southern blot analysis indicates the possible anticipated approximate size of panhandle PCR products.

Figure 1B:
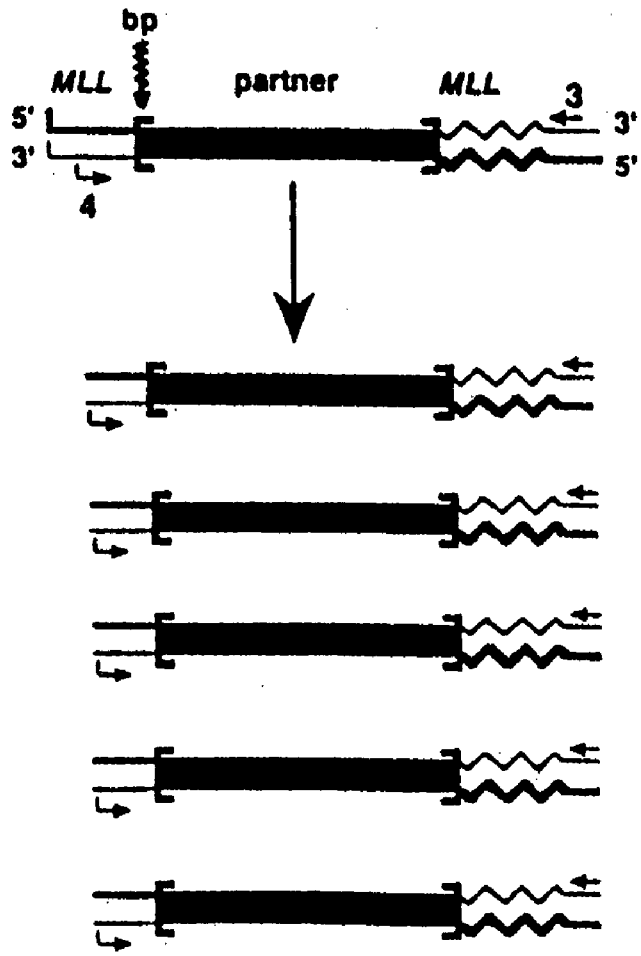

The method represented in FIG. 1 amplifies the breakpoint region of the der(11) chromosome, and is described in this embodiment in five steps. These five steps are first described generally, after which a specific protocol is described.

The first step represented in FIG. 1 concerning the generation of the template polynucleotide. A genomic DNA fragment is treated with the restriction endonuclease BamHI to generate a genomic DNA which has overhanging 5'-ends and which comprises a known region of the MLL gene and an unknown region of a translocation partner gene flanking the known region. For leukemias associated with MLL gene translocations, BamHI is the most appropriate restriction endonuclease for use in the panhandle PCR methods of the invention, because virtually all MLL genomic breakpoint regions are located on the same 8.3 kb BamHI restricted genomic DNA fragment. The genomic DNA fragment is treated with calf intestinal alkaline phosphatase to prevent religation in Step 2.

The purpose of Steps 2 and 3 is to form the "handle" of the panhandle structure using the template polynucleotide. Formation of the handle involves ligating DNA complementary to a known sense region of MLL to the 3'-end of the unknown region of the sense strand and forming an intrastrand loop comprising the breakpoint region of MLL and unknown translocation partner DNA. Step 2, as represented in FIG. 1, involves ligation of a single stranded 5'-phosphorylated loop-forming oligonucleotide to the 3'-ends of the genomic DNA fragment. The four-nucleotide 5'-end of the loop-forming oligonucleotide is complementary to the 5'-overhanging region of the BamHI-digested genomic DNA fragment. The 3'-end of the loop-forming oligonucleotide is complementary to a first portion of the known region of the sense strand of MLL comprising exon 5, which is located in the bcr of MLL. The sense strand (the top strand in Step 2 of FIG. 1) is the template polynucleotide represented in Step 3.

Formation of the handle is completed in Step 3 by intrastrand annealing of the loop-forming oligonucleotide to the first portion of the known region, and by subjecting the resulting panhandle structure to extension. The panhandle structure is subjected to extension by adding the polynucleotide to a reaction mixture comprising DNA polymerase, dNTPs, and PCR reaction buffer. The reaction mixture is preheated to 80° C. before the addition of the panhandle structure to the reaction mixture in order to prevent nonspecific annealing and polymerization. After addition of the panhandle structure, the reaction mixture is heated to 94° C. for 1 minute to generate single-stranded polynucleotide. Intrastrand annealing of the loop-forming oligonucleotide to the first portion of the known region and template-directed polymerase extension of the recessed 3'-end of the panhandle structure are effected by subjecting the mixture to a 2 minute ramp to 72° C. and incubation of the reaction mixture at 72° C. for 30 seconds, whereby the handle of the panhandle structure is extended.

In steps 4 and 5, as represented in FIG. 1, primers homologous with the sense strand of portions of exon 5 of MLL are used to amplify the breakpoint region and the unknown translocation partner DNA. The positions and orientations of the primers with respect to the ligated polynucleotide are shown in step 1 of FIG. 1. Step 4 comprises subjecting the panhandle structure generated in step 3 to PCR in the presence of primers 1 and 2. Primer 1 is homologous to a portion of the sense strand of MLL exon 5 located 5' with respect to the first portion. Primer 2 is homologous to a portion of the sense strand of MLL exon 5 located between the 3'-end of the first portion and the translocation breakpoint. A nested PCR reaction is performed in step 5, in the presence of internal primers 3 and 4 to yield an amplified polynucleotide product which comprises the unknown region.

A specific protocol corresponding to the embodiment of the basic panhandle PCR method represented in FIG. 1 is now described. Step numbers refer both to FIG. 1 and to the immediately preceding discussion.

Step 1. BamHI Digestion and Calf Intestinal Alkaline Phosphatase (CIAP) Treatment 1. About 5 micrograms of genomic DNA obtained from a patient afflicted with leukemia is digested to completion at 37° C. for two hours in a digestion mixture comprising an appropriate buffer containing bovine serum albumin and 40 units (8 units per microgram) of BamHI (New England Biolabs, Beverly, Mass.). The reaction volume is 100 microliters. Genomic DNA fragments having 5'-overhanging regions are thereby generated.

2. The genomic DNA fragments are dephosphorylated by adding 0.05 unit of calf intestinal alkaline phosphatase (Boehringer Mannheim Biochemicals, Indianapolis, Ind.) to the digestion mixture. A 100 microliter CIAP stock solution comprising 0.01 unit per microliter of CIAP is prepared by diluting the 1 unit per microliter CIAP preparation supplied by the manufacturer 100-fold in TE buffer, which comprises 10 millimolar Tris-HCl and 1 millimolar EDTA. 5 microliters of the CIAP stock solution is added to the digestion mixture, and the mixture is incubated at 37° C. for 30 minutes.

3. CIAP-treated genomic DNA fragments are purified by glass bead extraction using a GENECLEAN III kit (BIO 101, Inc., La Jolla, Calif.) according to the manufacturer's instructions for 5 micrograms of genomic DNA in order to eliminate the protein. Purified DNA fragments are eluted in a final volume of 50 microliters of TE buffer. 25 microliters of the eluted fragments are stored at −20° C. for later use as an unligated control.

Step 2. Ligation of Single-stranded 5' Phosphorylated Loop-forming Oligonucleotide to the 3' ends of the Genomic DNA Fragments The sequence of the 5' phosphorylated loop-forming oligonucleotide useful for amplification of the translocation breakpoint region of the der(11) chromosome is 5'-GATCGAAGCT GGAGTGGTGG CCTGTTTGGA TTCAGG-3' (SEQ ID NO: 4). The 32-nucleotide 3'-end of this 5' phosphorylated loop-forming oligonucleotide is complementary to nucleotides 92–123 of the bcr of MLL, in MLL exon 5. The four-nucleotide-residue 5'-end of this 5' phosphorylated loop-forming oligonucleotide is complementary to the 5'-overhanging region of the genomic DNA fragments, and is designed such that it does not reconstitute the BamHI site upon ligation of the loop-forming oligonucleotide to the genomic DNA fragment.

1. The 5'-phosphorylated loop-forming oligonucleotide is suspended in distilled water at a final concentration of 0.25 micrograms per microliter.

2. Reagents are added to a container to generate a ligation mixture having a final volume of 50 microliters. The ligation mixture comprises 16.9 microliters of distilled water, 25 microliters (2.5 micrograms) of phosphatase-treated genomic DNA fragments suspended in TE buffer, 2.1 microliters (516 nanograms) of the 5'-phosphorylated loop-forming oligonucleotide, 5 microliters of 10×ligase buffer (Boehringer Mannheim Biochemicals, Indianapolis, Ind.), and 1 microliter of a solution comprising 1 Weiss Unit per microliter of T4 DNA ligase (Boehringer Mannheim Biochemicals, Indianapolis, Ind.). The ligation mixture is incubated overnight at 4° C. or, alternately, at 17° C., to generate oligonucleotide-ligated DNA fragments. The 516 nanograms of loop-forming oligonucleotide represents an approximately 50-fold molar excess with respect to the genomic DNA fragments.

3. The oligonucleotide-ligated DNA fragments are purified using a GENECLEAN III kit (BIO 101, Inc., La Jolla, Calif.) according to the manufacturer's directions. The oligonucleotide-ligated DNA fragments are eluted in a final volume of 25 microliters of TE buffer.

Step 3. Addition of DNA to Taq/dNTP Mixture, Denaturation, Intrastrand Annealing, Panhandle Formation, and Polymerase Extension 1. 25 microliters of a 2×PCR reagent is prepared by adding to a container 2.5 units (0.75 microliter) of a Taq/Pwo DNA polymerase mixture (Expand Long Template PCR System, Boehringer Mannheim Biochemicals, Indianapolis, Ind.), 0.7 microliters of a 1:1:1:1 nucleoside mixture comprising 25 micromolar each dATP, dCTP, dGTP, and dTTP, 5 microliters of 10×PCR reaction buffer (Boehringer Mannheim Biochemicals, Indianapolis, Ind.), and 18.55 microliters of distilled water. The 2×PCR reagent may be prepared as a bulk cocktail, pre-aliquoted, and stored at −20° C. for future use.

2. The oligonucleotide-ligated DNA fragments are subjected to intrastrand annealing and extension by preparing a reaction mixture comprising 18 microliters of distilled water, 25 microliters of 2×PCR reagent in a 500 microliter thin-wall tube (Perkin-Elmer). One drop (circa 50 microliters) of mineral oil is layered atop the reaction mixture. To prevent non-specific annealing and polymerization, the tube is pre-heated to 80° C. in a thermal cycler.

3. A 200 nanogram aliquot (2 microliters) of the suspension of oligonucleotide-ligated DNA fragments is added to the pre-heated reaction mixture. After addition of the DNA suspension, the reaction mixture contains 2.5 units of Taq/Pwo DNA polymerase mix (Expand Long Template PCR System, Boehringer Mannheim Biochemicals, Indianapolis, Ind.), 385 micromolar each dNTP (Expand Long Template PCR System, Boehringer Mannheim Biochemicals, Indianapolis, Ind.), and PCR reaction buffer at 1.1×final concentration in a volume of 45 microliters. The reaction mixture is heated at 94° C. for 1 minute to dissociate the oligonucleotide-ligated DNA fragments. A negative control reaction mixture comprises all of the reaction mixture reagents, except that 200 nanograms (2 microliters) of the unligated control DNA is used in place of the oligonucleotide-ligated DNA fragments. A reagent control reaction mixture comprises all of the reaction mixture reagents, but does not comprise DNA.

4. Intrastrand annealing of the loop-forming oligonucleotide to the complementary sequence of the first portion of the known region to form a panhandle structure and polymerase extension of the recessed 3'-end of the panhandle structure are effected by following the 94° C. heat denaturation step with a two minute ramp of the reaction mixture temperature to 72° C. and incubation of the reaction mixture at 72° C. for 30 seconds.

5. Maintain the reaction mixture at 80° C. before addition of the PCR primers in Step 4 to prevent priming at low stringency and generation of nonspecific products.

Step 4. Addition of MLL Primers 1 and 2 and Thermal Cycling

1. The nucleotide sequence of MLL primer 1 is 5'-TCCTCCACGA AAGCCCGTCG AG-3' (SEQ ID NO: 5), and the nucleotide sequence of MLL primer 2 is 5'-TCAAGCAGGT CTCCCAGCCA GCAC-3' (SEQ ID NO: 6). With the reaction mixture maintained at 80° C., add 12.5 picomoles of each primer in a volume of 2.5 microliters to the reaction mixture to yield a first PCR mixture. These additions result in concentrations in the 50 microliter first PCR mixture of 350 micromolar for each dNTP and 1×for PCR reaction buffer.

In a variation of this embodiment, primer 2 has a nucleotide added to its 5'-end that was not homologous with the known region of the sense strand of MLL. This is a precaution to prevent short-circuiting of PCR in the first PCR mixture if using Taq DNA polymerase alone. Short-circuiting could occur by annealing of the 3'-end of one strand of a short nonspecific PCR product to the template polynucleotide. The necessity of this precaution has not been tested. Results obtained using a similar method involving long-range PCR reagents including a DNA polymerase having 3' exonuclease activity suggests that this precaution is unnecessary.

2. If Southern blot analysis information is available, then that information can be used to determine the duration of the elongation segment in the PCR reaction (using as a rule of thumb that 1 minute should be allowed per kilobase). To amplify products 8.3 kilobases and 7 kilobases in length, the following conditions have been used. The initial denaturation was performed at 94° C. for 1 minute. Ten cycles were performed by maintaining the first PCR mixture at 94° C. for 10 seconds and at 68° C. for 7 minutes. Twenty cycles were performed by maintaining the first PCR mixture at 94° C. for 10 seconds and at 68° C. for 7 minutes, wherein the period during which the mixture was maintained at 68° C. was incremented 20 seconds per cycle. A final elongation was performed at 68° C. for 7 min. It is understood that shorter products can be amplified using shorter, as well as longer, elongation times.

Step 5. Perform Nested PCR Using Internal Primers 3 and 4

1. The nucleotide sequence of MLL internal primer 3 is 5'-AGCTGGATCC GGAAAAGAGT GAAGAAGGGA ATGTCTCGG-3' (SEQ ID NO: 7), and the nucleotide sequence of MLL internal primer 4 is 5'-AGCTGGATCC GTGGTCATCC CGCCTCAGCC AC-3' (SEQ ID NO: 8). Underlined sequences are BamHI restriction endonuclease sites. A second PCR mixture is prepared by combining 25 microliters of 2×PCR reagent, 19 microliters of distilled water, 2.5 microliters (12.5 picomoles) of each of MLL internal primers 3 and 4, and a 1 microliter aliquot of the first PCR mixture. One drop (circa 50 microliters) of mineral oil is layered atop the second PCR mixture. The second PCR mixture is subjected to the same PCR conditions as was the first PCR mixture.

3 microliters of the second PCR mixture is visualized on an ethidium-stained minigel. Detection of a product having the same approximate size as the BamHI fragment detected by genomic Southern blot analysis is an indication that the amplified products obtained following Step 5 comprise the known sequence from MLL flanked by the unknown partner DNA.

Subcloning and sequencing of the products of panhandle PCR Each of MLL internal primers 3 and 4 comprises a BamHI restriction sites which is useful for subcloning. The amplified products obtained following Step 5 are isolated using an agarose gel and subcloned to permit sequencing of the translocation breakpoint region, the unknown region, or both.

To validate the results, validating primers may be designed from sequences of the subcloned products of panhandle PCR. These validating primers may encompass the translocation breakpoint region. If such validating primers are used to amplify genomic DNA obtained from the patient afflicted with leukemia, direct genomic sequencing may be performed, and the results obtained using panhandle PCR may thereby be confirmed. RT-PCR may also be used to validate results obtained by panhandle PCR methods.

This embodiment of the panhandle PCR methods has been used to clone three MLL genomic breakpoint regions, amplifying polynucleotides from about 2.5 kilobases to about 8.3 kilobases in length. Application of this embodiment of the methods in three cases of infant ALL and in two treatment-related leukemias identified the respective MLL genomic breakpoint regions and previously uncharacterized intronic sequences in the partner genes. In two of the five cases, the karyotype did not suggest the chromosomal location of the translocation partner.

Panhandle PCR is a technical advance over prior methods of investigating the molecular pathogenesis of leukemias associated with MLL gene translocations. This embodiment of the panhandle PCR methods of the invention is practical in cases where the amount of genomic DNA is limited. Panhandle PCR is a definitive PCR approach for identifying additional new partner genes of MLL and for amplifying the translocation breakpoint regions of other genes wherein the partner gene is undetermined.

Subcloning of the Products of Panhandle Variant PCR by Recombination PCR

Recombination PCR uses *E. coli* itself to mediate DNA recombination (Jones et al., 1991, BioTechniques 10:62–66). The observation that DNA ends containing short regions of homology can undergo intra- and intermolecular recombination in vivo in *E. coli*, including RecA(−) strains routinely used for subcloning, led to the development of recombination PCR (Jones et al., 1991, BioTechniques 10:62–66). A sample protocol which can be used with either of the panhandle PCR methods of the invention is now described.

First, 0.5 micrograms of pUC 19 (Gibco BRL) is linearized by digestion with 10 units HindIII (Gibco BRL). A 2 nanogram aliquot of the restriction enzyme-digested plasmid template is amplified in a 50 microliter PCR reaction containing 1.25 units Amplitaq DNA polymerase (Perkin Elmer, Norwalk, Conn.), 12.5 picomoles of each primer, 200 micromolar of each dNTP, and 1×PCR reaction buffer (Perkin Elmer) to generate a linearized plasmid having ends complementary to the ends of the product of panhandle PCR product to be inserted. The sequences of the primers used to amplify the HindIII-digested pUC 19 may be, for example, 5'-TCCCTTCTTC ACTCTTTTCC TCGATGGCGT AAT-CATGGTC ATAGC-3' (SEQ ID NO: 19) and 5'-TCCCTTCTTC ACTCTTTTCC TCGACATGCC TGCAGGTCGA CTCTAGAG-3' (SEQ ID NO: 20). After initial denaturation at 94° C. for 1 minute, twenty five cycles are performed, wherein the reaction mixture is maintained at 94° C. for 30 seconds, at 50° C. for 30 seconds, and at 72° C. for 2 minutes, 42 seconds, followed by a final elongation at 72° C. for 7 minutes.

The products from PCR amplification of the plasmid and from panhandle variant PCR may purified using a Geneclean III kit (Bio 101, Inc., La Jolla, Calif.) according to the manufacturer's instructions and resuspended in 10 microliters of elution buffer provided in the kit (Bio 101, Inc.). 2.5 microliters of the purified PCR products from amplification of the plasmid and 2.5 μl of the purified panhandle PCR products are combined and added to 50 microliters of MAX Efficiency DH5α Competent Cells (Life Technologies, Gaithersburg, Md.) to undergo in vivo recombination. The transformation procedure is as described in the manufacturer's instructions (Life Technologies), except that the entire 1 milliliter reaction is plated. Individual transformants are grown overnight in 4 milliliters of Luria broth containing 100 micrograms per milliliter ampicillin.

PCR may be used to identify recombinant plasmids containing products of panhandle PCR. 2 microliter aliquots of the saturated 4 milliliter cultures are amplified in PCR reactions containing 0.5 microliters (1.75 units) of Taq/Pwo DNA polymerase mix, 350 micromolar of each dNTP, 1×Expand Buffer 1 (Expand Long Template PCR System, Boehringer Mannheim) and 12.5 picomoles of a primer, such as the first oligonucleotide of the variant panhandle PCR method. The PCR conditions are the same as those for panhandle variant PCR, as described herein. Analysis of the products by agarose gel electrophoresis identifies those transformants containing the recombinant plasmid DNA of interest. Desired transformants are grown in 25 milliliter cultures for plasmid preparation and automated sequencing.

Method of Identifying a Translocation Partner

The invention also includes a method of identifying a translocation partner of a leukemia-associated gene. It is understood that the translocation partner may be a gene other than the leukemia-associated gene or a portion of the leukemia-associated gene which is duplicated. This identification method of the invention is performed as follows.

An unknown region flanking a leukemia-associated gene is amplified using one of the panhandle PCR methods of the invention. After the unknown region is amplified, a portion of a human gene homologous with the unknown region is identified, whereby that human gene is identified as the translocation partner. Numerous methods are known whereby a portion of a human gene homologous with an amplified portion of a template polynucleotide may be identified. The choice of method used to identify such a homologous human gene is not critical. By way of example, the nucleotide sequence of the unknown region may be determined and then compared with the nucleotide sequence of a cloned or characterized human gene. The human gene may be one which has a sequence listed in a database of human gene sequences. Further by way of example, the nucleotide sequence of the unknown region may be compared with the nucleotide sequence of a human gene by contacting a test polynucleotide with a control polynucleotide derived from the human gene. The test polynucleotide may be selected from the group consisting of a polynucleotide homologous with the unknown region and a polynucleotide complementary to the unknown region. If the test polynucleotide is capable of annealing with the control polynucleotide with high stringency, then the human gene is either homologous with or complementary to the unknown region of the template polynucleotide. Either way, the translocation partner is identified as at least a portion of the human gene.

A Kit for Panhandle PCR Analysis of Leukemia-Associated DNA Sequences

The invention further includes a kit useful for performing the panhandle PCR methods of the invention. The kit of the invention for performing the basic panhandle PCR method comprises an oligonucleotide and a first primer. The oligonucleotide is complementary to a known region of the sense strand of a leukemia-associated DNA sequence. The first primer is homologous with the known region. The oligonucleotide and first primer are used in the basic panhandle PCR method as described herein, the oligonucleotide being the loop-forming oligonucleotide of the basic panhandle PCR method.

The kit of the invention for performing the variant panhandle PCR method also comprises an oligonucleotide and a first primer. The oligonucleotide is homologous with a known region of the sense strand of a leukemia-associated DNA sequence. The primer is homologous with the known region. The oligonucleotide and first primer are used in the variant panhandle PCR method as described herein, the oligonucleotide being the first oligonucleotide of the basic panhandle PCR method, and the first primer being the pre-template polynucleotide of that method, the first primer of that method, or both.

In either kit, the leukemia-associated DNA sequence may, for example, be MLL. The known region may, for example, be selected from the group consisting of a portion of the breakpoint cluster region of MLL, a portion of MLL which flanks the breakpoint cluster region of MLL, a portion of an intron of MLL, and a portion of an exon of MLL such as exon 5 or exon 11.

The kit of the invention may further comprise an internal primer, wherein the internal primer is nested with respect to the first primer, and wherein the internal primer is selected from the group consisting of a primer homologous with the known region of the sense strand. For example, the internal primer may be a primer homologous with a portion of the known region of the sense strand near the end of the known region that is nearer an unknown region which flanks the known region. The kit may, of course, comprise a plurality of internal primers.

The kit of the invention may also comprise a second primer, wherein when the first primer is homologous with the known region of the sense strand, said second primer is homologous with a portion of the known region which is located within the "pan" portion of the panhandle structure generate using the kit of the invention.

The kit of the invention may comprise an internal primer which is nested with respect to each of the first primer and the second primer, and wherein the internal primer is homologous with the known region of the sense strand.

In addition to the various primers described herein, the kit of the invention may further comprise one or more of a restriction endonuclease, at least one reagent for ligating an oligonucleotide to a DNA strand obtained from a human patient, at least one reagent for extending a polynucleotide, or at least one reagent for performing PCR. The kit of the invention may also comprise one or more recombination PCR primers, as described herein to amplify the linearized plasmid if recombination PCR-based subcloning is desired. Examples of recombination PCR primers which may be included in the kit include the following two primers: 5'-ACATTCCCTT CTTCACTCTT TTCCTGGCGT AAT-CATGGTC ATAGC-3' (SEQ ID NO: 21) and 5'-GTGGCTGAGG CGGGATGACC ACCATGCCTG CAGGTCGACT C-3' (SEQ ID NO: 22).

Reagents useful for ligating an oligonucleotide to a DNA strand are well known and include, for example, T4 DNA ligase and buffers in which T4 DNA ligase is known to be enzymatically active. Reagents useful for template-directed polynucleotide extension are also well known and include, for example, Taq DNA polymerase, Pwo DNA polymerase, nucleoside triphosphates, and appropriate buffers. Reagents useful for performing PCR are likewise well known and include, for example, Taq DNA polymerase, Pwo DNA polymerase or another proof-reading enzyme, nucleoside triphosphates, and appropriate buffers.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Panhandle PCR: A Technical Advance in MLL Genomic Breakpoint Region Cloning

Known panhandle PCR methods (e.g. Jones et al., 1992, Nucl. Acids Res. 20:595–600; Jones, 1995, PCR Meth. Applicat. 4:S195–S201) were adapted for use in cloning a MLL genomic breakpoint region on a der(11) chromosome obtained from a three month old female infant patient afflicted with ALL. Karyotype analysis of the patient was technically unsuccessful. As described in this Example, a basic panhandle PCR method was adapted to facilitate cloning of the 11 q23 genomic translocation breakpoint.

A 5'-phosphorylated loop-forming oligonucleotide, which is complementary to a portion of MLL, was ligated to translocation partner DNA located 3' with respect to the breakpoint. It was thereby possible to generate a template polynucleotide capable of forming a panhandle structure wherein the intrastrand loop of the panhandle structure comprised the translocation breakpoint region, including the unknown partner DNA. The duplex "handle" portion of the panhandle structure comprised a portion of the template polynucleotide homologous with a known region of MLL and a region complementary to that portion Primers derived from MLL were used to amplify the breakpoint region, including the unknown partner DNA.

The materials and methods used in the experiments presented in this Example are now described.

The Infant Patient

The three month old infant patient presented with a white blood cell count (WBC) of $399 \times 10^9$ cells per liter and with a large extramedullary tumor burden typical of infant ALL. Consistent with early B lineage ALL, the patient's bone marrow was replaced by lymphoblasts of French-American-British L1 morphology that expressed tdt, CD34, HLA DR and CD19, but not CD10, CD20, or myeloid antigens.

Before performing panhandle PCR, Southern blot analysis of genomic DNA from the infant patient afflicted with ALL was performed to detect rearrangement of the 8.3 kb BamHI fragment that comprises the bcr of MLL. When such a rearrangement was detected, the size of the rearranged fragment was used as an approximation of the expected size of the polynucleotide to be amplified by panhandle PCR.

A basic panhandle PCR method was performed as follows.

Step 1. Genomic DNA was digested using restriction endonuclease BamHI, yielding genomic DNA fragments each having a 5'-overhanging region at each end. One of these fragments comprises a known region of MLL, the bcr of MLL, and, if the fragment was obtained from a patient in whom a translocation event associated with MLL had occurred, translocation partner DNA. The fragments were treated with calf intestinal alkaline phosphatase to prevent religation in Step 2.

Step 2. The purpose of Steps 2 and 3 was to form the handle portion of a panhandle structure. Step 2 involved ligation of a single-stranded 5'-phosphorylated loop-forming oligonucleotide to each of the 3'-ends of the genomic DNA fragments generated in Step 1. The loop-forming oligonucleotide had a four-nucleotide 5'-overhanging region which was complementary to the 5'-overhanging regions of the fragments. The 3'-end of the loop-forming oligonucleotide was complementary to a first portion of MLL, the first portion comprising a portion of exon 5, which is within the bcr of MLL. The sense strand of the fragment was used to generate the template polynucleotide in Step 3.

Step 3. Formation of the handle portion of the panhandle structure was completed in Step 3 by intrastrand annealing of the loop-forming oligonucleotide with the first portion of the template polynucleotide and subsequent polymerase extension of the recessed 3'-end of the duplex region of the template polynucleotide. At this point, the intrastrand loop portion of the panhandle structure comprised the translocation breakpoint region and unknown partner DNA, and the handle portion of the panhandle structure comprised a known region of the template polynucleotide having known (MLL) sense sequence and sequence complementary to this known region.

Steps 4 and 5. Because the template polynucleotide comprised regions of known sequence at each end, it was possible to use primers derived from MLL to amplify a portion of the template polynucleotide. The primers which were used were in the sense orientation with respect to exon 5 of MLL. Nested PCR primers were used in Step 5 to enhance the yield of amplified template polynucleotide product. This method has been used to clone five MLL genomic breakpoint regions.

Further details of this procedure were as follows:

The basic panhandle PCR method described in this example was analogous to the method depicted in FIG. 1, which is referred to in this Example for the purpose of illustration only.

In step 1 in FIG. 1, 5 micrograms of genomic DNA was digested to completion using 40 units of BamHI (New England Biolabs, Beverly, Mass.) to generate genomic DNA fragments having 5'-overhanging regions. The genomic DNA comprised a known region of MLL and an unknown region flanking the known region, the unknown region comprising the translocation partner DNA. The genomic DNA fragments were treated with 0.05 units of calf intestinal alkaline phosphatase (Boehringer Mannheim Biochemicals) at 37° C. for 30 minutes to prevent religation in step 2. The genomic DNA fragments were purified using a GENECLEAN II™ kit (BIO 101, Inc., La Jolla, Calif.).

In step 2 in FIG. 1, a single-stranded 5'-phosphorylated loop-forming oligonucleotide was ligated to the 3'-end of each genomic DNA fragment strand. The sequence of the loop-forming oligonucleotide was 5'-GATCGAAGCT GGAGTGGTGG CCTGTTTGGA TTCAGG-3' (SEQ ID NO: 4). The four-nucleotide-residue 5'-end of the loop-forming oligonucleotide was complementary to the 5'-overhanging region of the genomic DNA fragments, and does not reconstitute the BamHI site upon ligation to an individual genomic DNA fragment. The thirty-two nucleotides of the 3'-end of the loop-forming oligonucleotide were complementary to nucleotide positions 92–123 of MLL exon 5, which is within the bcr of MLL. The 50 microliter ligation reaction mixture comprised 2.5 micrograms of genomic DNA fragments, a 50-fold molar excess of the loop-forming oligonucleotide, 1 Weiss Unit of T4 DNA ligase (Boehringer Mannheim), and 1×ligase buffer (Boehringer Mannheim). Ligations were performed overnight at 4° C. to generate template polynucleotide. The template polynucleotide was purified using a GENECLEAN II™ kit (BIO 101, Inc., La Jolla, Calif.).

In step 3 in FIG. 1, the panhandle structure was generated. A 200 nanogram aliquot of template polynucleotide was added to an extension mixture comprising 2.5 U Taq/Pwo DNA polymerase mix, 385 µM each dNTP, and PCR reaction buffer at 1.1×final concentration in a total volume of 45 microliters (Expand Long Template PCR System, Boehringer Mannheim Biochemicals, Indianapolis, Ind.). The extension mixture was preheated to 80° C. before addition of the template polynucleotide to prevent non-specific annealing and polymerization. The extension mixture was then maintained at 94° C. for 1 minute to denature the template polynucleotide. The sense strand with respect to MLL was used as the template polynucleotide (represented by the top strand in FIG. 1). Intrastrand annealing of the loop-forming oligonucleotide to the complementary sequence in the known (MLL) portion of the template polynucleotide yielded the panhandle structure. Polymerase extension of the free 3'-end of the loop-forming oligonucleotide was accomplished by a 2 minute ramping of the extension mixture temperature to 72° C. to complete formation of the handle portion of the panhandle structure.

In step 4 in FIG. 1, primers homologous with known portions of MLL were added to the extension mixture and thermal cycling was performed. MLL primer 1 (5'-TCCTCCACGA AGCCCGTCG AG-3'; SEQ ID NO: 5) and MLL primer 2 (5'-TCAAGCAGGT CTCCCAGCCA GCAC-3'; SEQ ID NO: 6) were added. 12.5 picomoles of each of these primers, each suspended in a volume of 2.5 microliters was added to the extension mixture to yield a first PCR mixture in which final concentrations in the 50 volume were 350 micromolar for each dNTP and 1×for PCR reaction buffer. Following a 1 minute initial denaturation period during which time the first PCR mixture was maintained at 94 for 1 minute Ten cycles were performed by maintaining the first PCR mixture at 94° C. for 10 seconds and at 68° C. for 7 minutes. Twenty cycles were performed by maintaining the first PCR mixture at 94° C. for 10 seconds and at 68° C. for 7 minutes, wherein the duration of this period was incremented 20 seconds per cycle. A final elongation was performed at 68° C. for 7 min.

In step 5 in FIG. 1, another PCR reaction was performed using nested MLL internal primers and a 1 microliter aliquot of the first PCR mixture as template to enhance the yield and specificity of the amplified polynucleotide product. Sequences of nested MLL internal primers 3 and 4 were 5'-AGCTGGATCC GGAAAAGAGT GAAGAAGGGA ATGTCTCGG-3' (SEQ ID NO: 7) and 5'-AGCTGGATCC GTGGTCATCC CGCCTCAGCC AC-3' (SEQ ID NO: 8), respectively. Conditions for nested PCR were the same as in Step 4.

The results of the experiments presented in this Example are now described.

Panhandle PCR Identified MLL Genomic Breakpoint Regions Comprising Unknown Partner DNA The basic panhandle PCR method was used to clone the translocation breakpoint region of the infant patient described herein, who was afflicted with ALL. Southern blot analysis of diagnostic marrow obtained from the three month old infant patient indicated that two MLL gene rearrangements had occurred the translocation breakpoint junction region, suggesting that chromosomal translocation had occurred. Southern blot analysis using BamHI-B859, XbaI-B859 and XbaI-SKV3 restriction enzyme-cDNA probe combinations indicated that the translocation breakpoint was located within the first 4464 nucleotide residues of the 8.3 kilobase bcr region of MLL. The translocation partner was unknown because no mitoses were available for karyotype analysis. Using the basic panhandle PCR method described herein, a predicted 8.3 kilobase amplification product was obtained from MLL genes in control DNA obtained from the infant patient's mother. Also using the basic panhandle PCR method described herein, a 7 kilobase amplification product was obtained from the der(11) chromosome of the leukemia of the infant patient. An 8.3 kilobase amplification product was also obtained from the normal MLL allele of the leukemia of the infant patient. The 7 kilobase amplification product was subcloned and the nucleotide sequences of three genomic subclones were determined.

The translocation breakpoint in the infant patient was identified at nucleotide position 3802 of the bcr of MLL, in MLL intron 8.

Subcloning and Sequencing of the Products of Panhandle PCR

Polynucleotide products amplified using a panhandle PCR method described herein were separated on an agarose gel and subcloned into the BamHI site of pBluescript SK II™ (Stratagene, Inc., La Jolla, Calif.) using standard methods. Automated nucleotide sequencing of three genomic subclones identified the MLL genomic breakpoint and the sequence of the unknown partner gene that was flanking MLL.

The predicted 8.3 kb panhandle PCR product from the normal MLL genes was obtained in control maternal DNA. Both a 7 kb product from the der(11) chromosome and an 8.3 kb product were obtained from the normal MLL allele in the leukemia (FIG. 2). The 7 kb product from the der(11) chromosome was subcloned and three individual genomic subclones were sequenced.

Figure 3:
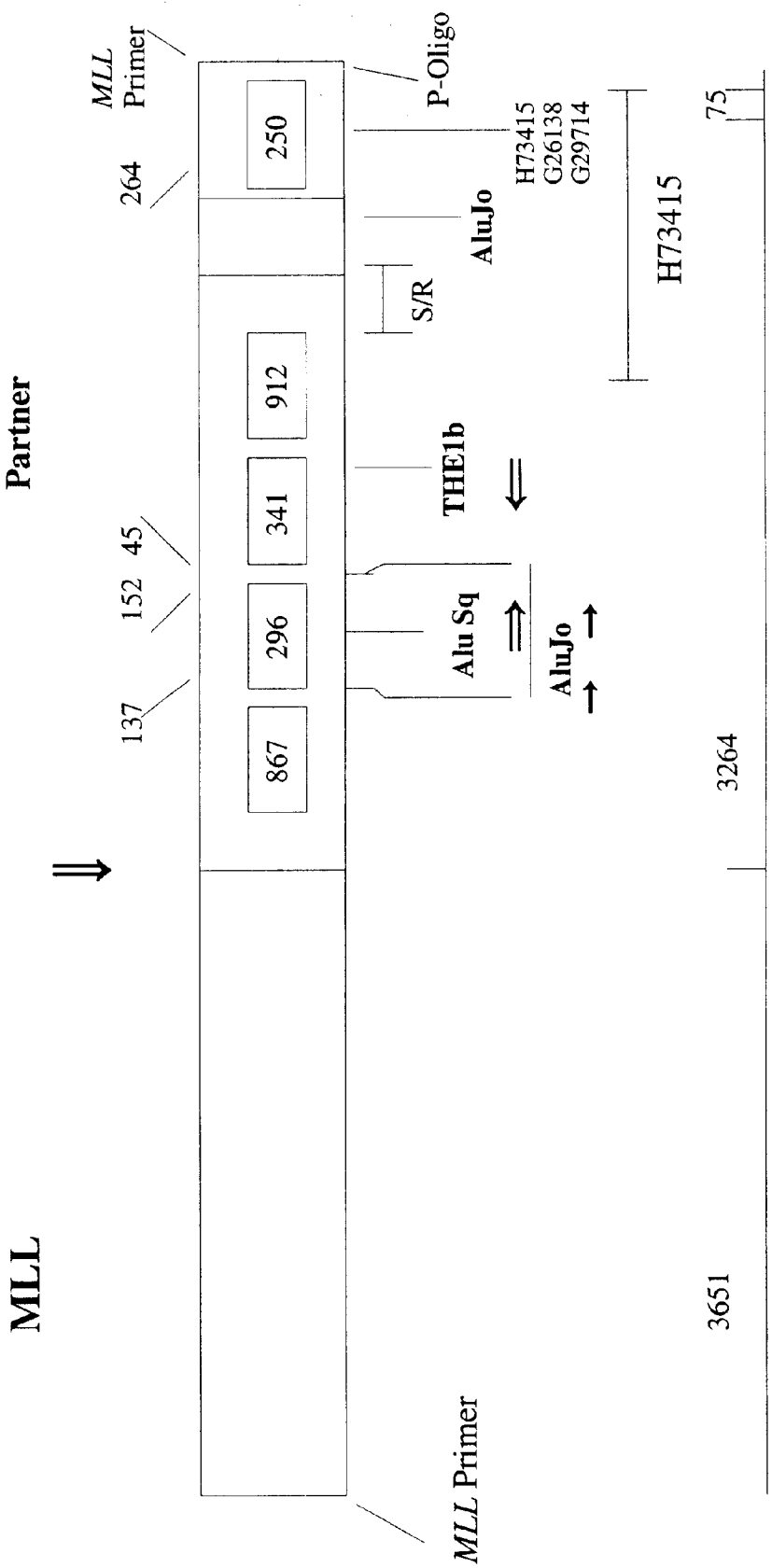
FIG. 3 is a diagram showing the structure of the translocation breakpoint region of an infant patient described herein in Example 1.

Automated sequencing of the 5' bcr in subclone 34–1 from panhandle PCR identified the MLL genomic breakpoint at nucleotide 3802 in intron 8 and partial sequence of the partner DNA, as depicted in FIG. 3. Sequencing of two additional subclones from panhandle PCR verified the MLL genomic breakpoint at nucleotide 3802.

Repeat regions in the translocation partner gene were identified and masked using the Repeat Masker program available through the Washington University Human Genome Center (at the World Wide Web address, http://ftp.genome.washington.edu/cgi-bin/mrs/mrs_reg). Masked translocation partner gene sequence was submitted for BLAST analysis against the non-repetitive nucleotide database using the server at the Japanese Genome Center at Kyoto (at the World Wide Web address, http://www.genome.ad.jp/SIT/BLAST.html). The 3'-end of the unknown partner DNA was homologous to ESTs H73415, G26138, and G29714 in the database.

Direct Sequencing of the MLL Genomic Translocation Breakpoint Region

Aliquots of genomic DNA obtained from cells of the infant patient were PCR amplified using validating primers derived from the polynucleotide product amplified by panhandle PCR. Primers which were used had nucleotide sequences 5'-GGGACTTTCT GTTGGTGGAA-3' (SEQ ID NO: 9) and 5'-GAAACACCAG CAAACCAACC-3' (SEQ ID NO: 10) or 5'-ATACATGTTG GGTGGCAGG-3' (SEQ ID NO: 11) and 5'-GTCAAGGAAA GGTGGTATAT CTCA-3' (SEQ ID NO: 12), and resulted in amplification of polynucleotides having lengths of 450 or 411 nucleotide residues, respectively. The PCR reaction mixtures each had a volume of 50 microliters and comprised 200 nanograms of genomic DNA, 0.5 unit Taq Gold™ DNA polymerase (Perkin Elmer Cetus, Norwalk, Conn.), 250 micromolar of each dNTP, PCR reaction buffer at 1×final concentration (Perkin Elmer Cetus, Norwalk, Conn.), and 5 picomoles of each of two primers. After initial denaturation and Taq Gold™ activation at 95° C. for 10 minutes, thirty-five cycles were performed by maintaining the PCR reaction mixture at 94° C. for 15 seconds, at 55° C. for 15 seconds, and at 72° C. for 1 minute. A final elongation was performed at 72° C. for 10 minutes. Amplified polynucleotide products were isolated from a 1.5% (w/v) agarose gel using a GENECLEAN II kit (BIO 101, Inc., La Jolla, Calif.). Approximately 100 nanograms of an amplified polynucleotide product was used for each direct nucleotide sequencing reaction. Sequencing was performed in both directions by automated methods. These results confirmed the MLL genomic breakpoint by an independent method.

Chromosomal Localization of the Translocation Partner Gene

Panels of somatic cell hybrid DNAs and radiation hybrid DNAs were screened by PCR to identify the chromosomal location of the translocation partner gene. For the somatic hybrid screen, the 50 microliter PCR reaction mixtures comprised 500 nanograms of the DNA to be screened (Bios Laboratories, New Haven, Conn.), 1.25 units AmpliTaq™ DNA polymerase, 200 micromolar of each dNTP, PCR reaction buffer at 1×final concentration (Perkin Elmer Cetus, Norwalk, Conn.) and 12.5 picomoles of each of two primers from the partner DNA. The region that the primers would amplify is designated S/R in FIG. 3. The primers which were used had nucleotide sequences 5'-CCTACACCCA GCCAAACTGT-3' (SEQ ID NO: 13) and 5'-ATGGTACCAG AACAGGGCAG-3' (SEQ ID NO: 14), and resulted in amplification of a polynucleotides having a length of 267 nucleotide residues. After initial denaturation at 94° C. for 9 minutes, thirty-five cycles were performed by maintaining the PCR reaction mixture at 94° C. for 1 minute, at 55° C. for 1 minute, and at 72° C. for 2 minutes. A final elongation was performed at 72° C. for 7 minutes. Human and hamster genomic DNA samples were used as controls. Twenty microliter aliquots of each PCR reaction mixture were electrophoresed in a 4% (w/v) Nusieve™ agarose gel (FMC Corp., Rockland, Me.). Amplification reactions which yielded amplified products were compared with the known human chromosome complement of the somatic hybrid panel to determine the location of the translocation partner gene.

For the radiation hybrid screen, the primers used were the same as those used for the somatic cell hybrid screen. The 20 microliter PCR reaction mixtures each comprised 25 nanograms of the DNA to be screened from the Stanford G3 radiation hybrid panel (Research Genetics, Huntsville, Ala.), 0.5 unit Taq Gold™ DNA polymerase (Perkin Elmer Cetus, Norwalk, Conn.), 250 micromolar of each dNTP, PCR reaction buffer at 1×final concentration (Perkin Elmer Cetus, Norwalk, Conn.), and 5 picomoles of each of two primers. After initial denaturation and Taq Gold activation at 95° C. for 10 minutes, a two-phase touchdown protocol for annealing and extension was used. In the first phase, sixteen cycles were performed by maintaining the PCR reaction mixture at 95° C. for 45 seconds, and at 70° C. for 1 minute (decreasing by 0.7° C./cycle) to reach a final combined annealing and extension temperature of 59° C. In the second phase, twenty-six cycles were performed by maintaining the PCR reaction mixture at 95° C. for 45 seconds, at 55° C. for 30 seconds, and at 72° C. for 1 minute. A final elongation was performed at 72° C. for 5 minutes. Aliquots of each PCR reaction mixture were electrophoresed in a 4% (w/v) Nusieve™ agarose gel (FMC Corp., Rockland, Me.). PCR amplification reactions which yielding an amplified polynucleotide product and reactions which did not yield an amplified polynucleotide product were scored as 1 and 0, respectively. Results were submitted to the radiation hybrid server of the Stanford Human Genome Center (at World Wide Web address http://www-shgc.stanford.edu/rhserver2/rhserver_form.html) to determine the location of the partner DNA.

The location of the translocation partner gene was further verified by FISH analysis of a subclone derived from a panhandle PCR-amplified polynucleotide product. The probe was labeled with biotin-16-dUITP and FISH analysis was performed on metaphases from peripheral blood lymphocytes obtained from a normal human male using standard methods.

The Partner DNA Originated from Chromosome Band 4q21

To determine the chromosomal location of the partner DNA, we screened panels of somatic cell hybrid DNAs and radiation hybrid DNAs by PCR. Amplification of a PCR product from cell line 803 in the somatic hybrid panel (Bios Laboratories, New Haven, Conn.) indicated that the partner DNA was from human chromosome 4. PCR amplification of radiation hybrid lines in the Stanford G3 radiation hybrid panel demonstrated that the partner DNA was in the same bin as the framework marker D4S1542 at chromosome band 4q21. The PCR primers used to screen the panels of somatic hybrid DNAs and radiation hybrid DNAs were from a more 5' region of the partner DNA than the 255 bp region of homology to existing sequences of ESTs H73415, G26138 and G29714, as depicted in FIG. 3. Thus, the chromosome band 4q21 location of the ESTs independently corroborated the location of the partner DNA.

For further verification of the location of the partner DNA, a subclone containing the genomic breakpoint junction was used as probe in FISH analysis. The probe consisted of 3651 bp of MLL sequence extending from the nested forward primer to the translocation breakpoint, 3224 bp of sequence from the partner gene, and an additional 75 bp of MLL sequence extending from the ligated phosphorylated oligonucleotide through the reverse nested primer used for PCR. Twenty metaphases from human peripheral blood lymphocytes of a normal male were examined. Signal was detected on at least one chromosome 11 in 9 of 20 cells. Signal was detected at proximal 4q in 5 of 20 cells. Due to the small size of the probe, signal was not detected in every cell. More importantly, however, there was no significant hybridization elsewhere in the genome. These data are consistent with a location of the partner DNA at chromosome band 4q21 and indicate that panhandle PCR amplified a genomic translocation breakpoint involving MLL and partner DNA from chromosome band 4q21.

RT-PCR Analysis

RT-PCR analysis was performed to evaluate whether translocation fused MLL with AF-4. The Superscript™ Preamplification System (Gibco BRL, Gaithersburg, Md.) and random hexamers were used for synthesis of cDNA from 4 micrograms of total RNA obtained from the same infant, according to the manufacturer's directions. The 100 microliter RT-PCR reaction mixtures comprised 2 microliters of a random hexamer-primed cDNA preparation, 2.5 units of AmpliTaq™ DNA polymerase (Perkin Elmer Cetus, Norwalk, Conn.), 200 micromolar of each dNTP, PCR reaction buffer at 1×final concentration (Perkin Elmer Cetus, Norwalk, Conn., and 100 picomoles of each primer. The primers were derived from MLL exon 6 and from the AF-4 gene, and have been described (primers MLLEx6S and LTG4AS2 respectively; Yamamoto et al., 1994, Blood 83:2912–2921). After initial denaturation at 95° C. for 2 minutes, thirty-five cycles were performed by maintaining the PCR reaction mixture at 95° C. for 1 minutes, at 62° C. for 2 minutes, and at 72° C. for 1 minutes. A final elongation was performed at 72° C. for 10 minutes. A second round of RT-PCR was performed using a 2 microliter aliquot of the first RT-PCR reaction mixture as the template. Primers and conditions were the same, except that the annealing temperature was 65° C. The cell line RS4:11, which is known to have an MLL genomic breakpoint within intron 7 and to yield a 627-nucleotide-residue polynucleotide product when amplified using these primers, was the positive control (Yamamoto et al., 1994, Blood 83:2912–2921).

Polynucleotide products amplified by RT-PCR were electrophoresed in VisiGel™ Separation Matrix (Stratagene, Inc., La Jolla, Calif.), and aliquots of these products were electrophoresed in 1% (w/v) agarose and purified for nucleotide sequencing using a GENECLEAN III™ kit (Bio 101, Inc., La Jolla, Calif.). Seventy nanograms of purified polynucleotide were used for direct automated sequencing using standard methods and the same primers as those used for RT-PCR.

RT-PCR Analysis Indicates MLL-AF-4 Chimeric mRNA

Since the partner DNA originated from chromosome band 4q21, RT-PCR analysis was performed on randomly primed cDNA from the leukemic cells of patient 38 to evaluate whether the translocation joined MLL to AF-4. Initial and second round RT-PCR reactions with sense and antisense primers from MLL and AF-4, respectively, showed the predicted 627 bp product in the positive control cell line RS4:11 (Yamamoto et al., 1994, Blood 83:2912–2921). In the leukemia of patient 38, initial and second round reactions gave a single 741 bp product. Direct sequencing of the products of four separate second round reactions showed an in-frame fusion of MLL exon 8 to the AF-4 gene at position 1459 of the AF-4 cDNA (Nakamura et al., 1993, Proc. Natl. Acad. Sci. USA 90:4631–4635). These data indicate that the unknown partner DNA that panhandle PCR had amplified was from a previously uncharacterized region of the AF-4 gene.

The Translocation Partner Gene is Homologous with EST H73415

The nucleotide sequence of portions of subclones derived from panhandle PCR-amplified polynucleotide products were identical to known sequences of ESTs H73415, G26138 and G29714. The entire EST H73415 was obtained and sequenced (Genome Systems, St. Louis, Mo.) from the Soares human fetal liver and spleen cDNA library (dbEST Id:375797), in both directions. The EST was 1034 nucleotide residues in length. The EST was homologous with portions of subclones derived from panhandle PCR-amplified polynucleotide products. The homology was in 1033 of 1034 nucleotide residues and extended through an AluJ$_o$ sequence into a region of unique non-repetitive sequence, where the EST subclone ended. Neither the sequence of the amplified portion of the translocation partner gene in the full length products of panhandle PCR, nor the region of homology with EST H73415, contained intron-exon boundaries or shared homology with full-length AF-4 cDNA. These results suggest that the portion of the translocation partner gene which comprised the unknown region of the panhandle PCR-amplified polynucleotide product was derived from a previously uncharacterized intronic region of AF-4.

Automated Sequencing of EST H73415

EST H73415 (Genome Systems, St. Louis, Mo.), which was derived from the Soares human fetal liver spleen cDNA library (dbEST Id:375797), was obtained as a bacterial stab in the vector pT7T3D-Pac and isolated as individual colonies from a Luria broth agar plate containing 100 micrograms per milliliter ampicillin in the agar. The entire EST was sequenced in both directions using a T3 sequencing primer and sequencing primers used to characterize the translocation partner gene.

Summary of Findings by Panhandle PCR in this Example

The translocation partner DNA comprised unique non-repetitive sequences, Alu and MaLR (mammalian apparent LTR-retrotransposon) repetitive sequences, and a region having homology with known expressed sequence tags (ESTs) H73415, G26138, G29714 of the Human Genome Database. A diagram of the translocation breakpoint region of the MLL gene of the infant patient is shown in FIG. 3.

MaLR sequences have not previously been associated with leukemia-associated translocation breakpoints. The non-repetitive sequences were not homologous to any known partner gene of MLL. Screening of somatic cell hybrid and radiation hybrid lines by PCR and fluorescent in situ hybridization (FISH) analyses of normal metaphase chromosomes mapped the translocation partner DNA to chromosome band 4q21. Reverse transcriptase PCR (RT-PCR) identified an MLL-AF-4 chimeric mRNA, which indicated that a fusion of MLL with a previously uncharacterized intronic region of AF-4 had occurred. This Example of basic panhandle PCR amplification of a MLL genomic breakpoint region demonstrated that the method is useful for identifying an unknown translocation partner gene of MLL.

The nucleotide sequence of a portion of the gene sequence obtained from the unknown region of the amplified polynucleotide product derived from the infant patient described in this Example is listed in FIG. 5 (SEQ ID NO: 1). The antisense sequence corresponding to this portion of the gene sequence is listed in FIG. 6 (SEQ ID NO: 2). A conglomerate nucleotide sequence derived from numerous subclones of the amplified polynucleotide product derived from the infant patient described in this Example is listed in FIG. 7 (SEQ ID NO: 3). This conglomerate nucleotide sequence begins at the 5'-BamHI site, and extends through the MLL derived sequence to the 3'-BamHI site. A subsequently corrected sequence was deposited with GenBank (Accession Number AF031403), and is listed in FIG. 4 (SEQ ID NO: 23).

Examples 2 and 3

Panhandle PCR Amplifies MLL Genomic Breakpoints in Treatment-related Leukemias

Panhandle PCR amplifies genomic DNA with known 5' and unknown 3' sequences. We used panhandle PCR to clone MLL genomic breakpoints in one case each of treatment-related acute lymphoblastic leukemia (t-ALL) (Example 2) and treatment-related acute myeloid leukemia (t-AML) (Example 3). By adding sequence to the unknown 3' partner DNA that was complementary to a known MLL 5' sequence and intrastrand annealing, we were able to generate the genomic template with an intrastrand loop for panhandle PCR. The methodology was exactly as describe above as in Example 1 for MLL genomic breakpoint cloning in the case of infant ALL, except that the amount of Taq/Pwo used was 1.75 units and 5 min rather than 7 min was used for annealing/elongation in the PCR reactions because the target sequences were smaller.

Example 2

Figure 8:
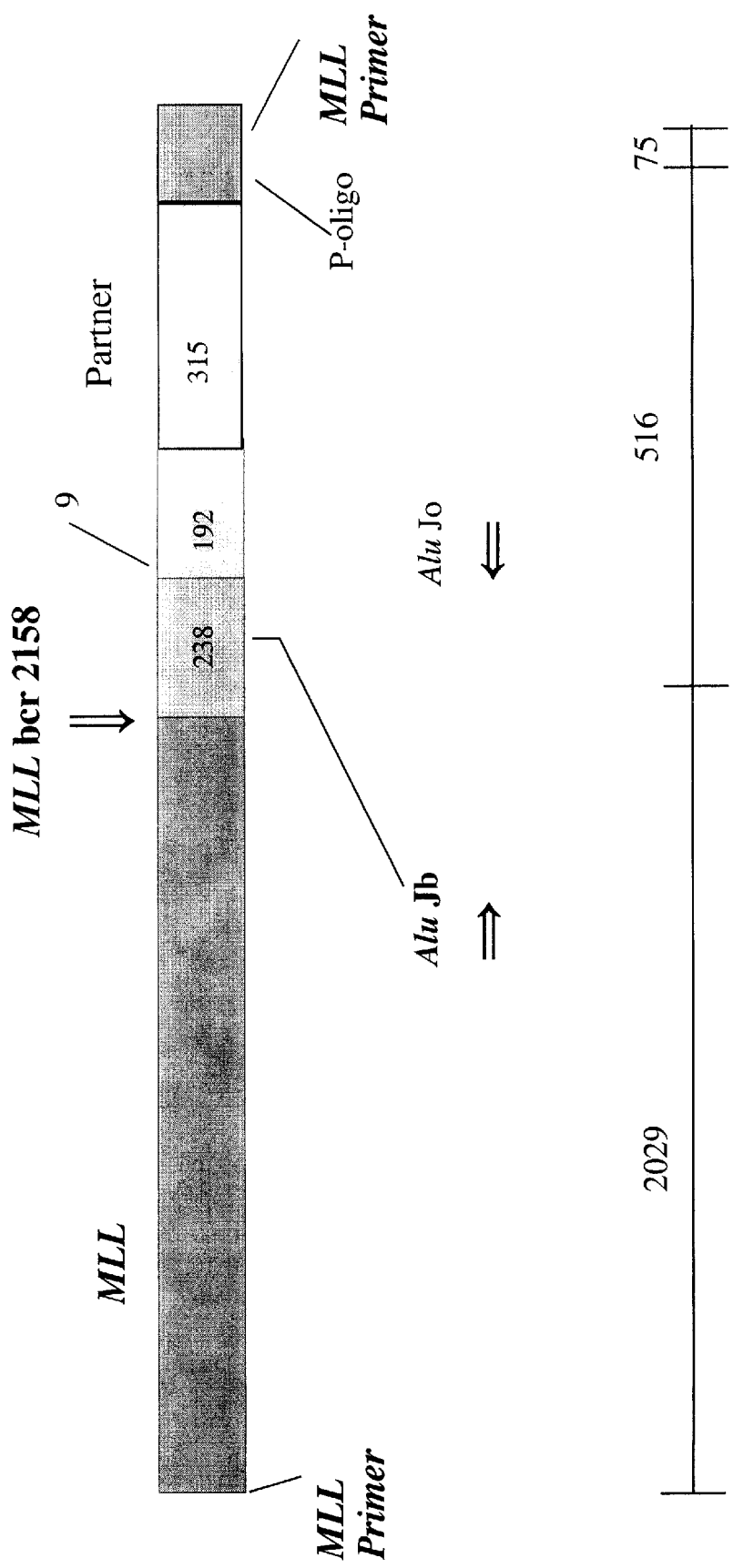
FIG. 8 is a diagram showing the structure of the MLL translocation breakpoint region of the DNA of the patient described in Example 2.

Southern blot analysis of the ALL of patient 33 with the t(4;11)(q21; q23) revealed 7 kb and 2.5 kb rearrangements. Panhandle PCR products 2620 bp in size indicated that the 2.5 kb restriction fragment on Southern blot analysis was from the der(11) chromosome. Automated sequencing of three subclones of these products identified the MLL genomic breakpoint at nucleotide 2158 in intron 6 in the 5' bcr, as depicted in FIG. 8. For further confirmation of the breakpoint sequence, genomic DNA from the leukemic cells was amplified with a primer set encompassing the translocation breakpoint. Direct sequencing verified that nucleotide 2158 was the breakpoint in the MLL bcr.

Sequences of the breakpoint and the partner DNA 3' of the breakpoint were the same in all three subclones. The breakpoint in MLL was within an Alu element of the J subfamily. Five hundred sixteen bp of sequence 3' of the breakpoint represented partner DNA, followed by sequences of the ligated oligonucleotide and the reverse primer used for nested PCR. The partner DNA also contained an AluJ that began 9 bp downstream from translocation breakpoint. The more 3' sequence of the partner DNA was rich in short poly-A and poly-T repeats.

Consistent with the karyotype, screening of the Stanford G3 radiation hybrid panel with PCR primers from the partner DNA indicated that the nearest linked marker to the partner DNA was D4S1542 at chromosome band 4q21. These results validated the panhandle PCR method in a treatment-related leukemia where the cytogenetic location of the partner DNA was known.

Although the leukemia showed a t(4;11)(q21; q23) translocation, the non-repetitive partner DNA sequences did not share homology with known genomic sequences of AF-4. However, screening of radiation hybrid panel DNAs previously indicated that the nearest linked marker to the AF-4 gene was also D4S1542, suggesting that the partner DNA in the treatment-related ALL was derived from either AF-4 or from a genomic sequence in close proximity to AF-4.

We performed RTPCR analysis as described for the case of infant ALL above. RT-PCR analysis showed that the t(4;11) was an MLL-AF-4 fusion, indicating that the partner DNA in the products of panhandle PCR was another previously uncharacterized AF-4 intronic sequence.

In summary, the karyotype in the t-ALL showed t(4;11) (q21; q23). Panhandle PCR amplified the translocation breakpoint at position 2158 in intron 6 in the 5' MLL genomic breakpoint cluster region (bcr). The sequence of the partner DNA was not homologous to cDNA or genomic sequences of the AF-4 gene at chromosome band 4q21, the most common partner gene of MLL in ALL. Nonetheless, RT-PCR analysis showed that the t(4;11) was an MLL-AF-4 fusion, indicating that the partner DNA in the products of panhandle PCR was another previously uncharacterized AF-4 intronic sequence.

Example 3

Panhandle PCR Identifies MLL Partial Duplication in Treatment-related AML with 46, XY Karyotype In the AML of patient 13 where the karyotype was 46, XY, Southern blot analysis revealed a single 3.5 kb rearrangement in BamHI digested DNA. Panhandle PCR products 3446 bp in size were obtained, consistent with the single rearrangement on Southern blot analysis. Sequencing of a subclone identified the breakpoint at position 1493 in intron 6 of the MLL bcr. PCR amplification of genomic DNA from the leukemic cells with a primer set encompassing the breakpoint and direct genomic sequencing confirmed that nucleotide 1493 was the rearrangement breakpoint in the MLL bcr.

Figure 9:
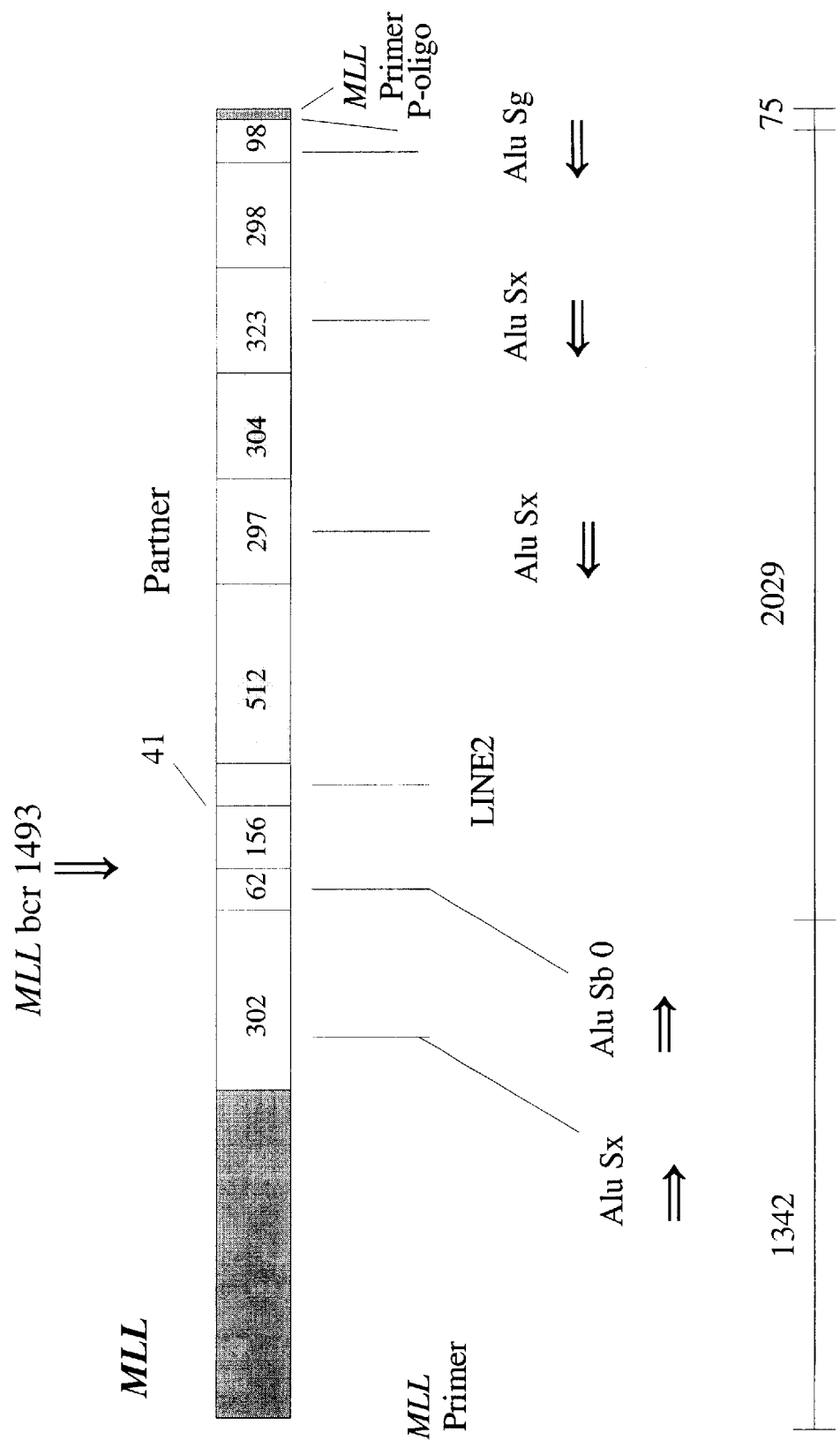
FIG. 9 is a diagram showing the structure of the MLL translocation breakpoint region of the DNA of the patient described in Example 3.

The breakpoint in MLL intron 6 was within an AluS repeat, as depicted in FIG. 9. Two thousand twenty-nine bp of sequence 3' of the breakpoint were from partner DNA, followed by sequences of the ligated oligonucleotide and the reverse primer used for nested PCR. The partner DNA contained four unique sequence regions, one LINE2 and three additional AluS repeats. The breakpoint in the partner DNA was in a unique sequence region.

Single rearrangements on Southern blot analysis sometimes indicate partial duplication of several exons of the MLL gene (Schichman et al., 1994, Proc. Natl. Acad. Sci. USA 91:6236–6239; Nakao et al., 1996, Leukemia 10:1911–1918). However, the partner DNA did not share homology with known genomic sequences of MLL and the small size of the rearranged BamHI fragment was not consistent with other partial duplications analyzed with BamHI (Schichman et al., 1994, Proc. Natl. Acad. Sci. USA 91:6236–6239; Caligiuri et al., 1996, Cancer Res. 56:1418–1425; So et al., 1997, Cancer Res. 57:117–122; Yamamoto et al., 1997, Am. J. Hematol. 55:41–45). To determine the chromosomal location of the partner DNA, panels of somatic cell hybrid DNAs and radiation hybrid DNAs were screened by PCR. Amplification of a PCR product from cell line 1049 in the somatic cell hybrid panel (Bios Laboratories) indicated that the partner DNA was on human chromosome 11. PCR amplification of radiation hybrid lines in the Stanford G3 radiation hybrid panel showed that the partner sequence was in the same bin as the framework marker D11S2060 at chromosome band 11q23.3.

Figure 10:
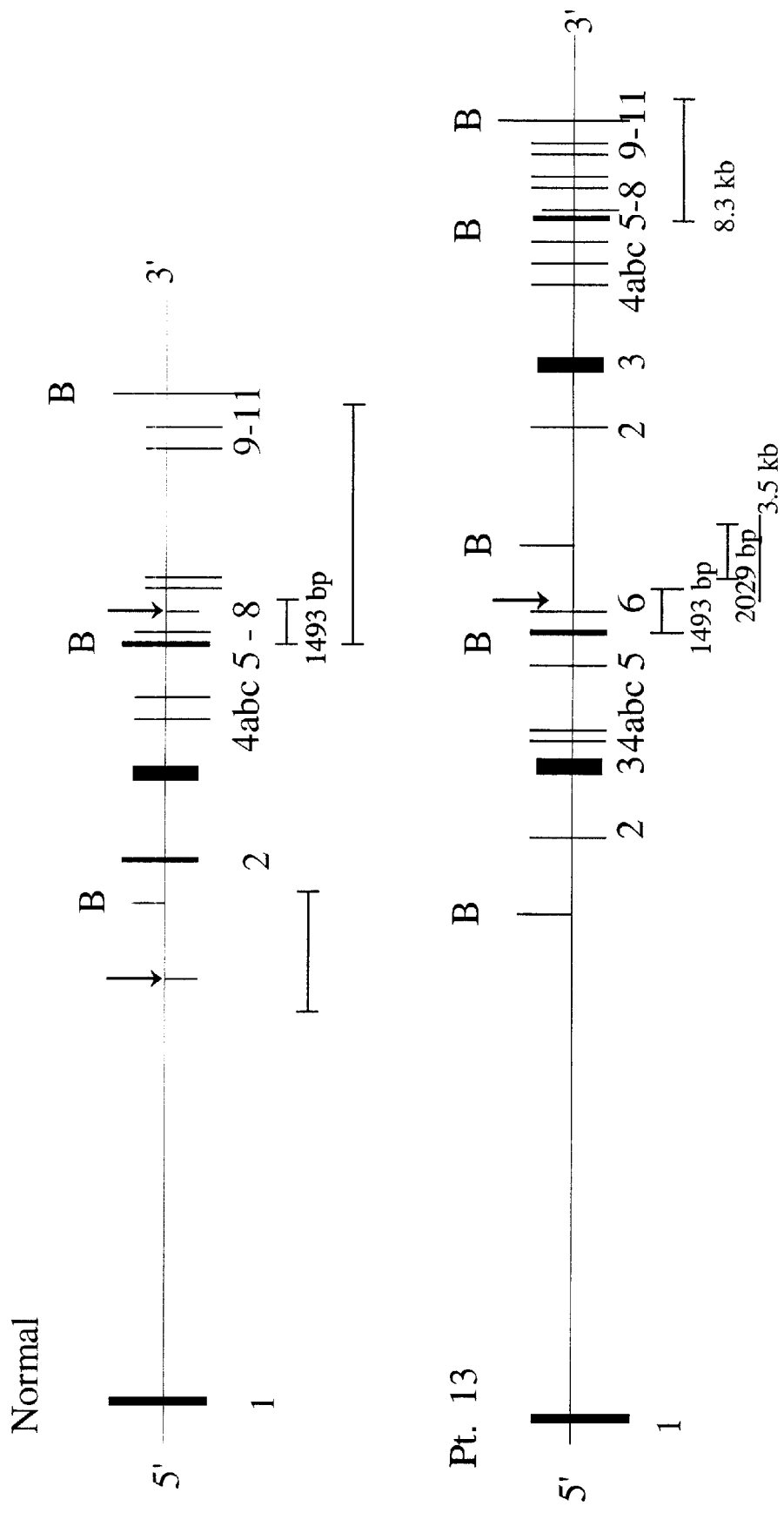
FIG. 10 is a diagram showing the structure of the MLL gene in the DNA of a normal human in the upper portion of the Figure and the structure of the MLL gene in the DNA of the second patient described in Example 3 in the lower portion. Numbers below the structures indicate exon numbers, and the shaded portion represents a portion of the structure of the MLL gene which was duplicated in the DNA of the second patient. BamHI sites are indicated by "B".

RT-PCR analysis was performed on total RNA from the leukemic cells to evaluate whether the fusion was an MLL partial duplication. Nested RT-PCR reactions with sense and antisense primers from MLL exon 6 and exon 3, respectively, gave a single 228 bp product. Direct sequencing of the products of three separate nested RT-PCR reactions revealed an in-frame fusion of exon 6 to exon 2, indicating that panhandle PCR identified an MLL partial duplication that joined intron 6 with intron 1, 2029 bp upstream of the intron 1 BamHI restriction site, as indicated in FIG. 10.

In summary, in Example 3 the karyotype in the t-AML was normal, but Southern blot analysis showed a single MLL gene rearrangement. Panhandle PCR amplified the breakpoint at position 1493 in MLL intron 6, also in the 5' bcr. Screening of somatic cell hybrid and radiation hybrid DNAs by PCR and RT-PCR analysis of the leukemic cells indicated that panhandle PCR identified a fusion of MLL intron 6 with a previously uncharacterized sequence in MLL intron 1, consistent with a partial duplication.

In both the t-ALL of Example 2 and the t-AML of Example 3, the breakpoints in the MLL bcr were in Alu repeats and there were Alu repeats near the breakpoints in the partner DNAs, suggesting that the repetitive sequences were important for these rearrangements. Analysis of additional pediatric cases will determine whether breakpoint distribution deviates from the predilection for 3' distribution in the bcr that has been found in adult cases. These results show that panhandle PCR is an effective method for cloning MLL genomic breakpoints in treatment-related leukemias. Panhandle PCR may be the prototypic PCR approach for identification of translocation breakpoints where the 3' sequence of the partner gene is undetermined and materials are limited. In all 3 cases described so far, the sequence of the partner DNA was previously uncharacterized intronic sequence of a known partner gene of MLL, showing the power of this method to characterize new genomic sequences flanking translocation breakpoints.

The GenBank accession numbers for sequences in examples 2 and 3 are AF024540–AF024543 and the sequence are shown in FIGS. 11–14 (SEQ ID NOs: 15–18).

Example 4

Recombination PCR Simplifies Cloning of MLL Genomic Breakpoint Regions by Panhandle PCR Conventional subcloning methods involve ligations of the ends of panhandle PCR products with ends of linearized plasmid, followed by transformation of E. coli. Subcloning of panhandle PCR products was simplified by using recombination PCR in place of conventional subcloning methods. Recombination PCR has been described (Jones et al., 1991, BioTechniques 10:62–66).

To subclone panhandle PCR products by recombination PCR, a PCR reaction was performed using a HindIII-digested plasmid template (pUC19) to generate a linearized plasmid polynucleotide having ends complementary to the ends of the panhandle PCR-amplified polynucleotide products. PCR products from both PCR reactions are combined, undergo in vivo recombination after transformation of E. coli. Recombinant plasmid, which comprised a panhandle PCR-amplified polynucleotide product, were identified by PCR, rather than by preparing and digesting minipreps, as in conventional methods.

Example 5

Recombination PCR was used in conjunction with panhandle PCR to characterize the breakpoint regions in two infant patients afflicted with ALL, each of whom exhibited t(4;11). In both of these patients, similar MLL rearrangements were identified, the rearrangements being 9.5 kilobases and 3.2 kilobases in size. Based on these observations, it appeared that the translocation breakpoint regions of the MLL genes of the two patients might be similar. In one of the two patients, panhandle PCR amplification generated a polynucleotide product 3.2 kilobases in length. When recombination PCR was used for retrieval and detection of the MLL genomic breakpoint region of this patient, ten of seventeen subclones generated in three separate panhandle PCR reactions were observed to comprise the desired 3.2 kilobase polynucleotide product. Nucleotide sequencing of the subclones identified the genomic breakpoint at position 1737 of the bcr of MLL, in MLL intron 6, at a position 21 nucleotides 3' with respect to an AluSbO repeat sequence. The breakpoint in the translocation partner DNA of this patient was located 3 nucleotides 5' with respect to a LINE2 repeat. Furthermore, GG, TTT, AG and TG nucleotide sequences were present on both sides of the breakpoint junction, suggesting that base pairing and homologous end-joining are involved in the translocation process.

Panhandle PCR amplification of DNA obtained from leukemic cells of the other patient generated a polynucleotide product 3.2 kilobases in length. When recombination PCR was used for retrieval and detection of the MLL genomic breakpoint region, seventeen of twenty-four subclones comprised the 3.2 kilobase insert. Nucleotide sequencing of the subclones identified the genomic breakpoint at position 914 of the bcr of MLL, in MLL intron 6 and within an AluJ repeat. An AluJ$_b$ repeat was located 32 nucleotides 3' with respect to the breakpoint in the partner gene. As in the other patient, GGG, CT, TT, and AA nucleotide sequences were present at both sides of the breakpoint junction. Although the breakpoint regions in the translocation partner DNAs of these two patients were different, overlapping nucleotide sequences in the subclones placed them in the same intronic region. The sizes of the rearrangements detected by genomic Southern blot analysis of these two patients and the locations of BamHI sites in AF-4 were consistent with the presence of genomic breakpoints in AF-4 intron 3 in both cases.

Example 6

Panhandle Variant PCR Amplified an MLL Genomic Breakpoint Region in a Patient Afflicted with Treatment-related MDS Involving an Unknown Partner Gene The variant panhandle PCR described herein was used to clone the MLL genomic breakpoint region of a patient afflicted with treatment-related myelodysplastic syndrome (MDS). The patient was diagnosed at 13 years 9 months of age with a monocytic preleukemia, 11 months after the start of treatment for primary neuroblastoma. The patient's neuroblastoma treatment involved administration of DNA topoisomerase II inhibitors, alkylating agents, and radiation. The patient's marrow karyotype indicated a del(11q23) during the period of preleukemia, which lasted for six months before onset of overt FAB M4 AML. Although the karyotype indicated del(11q23), detection of two MLL gene rearrangements by Southern blot analysis indicated that translocation had occurred.

The variant panhandle PCR method described in this Example was used to amplify the unknown translocation partner DNA sequence which was present at the breakpoint region of the der(11) chromosome. This method amplified a polynucleotide product having a length of 6.0 kilobases. Recombination PCR was performed to retrieve and detect the MLL genomic breakpoint region. Nucleotide sequencing of the subclones identified the genomic breakpoint at position 4664 of the bcr of MLL, in MLL intron 8. The nucleotide sequence of the translocation partner DNA was not homologous to any known partner gene of MLL, suggesting that the translocation partner DNA was either a previously uncharacterized intronic region of a known translocation partner gene of MLL or a novel translocation partner gene. Screening of somatic cell hybrid and radiation hybrid lines by PCR was performed to determine the chromosomal location of the translocation partner DNA. This suggested that the partner DNA was from chromosome 17. Thirty-four of the sixty-eight subclones from four variant panhandle PCR reactions comprised the desired insert, which was 6.0 kilobases in size. These results demonstrate the usefulness of the variant panhandle PCR method for cloning a translocation breakpoint region comprising a portion of an unknown partner gene. In addition, it shows that a long product was obtained by this technique.

Example 7 t(11;22)(q23; q11.2) in Acute Myeloid Leukemia of Infant Twins Fuses MLL with hCDCrel, a Cell Division Cycle Gene in the Common Region of Deletion in DiGeorge and Velocardiofacial Syndromes Case Histories Patient 68 presented at 11½ months of age with fever, bruising, thrombocytopenia, WBC of 228×10$^9$/liter and leukemia in the central nervous system. The bone marrow was replaced by blasts of French-American-British (FAB) M2 morphology that expressed CD33 and CD45. The G-banded karyotype was 46, XX,t(11;22)(q23; q11.2)[15], while fluorescence in situ hybridization (FISH) analysis with an MLL-specific probe (Oncor) showed hybridization with the normal chromosome 11 and split signals on the der(11) chromosome and chromosome 22. The patient was a monozygous twin. Seven weeks later, the twin of patient 68, designated patient 72, was also diagnosed with AML. Patient 72 presented with bruising and WBC of 20.6×10$^9$/l. There were 67% abnormal blasts of FAB M1 morphology on marrow differential. The blasts expressed HLA-DR, CD 13 and CD33. The G-banded karyotype of the diagnostic marrow was 46, XX[5]/46, XX,t(11;22)(q23; q11)[15]. On fluorescence in situ hybridization analysis, the MLL-specific probe hybridized with the normal and der(11) chromosomes and chromosome 22, suggesting that the t(11;22)(q23; q11.2) disrupted MLL.

Southern Blot Analysis Identifies Identical MLL Gene Rearrangements in Infant Twins We examined peripheral blood mononuclear cells from patient 68 and leukemic marrow cells from patient 72 for MLL gene rearrangement at times of diagnosis. In both cases, the B859 probe showed the 8.3 kb germline band and identical, rearranged BamHI restriction fragments 3.8 kb and 6.3 kb in size, indicating chromosomal translocation. Pre-diagnosis peripheral blood mononuclear cells were obtained from patient 72 at time of diagnosis of leukemia in her twin. On two-week exposure, Southern blot analysis of the pre-diagnosis specimen detected both the germline band and faint 3.8 kb and 6.3 kb rearrangements, showing presence of cells with the translocation before clinical leukemia appeared. The intensity of the rearrangements relative to the germline band increased from pre-diagnosis to the time of diagnosis.

Panhandle PCR Variant Amplifies MLL Genomic Translocation Breakpoint

We first implemented panhandle variant PCR to clone the MLL genomic breakpoint on the der(11) chromosome in the leukemia of patient 68. Six independent panhandle PCR variant reactions yielded products ~3.9 kb in size, indicating that the 3.8 kb rearrangement on Southern blot analysis was from the der(11) chromosome. There was sufficient material for direct genomic sequencing of the translocation breakpoint junction without subcloning the products of panhandle variant PCR. In addition, to confirm the translocation breakpoint and obtain additional information on the partner DNA, we performed recombination PCR using the products of one panhandle variant PCR reaction. Six of eight recombination PCR-generated subclones contained the desired 3.9 kb insert and we sequenced two subclones in their entirety.

The t(11;22)(q23; q11.2) Fuses MLL with hCDCrel, a Cell Division Cycle Gene in the Common Region of Deletion in DiGeorge and Velocardiofacial Syndromes Direct automated sequencing of the products of panhandle variant PCR identified the genomic breakpoint at nucleotide 2672 in MLL intron 7 and provided partial sequence of the partner DNA. Sequencing of the subcloned products confirmed the translocation breakpoint and yielded additional sequence of the partner gene. A BLAST search against the nucleotide database indicated that the sequence of the partner DNA at chromosome band 22q11.2 was identical to an intronic region of the hCDCrel (human cell division cycle related) gene (Accession No. 000093), which is a member of a gene family involved in cell division cycle that includes the Drosophila peanut-like protein 1 gene. The hCDCrel gene maps to the central portion of a 1.3 Mb sequence contig on chromosome band 22q11.2 that is commonly deleted in DiGeorge and velocardiofacial syndromes.

Figure 15:
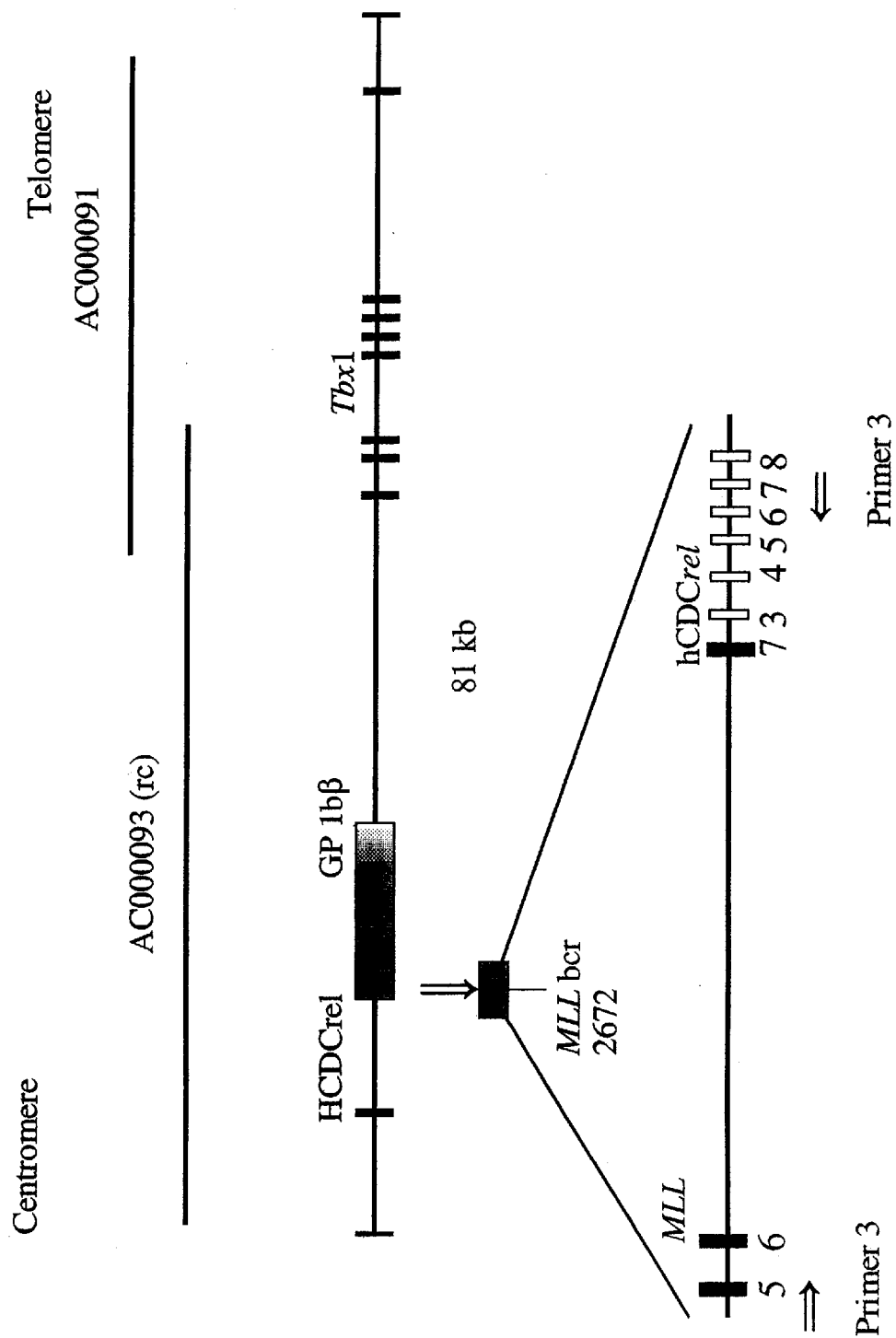
FIG. 15 is a diagram of a translocation breakpoint junction region described herein in Example 7.

Comparison of the cDNA to the genomic sequence indicates that hCDCrel contains 11 exons that span approximately 9 kb. The genomic breakpoint in hCDCrel in the leukemia of patient 68 was in intron 2 at nucleotide 26510 relative to cosmid carlaa (Accession No. 000093), although the orientation of the GenBank entry (Accession No. 000093) is in opposite orientation to the open reading frame of the cDNA. Consistent with the size of the rearrangement on Southern blot analysis, and with the size of the panhandle variant PCR product, the next BamHI site in the hCDCrel gene 3' of the translocation breakpoint is located in exon 8 at position 25275 of cosmid carlaa (Accession No. 000093). Thus, 2622 bp of sequence in the panhandle variant PCR product were from MLL and 1240 bp were from hCDCrel. FIG. 15 depicts the translocation breakpoint junction region of the der(11) chromosome in relation to the chromosome band 22q11.2 genomic region. The region of the genomic breakpoint in hCDCrel was rich in simple repeats and low complexity repeats. Both MLL and hCDCrel contained homologous CT, TTTGTG and GAA sequences within a few base pairs of their respective breakpoints.

Independent Confirmation of MLL Genomic Breakpoint in Leukemia of Patient 68

To detect the translocation breakpoint by a method that was independent of panhandle variant PCR, we amplified fresh aliquots of genomic DNA from the leukemic cells of patient 68 with primers encompassing the translocation breakpoint, which were designed from sequences of the products of panhandle variant PCR. Four independent PCR reactions gave the predicted 344 bp product. Direct sequencing was performed on the products of two reactions and verified the translocation breakpoint.

RT-PCR Analysis Shows MLL-hCDCrel Chimeric mRNA

Since the partner DNA originated from hCDCrel at chromosome band 22q11.2, we performed RT-PCR analysis on randomly primed cDNA from the leukemic cells of patient 68 to evaluate whether the translocation produced a fusion mRNA. The RT-PCR reaction performed with sense and antisense primers from MLL exon 6 and hCDCrel exon 3, respectively, gave the predicted 247 bp product. Direct sequencing of the products of RT-PCR showed an in-frame fusion of MLL exon 7 to hCDCrel exon 3 at position 142 of the 2032 bp full-length hCDCrel cDNA (Accession No.U74628).

Panhandle Variant PCR Amplifies Identical MLL Genomic Translocation Breakpoint in AML of Patient 72

We also used panhandle variant PCR to isolate the translocation breakpoint junction in the AML of patient 72, the twin of patient 68. The products of one panhandle variant PCR reaction were subcloned by recombination PCR. The desired 3.9 kb insert was present in 6 of 7 subclones and two positive subclones were sequenced in entirety. The sequence showed the same MLL intron 7 breakpoint at nucleotide 2672 and the same hCDCrel partner DNA as in the leukemia of patient 68. For independent confirmation, we amplified fresh aliquots of genomic DNA from the leukemic cells of patient 72 with primers encompassing the breakpoint junction. Four independent PCR reactions gave the predicted 344 bp product. We directly sequenced the products of two of the reactions, which verified the translocation breakpoint.

Summary and Significance of Findings in AML of Infant Twins

Using panhandle variant PCR technology, we determined that the t(11;22)(q23; q11.2) in concordant AMLs of monozygous infant twins was the result of fusion of MLL with hCDCrel and identified a new partner gene of MLL at chromosome band 22q11.2. The panhandle variant PCR results were validated independently by direct genomic sequencing of products of conventional PCR and by RT-PCR analysis. The genomic sequence of the partner DNA at the translocation breakpoint junction of the der(11) chromosome was identical to intron 2 of the hCDCrel gene at chromosome band 22q11.2 (Accession No. 000093). hCDCrel is a member of a gene family involved in cell division cycle that includes the Drosophila peanut-like protein 1 gene. The hCDCrel gene contains 11 exons that span approximately 9 kb and yields two transcripts of 2.5 and ~3.5 kb (16). The smaller transcript terminates at an imperfect polyadenylation site, while the longer transcript is produced by the alternative use of the polyadenylation site of Glycoprotein (GP) Ibβ, the adjacent 3' gene. The putative protein product of hCDCrel is a GTP-binding protein.

The hCDCrel gene is in the central portion of a 1.3 Mb sequence contig, which is part of the region on chromosome band 22q11.2 commonly deleted in both DiGeorge and velocardiofacial syndromes. DiGeorge syndrome is a constitutional disorder characterized by cardiac anomalies, thymic and parathyroid hypoplasia and dysmorphic craniofacial features, while the major features of velocardiofacial syndrome are palatal and cardiac defects, facial dysmorphia and learning disabilities. hCDCrel is the second partner gene of MLL located in a region of the genome involved in both leukemia and a constitutional disorder. In 1996, Borrow et al. determined that the t(8;16)(p11;p13) of AML represents a fusion of the MOZ and CBP (CREB-binding protein) genes. Shortly afterwards, Taki et al. and Sobulo et al. demonstrated that CBP is the partner gene of MLL in myelodysplastic syndrome with the t(11;16)(q23; p13.3). CBP encodes a histone acetyltransferase that functions as a transcriptional coactivator. The Rubinstein-Taybi syndrome, a constitutional disorder that includes mental retardation, dysmorphic facial features, and broad thumbs and toes, is characterized by chromosomal translocations, microdeletions and point mutations of the CBP gene. Thus, there is some precedent for involvement of the same region of the genome in both developmental abnormalities as well as in leukemia.

We detected short homologous sequences two to six bp in length at the breakpoint junctions in both MLL and hCDCrel. Similarly, we found short segments of homology between MLL and AF-4 or AF-9 at t(4;11) and t(9;11) breakpoint junctions. On the basis of these findings, we proposed that base pairing of homologous DNA ends of MLL and partner gene is one step in the translocation process. In addition, the cloning of a constitutional balanced t(2;22)(q14; q11.21) translocation associated with DiGeorge syndrome identified several small segments of nucleotides (~6 bp) repeated on chromosomes 2 and 22, suggesting that the same phenomenon may occur in constitutional and somatic translocations.

The t(11;22)(q23; q11.2) that fused MLL with hCDCrel in the leukemias of infant twins is distinct from the constitutional t(11;22)(q23; q11) translocation, which is the most frequent, recurrent, non-Robertsonian translocation in humans. In the constitutional t(11;22), the phenotype is normal and the translocation is present in all cells. Furthermore, the breakpoints at chromosome band 11q23 in the constitutional recurrent translocations map proximal to leukemia-associated translocation breakpoints involving MLL. Two lines of evidence argue that the t(11;22)(q23; q11.2) that we observed was not constitutional. In patient 72 where serial samples were available, the intensity of MLL gene rearrangements relative to the germline band on Southern blot analysis progressively increased from pre-diagnosis to the time of diagnosis. Furthermore, the karyotype of the diagnostic marrow of patient 72 revealed 5 of 20 cells in which the karyotype was normal.

Concordance of the unique, clonal, non-constitutional MLL gene rearrangements suggests that the t(11;22) occurred in utero and that there was metastasis from one twin to the other via the placenta. The ages of the two twins at diagnosis of leukemia were similar, 11.5 months and 13 months. Within pairs of twins, the ages at onset of leukemia have generally been concordant, suggesting similar times of latency before disease is evident. The delineation of MLL gene rearrangements in twins as in utero events complements research efforts on prenatal exposures to environmental toxins as etiologic factors in leukemia in infants. One line of investigation involves maternal dietary DNA topoisomerase II inhibitors, since leukemias in infants resemble treatment-related leukemias linked to chemotherapy that targets DNA topoisomerase II. Moreover, the latency to onset of disease suggests a potential role for secondary alterations in addition to the translocations, but the influence of various translocation partners on sufficiency of MLL gene translocations for full leukemogenesis has not been addressed.

Using panhandle variant PCR, we amplified a 3.9 kb product, identified the t(11;22) translocation breakpoint and distinguished hCDCrel as a new partner gene of MLL in AML of infant twins. The method was devised to simplify the PCR-based cloning of genomic DNAs with unknown 3' flanking sequences, precisely the situation with many MLL genomic breakpoints. Beyond the finding of a new partner gene of MLL, this work introduces a particular PCR technology that expedites translocation breakpoint cloning. We recently used the original panhandle PCR as another strategy to clone MLL genomic breakpoints. Although the names are similar because the genomic template in both cases has an intrastrand loop schematically shaped like a pan with a handle, panhandle variant PCR is distinct from the original panhandle PCR. Table 1 lists several salient differences between the original panhandle PCR and panhandle variant PCR. Both strategies offer advantages over conventional genomic cloning and conventional long-range PCR, which requires specific primers for the many partner genes of MLL. Increased use of both methods will test whether one or the other is more advantageous in specific situations. Furthermore, for retrieval and detection of the MLL genomic breakpoint, we employed recombination PCR, which uses *E. coli* itself to mediate DNA recombination and obviates the ligation step in subcloning.

Including the hCDCrel gene identified in the present work, 13 partner genes of MLL have been cloned to date. In addition, MLL may fuse with self in partial tandem duplications. The joining of the MLL breakpoint cluster region and several different partner genes renders molecular cloning of MLL genomic breakpoints by PCR more difficult. Panhandle variant PCR offers a new strategy to surmount the challenge of cloning MLL genomic breakpoints where the partner genes are many and often undetermined. Identification of a genomic region at chromosome band 22q11.2 involved in AML and in the constitutional DiGeorge and velocardiofacial syndromes also is of interest.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of amplifying an unknown region of a translocation partner which flanks a section of the breakpoint cluster region of a leukemia-associated MLL gene, the method comprising:
   (a) providing a template polynucleotide comprising a sense strand which comprises the section and the unknown region, wherein the unknown region is nearer the 3' end of the sense strand than is the section, wherein the section comprises a first portion and a second portion, and wherein the first portion is nearer the unknown region than is the second portion;
   (b) ligating a loop-forming oligonucleotide to the 3'-end of the sense strand, wherein the loop-forming oligonucleotide is complementary to the first portion;
   (c) annealing the loop-forming oligonucleotide with the first portion to generate a panhandle structure;
   (d) subjecting the panhandle structure to extension, whereby an additional region complementary to the second portion is generated at the free end of the loop-forming oligonucleotide; and
   (e) subjecting the panhandle structure to PCR in the presence of a first primer homologous with the second portion, whereby the unknown region is amplified.

2. The method of claim 1, wherein the section comprises a portion of an exon of MLL selected from the group consisting of exon 5 and exon 11.

3. The method of claim 1, wherein the loop-forming oligonucleotide has a nucleotide sequence comprising SEQ ID NO: 4.

4. The method of claim 1, wherein the first primer has a nucleotide sequence selected from the group consisting of SEQ ID NOs: 5–8.

5. The method of claim 1, wherein the panhandle structure is subjected to PCR in the presence of the first primer and further in the presence of a second primer, wherein the second primer is nested with respect to the first primer.

6. The method of claim 5, wherein each of the first primer and the second primer independently has a nucleotide sequence selected from the group consisting of SEQ ID NOs: 5–8.

7. The method of claim 1, wherein the template polynucleotide further comprises an antisense strand, wherein the 5'-end of the antisense strand overhangs the 3'-end of the sense strand, and wherein a portion of the loop-forming oligonucleotide is complementary to the overhanging region of the antisense strand.

8. The method of claim 1, wherein the template polynucleotide is provided by
   obtaining genomic DNA from a patient;
   contacting the genomic DNA with a restriction endonuclease, whereby a genomic DNA fragment is generated, the genomic DNA fragment comprising the section and the unknown region, whereby the genomic DNA is the template polynucleotide.

9. A variant method of amplifying an unknown region of a translocation partner which flanks a section of the breakpoint cluster region of a leukemia-associated MLL gene, the method comprising:
   (a) providing a template polynucleotide comprising an antisense strand which comprises a region complementary to the section and a region complementary to the unknown region, wherein the region complementary to the unknown region is nearer the 5'-end of the antisense strand than is the region complementary to the section, wherein the section comprises a first portion and a second portion, and wherein the first portion is nearer the unknown region than is the second portion;
   (b) ligating a first oligonucleotide to the 5'-end of the antisense strand, wherein the first oligonucleotide is homologous with the first portion;
   (c) annealing a pre-template polynucleotide with the antisense strand, the pre-template polynucleotide being homologous with the second portion;
   (d) subjecting the pre-template polynucleotide to extension, whereby a sense strand is generated, the sense strand comprising the section, the unknown region, and a loop-forming oligonucleotide at the 3'-end thereof, the loop-forming oligonucleotide being complementary to the first portion;
   (e) annealing the loop-forming oligonucleotide with the first portion to generate a panhandle structure;
   (f) subjecting the panhandle structure to extension, whereby an additional region complementary to the second portion is generated at the free end of the loop-forming oligonucleotide; and (g) subjecting the panhandle structure to PCR in the presence of a first primer homologous with the second portion, whereby the unknown region is amplified.

10. The method of claim 9, wherein, prior to ligating the first oligonucleotide to the antisense strand, a bridging oligonucleotide is annealed with a portion of the antisense strand adjacent the 5'-end thereof and the first oligonucleotide is annealed with the bridging oligonucleotide.

11. A method of identifying a translocation partner of a leukemia-associated MLL gene, the translocation partner comprising an unknown region, and the gene comprising a known breakpoint cluster region, the method comprising (a) providing a template polynucleotide comprising a sense strand which comprises the known region and the unknown region, wherein the unknown region is nearer the 3' end of the sense strand than is the known region, wherein the known region comprises a first portion and a second portion, and wherein the first portion is nearer the unknown region than is the second portion;

(b) ligating a loop-forming oligonucleotide to the 3' end of the sense strand, wherein the loop-forming oligonucleotide is complementary to the first portion;

(c) annealing the loop-forming oligonucleotide with the first portion to generate a panhandle structure;

(d) subjecting the panhandle structure to extension, whereby an additional region complementary to the second portion is generated at the free end of the loop-forming oligonucleotide; and (e) subjecting the panhandle structure to PCR in the presence of a first primer homologous with the second portion, whereby the unknown region is amplified; and (f) identifying a portion of a human DNA sequence homologous with the unknown region, whereby the human DNA sequence is identified as the translocation partner.

12. A variant method of identifying a translocation partner of a leukemia-associated MLL gene, the translocation partner comprising an unknown region, and the gene comprising a known region, the method comprising (a) providing a template polynucleotide comprising an antisense strand which comprises a region complementary to the section and a region complementary to the unknown region, wherein the region complementary to the unknown region is nearer the 5'-end of the antisense strand than is the region complementary to the section, wherein the section comprises a first portion and a second portion, and wherein the first portion is nearer the unknown region than is the second portion;

(b) ligating a first oligonucleotide to the 5'-end of the antisense strand, wherein the first oligonucleotide is homologous with the first portion;

(c) annealing a pre-template polynucleotide with the antisense strand, the pre-template polynucleotide being homologous with the second portion;

(d) subjecting the pre-template polynucleotide to extension, whereby a sense strand is generated, the sense strand comprising the section, the unknown region, and a loop-forming oligonucleotide at the 3'-end thereof, the loop-forming oligonucleotide being complementary to the first portion;

(e) annealing the loop-forming oligonucleotide with the first portion to generate a panhandle structure;

(f) subjecting the panhandle structure to extension, whereby an additional region complementary to the second portion is generated at the free end of the loop-forming oligonucleotide; and (g) subjecting the panhandle structure to PCR in the presence of a first primer homologous with the second portion, whereby the unknown region is amplified.

13. A kit for panhandle PCR amplification of an unknown region of a translocation partner which flanks a known region in the breakpoint cluster region of a strand of a leukemia associated MLL gene, the kit comprising an oligonucleotide consisting of the nucleic acid sequence of SEQ ID NO: 4; and a primer selected from the group consisting of SEQ ID NOS 5–8.

14. The kit of claim 13, further comprising a restriction endonuclease;

a reagent for ligating the oligonucleotide to a DNA strand obtained from a human patient;

a reagent for extending a polynucleotide; and a reagent for performing PCR.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 3336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
GGATCCGGAA AAGAGTGAAG AAGGGAATGT CTCGGCCCCT GGGCCTGAAT CCAAACAGGC      60

CACCACTCCA GCTTCGATCC TGGCTCTAGG GGATGAGGAT GAAAGGAGCC AGGGCAGAGG     120

CTGAGGTGCT GTCCACCAGG AAAGTGCTGA TAAACCTTCA GGGTTGGGTT GAGAATGCCT     180

CCAAGATACC CCTCAAGTCA AGCCATTTAT TAGACAAGAA GAAGGAACAA AAAACCTTTC     240

CCTGTGGAGA GTTCCAGGGC TGAGAGGGGA AAGTAAAGAC AGGCCATGTC AGTACTACCC     300

TTCTCCTTGT CTCTCCCTAC CTGTTTTTGT TTTTGTTTTT GTTTTGAGAC AGGGTCTCAC     360

TGTGTTGCCC AGGCTGGAGT TCACTGGTGC AATCATATAG CTCACTGTAA CCTCAAGCTC     420

TTGAGCTGAA GTGATCCTCT CACCTCAGCC TCCTCAGCAG CTAAGACTAC AAGCACACAC     480

ACCATTATGC TCAGCTAATT GTTAAATATT TATAGGGATG GGGGCGGTC TATGTTGCCT      540

AGGCTAGTCT CAAAACTCCT GGCCTACAGT AATCCTCCCA CCTCAGCCTG GCATGACCCC     600

CTACACCCAG CCAAACTGTC CCATTACAGA GTCTGCAGGG CAATGACCGG TCACTAGAAA     660

GCCAAACATC AGGGCTTACT TAACCAACTA ATAAAGCATT ATTAAAATTT TCTCCATTCT     720

AAGGCTTTTG ATGAGACCTG CTTATTAGGA TGGATGTCAC GATCTTGGCC CACAGTGCCA     780

ATCAATAAGT AAAAATGATT AGGTCTACAA GCAATGGAAA CATGGGTATT ATCATGCAGT     840

GAAACCCTGC CCTGTTCTGG TACCATGAAG GAAATCTCCA TGAACCCTGT GTCATCTTCA     900
```

```
CCTCTGAAAA TGTTTGAACA GACTCCAGCC TCAATCTCCT TTGAACCTAT ATATCTAATA    960

ACCTGCTGGC ATAGTTAAAA ATAAATTTAA AAGTTATCAT CATAAAAGCC TTCTAAAAAC   1020

TATTCCTCAC TCAAGAAAAA TTTCTACAGG ATGGTATTAG CAGGAGCAGC AGTAGTCAGT   1080

ACCAAAAACA TTTATTAAGG GGCAGAGAGG TTGCACAGAG AAAGGGGGGG GAAAAATAAT   1140

GGGCAAAATT TAATTCTCAA CTGTTTAAGT TCTTTAAGCA CAAGGAAGCC ATCCGCTGGT   1200

AAGGCAAGAA AATGTTTAAA ATTACCTCCG GCCTAAAACT TATTTTTCTT CTGACACTGC   1260

CCCATCTTTA ACCAGTCTTT CCTCCATGAT ATGAGGACAG TCCAAAACAG TTTTTCCCAA   1320

ACTTCGGTCA TTTCTATACT ACTTTGATAG CGGCACTGCG TCATAATACT ACTTGTACTA   1380

TTTTTTTAGA TCAGTTTATG ATCAACCCAC TTTTTTTTTT TAACCTCACC TCATCCTAAG   1440

CAATATTTGT GAAACCCTAG GTTTGTTTGA TATGCTGGTT TATATTTCTT CCTAATTCAC   1500

ATGACATGAT TTGGCTGTGT CCCCACCCAA ATCTCATCTT GAATTCCCAT GTGTTGTGGG   1560

AGGGAGCTGG TGGGAGGTAA TTCGATCATG GGGGCAGGTC TTTCCCGTGC TGTTCTTGTA   1620

ACAGTGAGTC TCATGAGATC TGATGGTTTT AAAAACAGGA GTTTCCCTGC ACAACCTCTC   1680

TCTTTGCCGC CACTCACGTA GACGTGACCT GCTCCTCCTT GCCTTCCGCA TGACTGTGAG   1740

GCTTCCATGT GGAACTGTGA GTTCTCCACT AAACCTCTTT CCTTTGTAAA TTGCCCAGTC   1800

TCAGGTATGT CTTTATCAGC AGTGTGAAAG CAGACTAATG CACCACATTA AGACACATAA   1860

AATAAAGGTT GGTGTCCCCA CACTATATTA TTTTTTCTTG TGACAGAGTC TGTCAGCCAG   1920

GCTGGAGTGC AGTGGCACGA ACACAGCTCA CTGCAGCCTA CACTTCCTGT GCTCAAGTGA   1980

TCCTCCTACC TCAGCCTCCT GAGCAGCTGG GACCGCAGGT GCATGCCACA ACACCCGGCT   2040

TTTTTTTTTT TTTCTTTTGA GACGGAATTT CACTCTTGTT GCCCAGGCTG GAGTGCAATG   2100

ACGCGATCTC GACTTTACTG CAACCTCCGC TTCCTGGGTT CAAGCAATTC TCCTTCCTCA   2160

GCCTCCTGAG GATTACAGGC ACCCACCACC ATGCCTGGCT AATTTTTGCA TTTTTAGTAG   2220

AGACAGGGTT TCACCCTGTT GCCCAGGCTG GTCTCGAATT CCTGACCTCA GATGATCCAC   2280

CCACCTCAGC CTCCCAAAGT GCTGAGATTA TAGACATGAG CCACCGTGCC CAGCCGCTAA   2340

TTTTTAAAAT GTTTTGTAGA GACAGTCTCA CCATGTTGTC CAGGTTGGTC TCAAACTCCT   2400

GGGCTCGAGG AATCCTCCTG CCTCGGCTTC CCAAAGTGTT GGGATTACAG GCGTGAGCCA   2460

CTGTGCCTGG CCTCCATACT ATTTTAAAGA AGTTTATATA CTCATCAATA CTATGTGAAC   2520

CAAAAACTGA ATGAATATCT TGGGACATTC CAGCTTCCTA CCCTGTAAAA CCATCTTACT   2580

CTATCAGTCA ATACAAATGT TGCCTATCTT CTATATTGGA TTCAGGAACC TTCAGAGATT   2640

CCATGAAAAT ATGTTTAATC TTACACCTTT CCTTACTAAA TTTGTGACCC AGGTCACAGA   2700

ATTAACACTT TATACATCAG TGTTCAGTTC AGTACTATAA TTTTTTCTAT TTGTCACAAT   2760

GCTCAAATGT GACGGGCTC AAAAAGCCCT TTACACACTA GCCCTTGCCC CATATACTTC   2820

TCACAACTAA TGCAATTCTG GAATCCTGAA ACTACAGCAA GTATTCAGTA CTTTATTAGG   2880

GCATAAAATA TCTATTCAAG TCTCTTATTG AAAAGTGTA ACATTTAAAA ACTTGACTAA   2940

AATTAAATCC ATGACACAGA GTTTCATTAC TTCATCACAA CAACTGTGAA ACACCAGCAA   3000

ACCAACCTAA AACACAAAGA TATTTCTTGG GATTCTGCTG ACTTCTAGGC ACAGCTGTAA   3060

CATCTATACA GACTACTTGA AGATGGATAA TATACAATTT TCCTACAGCA TAAATTTTCT   3120

TTTACTAACA CAATATGTCA AGGAAAGGTG GTATATCTCA CAATATACTA AATGTCAGGC   3180

AAACATATCC CATTTAATTC TCACAACAGC CCTCTAGCTC AGGAAATACT GTCCCATTTA   3240
```

| | |
|---|---|
| AATGTGAAGT AGAATGAACC CATGCATTCT AACTCCATAG CTCTGTCCAT TAGAAACATT | 3300 |
| ATTTCCCACT CATATTTTCT TAAAGCCATA ATATTC | 3336 |

(2) INFORMATION FOR SEQ ID NO:2:

(i) SEQUENCE CHARACTERISTICS:
        (A) LENGTH: 3336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

| | |
|---|---|
| GAATATTATG GCTTTAAGAA AATATGAGTG GGAAATAATG TTTCTAATGG ACAGAGCTAT | 60 |
| GGAGTTAGAA TGCATGGGTT CATTCTACTT CACATTTAAA TGGGACAGTA TTTCCTGAGC | 120 |
| TAGAGGGCTG TTGTGAGAAT TAAATGGGAT ATGTTTGCCT GACATTTAGT ATATTGTGAG | 180 |
| ATATACCACC TTTCCTTGAC ATATTGTGTT AGTAAAAGAA AATTTATGCT GTAGGAAAAT | 240 |
| TGTATATTAT CCATCTTCAA GTAGTCTGTA TAGATGTTAC AGCTGTGCCT AGAAGTCAGC | 300 |
| AGAATCCCAA GAAATATCTT TGTGTTTTAG GTTGGTTTGC TGGTGTTTCA CAGTTGTTGT | 360 |
| GATGAAGTAA TGAAACTCTG TGTCATGGAT TTAATTTTAG TCAAGTTTTT AAATGTTACA | 420 |
| CTTTTTCAAT AAGAGACTTG AATAGATATT TTATGCCCTA ATAAAGTACT GAATACTTGC | 480 |
| TGTAGTTTCA GGATTCCAGA ATTGCATTAG TTGTGAGAAG TATATGGGGC AAGGGCTAGT | 540 |
| GTGTAAAGGG CTTTTTGAGC CCCGTCACAT TTGAGCATTG TGACAAATAG AAAAAATTAT | 600 |
| AGTACTGAAC TGAACACTGA TGTATAAAGT GTTAATTCTG TGACCTGGGT CACAAATTTA | 660 |
| GTAAGGAAAG GTGTAAGATT AAACATATTT TCATGGAATC TCTGAAGGTT CCTGAATCCA | 720 |
| ATATAGAAGA TAGGCAACAT TTGTATTGAC TGATAGAGTA AGATGGTTTT ACAGGGTAGG | 780 |
| AAGCTGGAAT GTCCCAAGAT ATTCATTCAG TTTTTGGTTC ACATAGTATT GATGAGTATA | 840 |
| TAAACTTCTT TAAAATAGTA TGGAGGCCAG GCACAGTGGC TCACGCCTGT AATCCCAACA | 900 |
| CTTTGGGAAG CCGAGGCAGG AGGATTCCTC GAGCCCAGGA GTTTGAGACC AACCTGGACA | 960 |
| ACATGGTGAG ACTGTCTCTA CAAAACATTT TAAAAATTAG CGGCTGGGCA CGGTGGCTCA | 1020 |
| TGTCTATAAT CTCAGCACTT TGGGAGGCTG AGGTGGGTGG ATCATCTGAG GTCAGGAATT | 1080 |
| CGAGACCAGC CTGGGCAACA GGGTGAAACC CTGTCTCTAC TAAAAATGCA AAAATTAGCC | 1140 |
| AGGCATGGTG GTGGGTGCCT GTAATCCTCA GGAGGCTGAG GAAGGAGAAT TGCTTGAACC | 1200 |
| CAGGAAGCGG AGGTTGCAGT AAAGTCGAGA TCGCGTCATT GCACTCCAGC CTGGGCAACA | 1260 |
| AGAGTGAAAT TCCGTCTCAA AAGAAAAAAA AAAAAAAGCC GGGTGTTGTG GCATGCACCT | 1320 |
| GCGGTCCCAG CTGCTCAGGA GGCTGAGGTA GGAGGATCAC TTGAGCACAG GAAGTGTAGG | 1380 |
| CTGCAGTGAG CTGTGTTCGT GCCACTGCAC TCCAGCCTGG CTGACAGACT CTGTCACAAG | 1440 |
| AAAAAATAAT ATAGTGTGGG GACACCAACC TTTATTTTAT GTGTCTTAAT GTGGTGCATT | 1500 |
| AGTCTGCTTT CACACTGCTG ATAAAGACAT ACCTGAGACT GGGCAATTTA CAAAGGAAAG | 1560 |
| AGGTTTAGTG GAGAACTCAC AGTTCCACAT GGAAGCCTCA CAGTCATGCG GAAGGCAAGG | 1620 |
| AGGAGCAGGT CACGTCTACG TGAGTGGCGG CAAAGAGAGA GGTTGTGCAG GGAAACTCCT | 1680 |
| GTTTTTAAAA CCATCAGATC TCATGAGACT CACTGTTACA AGAACAGCAC GGGAAAGACC | 1740 |
| TGCCCCCATG ATCGAATTAC CTCCCACCAG CTCCCTCCCA CAACACATGG GAATTCAAGA | 1800 |
| TGAGATTTGG GTGGGACAC AGCCAAATCA TGTCATGTGA ATTAGGAAGA AATATAAACC | 1860 |

-continued

| | |
|---|---|
| AGCATATCAA ACAAACCTAG GGTTTCACAA ATATTGCTTA GGATGAGGTG AGGTTAAAAA | 1920 |
| AAAAAAGTGG GTTGATCATA AACTGATCTA AAAAAATAGT ACAAGTAGTA TTATGACGCA | 1980 |
| GTGCCGCTAT CAAAGTAGTA TAGAAATGAC CGAAGTTTGG GAAAAACTGT TTTGGACTGT | 2040 |
| CCTCATATCA TGGAGGAAAG ACTGGTTAAA GATGGGGCAG TGTCAGAAGA AAAATAAGTT | 2100 |
| TTAGGCCGGA GGTAATTTTA AACATTTTCT TGCCTTACCA GCGGATGGCT TCCTTGTGCT | 2160 |
| TAAAGAACTT AAACAGTTGA GAATTAAATT TTGCCCATTA TTTTTCCCCC CCCTTTCTCT | 2220 |
| GTGCAACCTC TCTGCCCCTT AATAAATGTT TTTGGTACTG ACTACTGCTG CTCCTGCTAA | 2280 |
| TACCATCCTG TAGAAATTTT TCTTGAGTGA GGAATAGTTT TTAGAAGGCT TTTATGATGA | 2340 |
| TAACTTTTAA ATTTATTTTT AACTATGCCA GCAGGTTATT AGATATATAG GTCAAAGGA | 2400 |
| GATTGAGGCT GGAGTCTGTT CAAACATTTT CAGAGGTGAA GATGACACAG GGTTCATGGA | 2460 |
| GATTTCCTTC ATGGTACCAG AACAGGGCAG GGTTTCACTG CATGATAATA CCCATGTTTC | 2520 |
| CATTGCTTGT AGACCTAATC ATTTTTACTT ATTGATTGGC ACTGTGGGCC AAGATCGTGA | 2580 |
| CATCCATCCT AATAAGCAGG TCTCATCAAA AGCCTTAGAA TGGAGAAAAT TTTAATAATG | 2640 |
| CTTTATTAGT TGGTTAAGTA AGCCCTGATG TTTGGCTTTC TAGTGACCGG TCATTGCCCT | 2700 |
| GCAGACTCTG TAATGGGACA GTTTGGCTGG GTGTAGGGGG TCATGCCAGG CTGAGGTGGG | 2760 |
| AGGATTACTG TAGGCCAGGA GTTTTGAGAC TAGCCTAGGA AACATAGACC GCCCCCCATC | 2820 |
| CCTATAAATA TTTAACAATT AGCTGAGCAT AATGGTGTGT GTGCTTGTAG TCTTAGCTGC | 2880 |
| TGAGGAGGCT GAGGTGAGAG GATCACTTCA GCTCAAGAGC TTGAGGTTAC AGTGAGCTAT | 2940 |
| ATGATTGCAC CAGTGAACTC CAGCCTGGGC AACACAGTGA GACCCTGTCT CAAAACAAAA | 3000 |
| ACAAAAACAA AAACAGGTAG GGAGAGACAA GGAGAAGGGT AGTACTGACA TGGCCTGTCT | 3060 |
| TTACTTTCCC CTCTCAGCCC TGGAACTCTC CACAGGGAAA GGTTTTTTGT TCCTTCTTCT | 3120 |
| TGTCTAATAA ATGGCTTGAC TTGAGGGGTA TCTTGGAGGC ATTCTCAACC CAACCCTGAA | 3180 |
| GGTTTATCAG CACTTTCCTG GTGGACAGCA CCTCAGCCTC TGCCCTGGCT CCTTTCATCC | 3240 |
| TCATCCCCTA GAGCCAGGAT CGAAGCTGGA GTGGTGGCCT GTTTGGATTC AGGCCCAGGG | 3300 |
| GCCGAGACAT TCCCTTCTTC ACTCTTTTCC GGATCC | 3336 |

(2) INFORMATION FOR SEQ ID NO:3:

(i) SEQUENCE CHARACTERISTICS:
        (A) LENGTH: 6987 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

| | |
|---|---|
| GGATCCGTGG TCATCCCGCC TCAGCCACCT ACTACGGACG CGCCAAGAAA AGAAGTTCCC | 60 |
| AAAACCACTC CTAGTGAGCC CAAGAAAAAG CAGCCTCCAC CACCAGAATC AGGTGAGTGA | 120 |
| GGAGGGCAAG AAGGAATTGC TGACCCACAA GTACTAACAA AAAAGCACTG ATGTCTCAAA | 180 |
| CAGCATTTGA AAGCAGGAAA TGTATGATTT GAAGTCTTCA GTTCAAGAAA ATCAGCTCTC | 240 |
| TTTCTAACTA TTATGTTTAA TAATAAAGAA ACAGAAACAA AAAAAACAGT TAAATTGGAG | 300 |
| GTATTGTTTT AATTTCCTGT TCGAAGCCTA GAGTTTAAAT AGTTTTTTTT TTTTTTTTCT | 360 |
| AATGGCCCTT TCTTCACAGG TCAGTCAGTA CTAAAGTAGT CGTTGCCAGC ATCTGACTGC | 420 |
| AATTTATTCT GAATTTTTTA GGTCCAGAGC AGAGCAAACA GAAAAAGTG GCTCCCCGCC | 480 |

```
CAAGTATCCC TGTAAAACAA AAACCAAAAG AAAAGGTGAG GAGAGATTTG TTTCTCTGCC    540

ATTTCTCAGG GATGTATTCT ATTTTGTAGG GAAAAGCCTT ATCCTTGACT TCTATGTAGA    600

TGGCAGTGGA ATTTCTTAAA ATTAAGAAAC TTCAAGTTTA GGCTTTTAGC TGGGCACGGT    660

GGCTCACGCT GGTAATCCCA ACACTTAGTG AGGCTGAGGT GGGAGGATTG CTTGAGGCCA    720

GCAGTTCAAG ACCAGCCTGG GCAACATAGC AAGACCCTGT CTTTATTTAA ACCAAAAAAA    780

AAAAAAGAAG AAGAAGAAGT TAGCCAGGCA TGGTGGCAGT TGCGTGTAGT CCCAGGTACT    840

CAGGAGGCTG AGATAGAAGG ATTGTCTTGA GCCCAGGAAT TCAAGGCTGT AGTGAGCTAT    900

GATTGTACCA CTGCAGTCCA GCCTGGGTGA CAAAGCAAAA CACTGTCTCC AAAAAAAATT    960

TAGGCTTGGC AAGGCGCAGC GGCTCACGCC TGTGATCCCA GCACTTTGGG AAGCCGAAGC   1020

AGGCAGATCA CTTGAGGTCA GGAGTTGGAG ACCAGCCTGG CCAACATGGT GAAACCCTGT   1080

CTCTACTGAA AATACAAAAA TTAGCCGGTT GTGGTAGTGG GTGCTTGGTA ATCCTAGCTA   1140

CTTGGGAGGC TGAGGCAGGG GGAATTGCCT GAAACCTGCG AGGCGGAGGC TGCAGTGAGC   1200

CGAGATTGCA TCATTGCACT CTAGCCTGGA CAACAGAGCT AGACTCCATC CCAAAAAAAA   1260

AAAAAAAAAG TAGCCGGGCA CGGTGGCTCA CGCCTGTAAT CCCAGCACTT TGGGAGGCCG   1320

AGGCGGGCGG ATCATGAGGG CAGGAGATCG AGACCATCCT GGCTAACACG GTGAAACCCT   1380

GTCTCTACTA AAAATACAAA AAATTAGCCC GGCGAGGTGG CGGGCGCCTG TAGTCCCAGC   1440

TACTCAGGAG AGTGAGCCAG GAGAATGGCG TGAACCCGGG GGGCGGAGCC TGCAGTGAGC   1500

CGAGATCGCG CCACTGCACT CCAGCTTGGG TGACACCGAG ACTCCGTCTC AAAAAAAAAT   1560

AAAAAGTTTA GGCTTTAGCC TGTTTCTTTT TTGGTTTCTT CCTTGTTGCT TTTCCCTTCT   1620

TTGTGGCCCC ACATGTTCTA GCCTAGGAAT CTGCTTATTC TAAAGGCCAT TTGGCGTAAT   1680

TATTTTTTGA CCCCAACATC CTTTAGCAAT TATTTGTCTG TAAAAATCAC CCTTCCCTGT   1740

ATTCACTATT TTTATTTATT ATGGATAAAG AGATAGTGTG GTGGCTCACA TCTATAATCC   1800

CAGCACTTTG GGGGCCCAAG GCGGGAGGAT CACTTGAGGG CAGGAGCTGG AGACCAGCCT   1860

GGGCAGCACA GTGACACACA GTTGCTATAA AAAATTTAAA ACCCAACTAG GCATGGTGGC   1920

ATGCACCTGT AGTCCCAGCT ACTCTTGAGA AGCTGAGGCA GGAGGATCAC GAGCCCACAA   1980

GGTCTAGGCT GCAGTGAGCT GTGACTGTGC CACTGTATTG CAGCCTAGGC AACAAAGCAA   2040

GACCCAGTCT CTTTTAAAAA AAATTCAAA GATTATTGTT TATGTTGGAA ACATGTTTTT   2100

TAGATCTATT AATAAAATTT GTCATTTGCA TTATTATCTG TTGCAAATGT GAAGGCAAAT   2160

AGGGTGTGAT TTTGTTCTAT ATTCATCTTT TGTCTCCTTA GGAAAAACCA CCTCCGGTCA   2220

ATAAGCAGGA GAATGCAGGC ACTTTGAACA TCCTCAGCAC TCTCTCCAAT GGCAATAGTT   2280

CTAAGCAAAA AATTCCAGCA GATGGAGTCC ACAGGATCAG AGTGGACTTT AAGGTAAAGG   2340

TGTTCAGTGA TCATAAAGTA TATTGAGTGT CAAAGACTTT AAATAAAGAA AATGCTACTA   2400

CCAAAGGTGT TGAAAGAGGA ATCAGCACC AACTGGGGA ATGAATAAGA ACTCCCATTA   2460

GCAGGTGGGT TTAGCGCTGG GAGAGCTTTG GACAGTGTTG TTAGGTCACT GTTTGTGAAC   2520

TGACTGCAGA ACATACATAA TGAAACATTC CTATCCATCC TGAGGAGTAT CAGAGGAAGT   2580

AATTCCTTCA CATGGAAAGT ATCAAACCAT GATGATTCCT TGAGTCAGCA AAACTGTAAG   2640

AGAAATTCAA TCCCAGTGTA TTTTCGCAAT ATCTTCACTA TGAATTGAAC AACTAGGTGA   2700

GCCTTTTAAT AGTCCGTGTC TGAGATTAAA ACTTTTTAAA GCAGCAGTTA TTTTTGGACT   2760

CATTGAAATG AAATACTCTG ACATTGTGAT GTCACACTAA TTTTATGCTT TTCATCCTTA   2820

TTTTCCATCC AAAGTTGTGT AATTGTAAAA CTTTCCTAAG TGACCTTTCT CTCTCCACAG   2880
```

```
GAGGATTGTG AAGCAGAAAA TGTGTGGGAG ATGGGAGGCT TAGGAATCTT GACTTCTGTT    2940

CCTATAACAC CCAGGGTGGT TTGCTTTCTC TGTGCCAGTA GTGGGCATGT AGAGGTAAGG    3000

CATCCTGCTT CTTTGTACCC CAGGAAGTAC ATAAATGATT GATCTGGGGA TGAGATTACT    3060

ATAGTCTGTT TTGTTGGTAT TTAGCAGGTA CTATTCCCTG TTTAAACCAG CTAAAGAAAT    3120

GTTTTGAAGT ATTTTAGAGA TTTTAGGAAG GAATCTGCTA TTAGAGTAGC AAAGTTATTG    3180

AGAGTGAAAA GATCAATAAT CCCATCTCTC TTAAATTCAG TCTTTATTAG AGTTCTGATC    3240

TTTCTGTTAG ATGTCTAAAT AAGAGAAAAA ATTATACAGT GGTCTATTAA AAGGGATGCT    3300

ATTGATGGTT ATTTTATATT GTATATCAAA GCCTCTTCAT CTATAAGGAG CTCTTACCAA    3360

TTAATAAGAA AAAGGAATGA CATCCAGAAA AAAAAATAGG CAAAGACAG AAATAGATAA     3420

TTCACAAAAT TAGAAATAAA TACATGTTGG GTGGCAGGGG GAGGTGAAGG GAGGGTGTCT    3480

GTTTTTTAGC CCTCTAGTGA CCAAAAACTG GAAATTAAAG CATGATAAAA AAAGAATCCT    3540

GAATAAATGG GGACTTTCTG TTGGTGGAAA GAAATATAGA TTAGTTACAA TCTTTCTTTC    3600

TGAGGGAATT ATTTGGAAAT ATATATATCT ATCTTTAAAA TAGGTATATC CGAATATTAT    3660

GGCTTTAAGA AAATATGAGT GGGAAATAAT GTTTCTAATG GACAGAGCTA TGGAGTTAGA    3720

ATGCATGGGT TCATTCTACT TCACATTTAA ATGGGACAGT ATTTCCTGAG CTAGAGGGCT    3780

GTTGTGAGAA TTAAATGGGA TATGTTTGCC TGACATTTAG TATATTGTGA GATATACCAC    3840

CTTTCCTTGA CATATTGTGT TAGTAAAAGA AAATTTATGC TGTAGGAAAA TTGTATATTA    3900

TCCATCTTCA GTAGTCTGT ATAGATGTTA CAGCTGTGCC TAGAAGTCAG CAGAATCCCA     3960

AGAAATATCT TTGTGTTTTA GGTTGGTTTG CTGGTGTTTC ACAGTTGTTG TGATGAAGTA    4020

ATGAAACTCT GTGTCATGGA TTTAATTTTA GTCAAGTTTT TAAATGTTAC ACTTTTTCAA    4080

TAAGAGACTT GAATAGATAT TTTATGCCCT AATAAAGTAC TGAATACTTG CTGTAGTTTC    4140

AGGATTCCAG AATTGCATTA GTTGTGAGAA GTATATGGGG CAAGGCTAG  TGTGTAAAGG    4200

GCTTTTTGAG CCCCGTCACA TTTGAGCATT GTGACAAATA GAAAAAATTA TAGTACTGAA    4260

CTGAACACTG ATGTATAAAG TGTTAATTCT GTGACCTGGG TCACAAATTT AGTAAGGAAA    4320

GGTGTAAGAT TAAACATATT TTCATGGAAT CTCTGAAGGT TCCTGAATCC AATATAGAAG    4380

ATAGGCAACA TTTGTATTGA CTGATAGAGT AAGATGGTTT TACAGGGTAG GAAGCTGGAA    4440

TGTCCCAAGA TATTCATTCA GTTTTTGGTT CACATAGTAT TGATGAGTAT ATAAACTTCT    4500

TTAAAATAGT ATGGAGGCCA GGCACAGTGG CTCACGCCTG TAATCCCAAC ACTTTGGGAA    4560

GCCGAGGCAG GAGGATTCCT CGAGCCCAGG AGTTTGAGAC CAACCTGGAC AACATGGTGA    4620

GACTGTCTCT ACAAAACATT TTAAAAATTA GCGGCTGGGC ACGGTGGCTC ATGTCTATAA    4680

TCTCAGCACT TTGGGAGGCT GAGGTGGGTG GATCATCTGA GGTCAGGAAT TCGAGACCAG    4740

CCTGGGCAAC AGGGTGAAAC CCTGTCTCTA CTAAAAATGC AAAAATTAGC CAGGCATGGT    4800

GGTGGGTGCC TGTAATCCTC AGGAGGCTGA GGAAGGAGAA TTGCTTGAAC CCAGGAAGCG    4860

GAGGTTGCAG TAAAGTCGAG ATCGCGTCAT TGCACTCCAG CCTGGGCAAC AAGAGTGAAA    4920

TTCCGTCTCA AAGAAAAAA AAAAAAAGC CGGGTGTTGT GGCATGCACC TGCGGTCCCA      4980

GCTGCTCAGG AGGCTGAGGT AGGAGGATCA CTTGAGCACA GGAAGTGTAG GCTGCAGTGA    5040

GCTGTGTTCG TGCCACTGCA CTCCAGCCTG GCTGACAGAC TCTGTCACAA GAAAAAATAA    5100

TATAGTGTGG GGACACCAAC CTTTATTTTA TGTGTCTTAA TGTGGTGCAT TAGTCTGCTT    5160

TCACACTGCT GATAAAGACA TACCTGAGAC TGGGCAATTT ACAAAGGAAA GAGGTTTAGT    5220
```

```
GGAGAACTCA CAGTTCCACA TGGAAGCCTC ACAGTCATGC GGAAGGCAAG GAGGAGCAGG      5280

TCACGTCTAC GTGAGTGGCG GCAAAGAGAG AGGTTGTGCA GGGAAACTCC TGTTTTTAAA      5340

ACCATCAGAT CTCATGAGAC TCACTGTTAC AAGAACAGCA CGGGAAAGAC CTGCCCCCAT      5400

GATCGAATTA CCTCCCACCA GCTCCCTCCC ACAACACATG GGAATTCAAG ATGAGATTTG      5460

GGTGGGGACA CAGCCAAATC ATGTCATGTG AATTAGGAAG AAATATAAAC CAGCATATCA      5520

AACAAACCTA GGGTTTCACA AATATTGCTT AGGATGAGGT GAGGTTAAAA AAAAAAAGTG      5580

GGTTGATCAT AAACTGATCT AAAAAAATAG TACAAGTAGT ATTATGACGC AGTGCCGCTA      5640

TCAAAGTAGT ATAGAAATGA CCGAAGTTTG GAAAAACTG TTTTGGACTG TCCTCATATC       5700

ATGGAGGAAA GACTGGTTAA AGATGGGGCA GTGTCAGAAA AAAAATAAGT TTTAGGCCGG      5760

AGGTAATTTT AAACATTTTC TTGCCTTACC AGCGGATGGC TTCCTTGTGC TTAAAGAACT      5820

TAAACAGTTG AGAATTAAAT TTGCCCATT ATTTTTCCCC CCCCTTTCTC TGTGCAACCT       5880

CTCTGCCCCT TAATAAATGT TTTTGGTACT GACTACTGCT GCTCCTGCTA ATACCATCCT     5940

GTAGAAATTT TTCTTGAGTG AGGAATAGTT TTTAGAAGGC TTTTATGATG ATAACTTTTA     6000

AATTTATTTT TAACTATGCC AGCAGGTTAT TAGATATATA GGTTCAAAGG AGATTGAGGC     6060

TGGAGTCTGT TCAAACATTT TCAGAGGTGA AGATGCACA GGGTTCATGG AGATTTCCTT     6120

CATGGTACCA GAACAGGGCA GGGTTTCACT GCATGATAAT ACCCATGTTT CCATTGCTTG     6180

TAGACCTAAT CATTTTTACT TATTGATTGG CACTGTGGGC CAAGATCGTG ACATCCATCC     6240

TAATAAGCAG GTCTCATCAA AAGCCTTAGA ATGGAGAAAA TTTTAATAAT GCTTTATTAG     6300

TTGGTTAAGT AAGCCCTGAT GTTTGGCTTT CTAGTGACCG GTCATTGCCC TGCAGACTCT     6360

GTAATGGGAC AGTTTGGCTG GGTGTAGGGG GTCATGCCAG GCTGAGGTGG GAGGATTACT     6420

GTAGGCCAGG AGTTTTGAGA CTAGCCTAGG CAACATAGAC CGCCCCCCAT CCCTATAAAT     6480

ATTTAACAAT TAGCTGAGCA TAATGGTGTG TGTGCTTGTA GTCTTAGCTG CTGAGGAGGC     6540

TGAGGTGAGA GGATCACTTC AGCTCAAGAG CTTGAGGTTA CAGTGAGCTA TATGATTGCA     6600

CCAGTGAACT CCAGCCTGGG CAACACAGTG AGACCCTGTC TCAAAACAAA AACAAAAACA     6660

AAAACAGGTA GGGAGAGACA AGGAGAAGGG TAGTACTGAC ATGGCCTGTC TTTACTTTCC     6720

CCTCTCAGCC CTGGAACTCT CCACAGGGAA AGGTTTTTTG TTCCTTCTTC TTGTCTAATA     6780

AATGGCTTGA CTTGAGGGGT ATCTTGGAGG CATTCTCAAC CCAACCCTGA AGGTTTATCA     6840

GCACTTTCCT GGTGGACAGC ACCTCAGCCT CTGCCCTGGC TCCTTTCATC CTCATCCCCT     6900

AGAGCCAGGA TCGAAGCTGG AGTGGTGGCC TGTTTGGATT CAGGCCCAGG GGCCGAGACA     6960

TTCCCTTCTT CACTCTTTTC CGGATCC                                        6987
```

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GATCGAAGCT GGAGTGGTGG CCTGTTTGGA TTCAGG                                36
```

(2) INFORMATION FOR SEQ ID NO:5:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TCCTCCACGA AAGCCCGTCG AG                                              22

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCAAGCAGGT CTCCCAGCCA GCAC                                            24

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AGCTGGATCC GGAAAAGAGT GAAGAAGGGA ATGTCTCGG                             39

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGCTGGATCC GTGGTCATCC CGCCTCAGCC AC                                   32

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGGACTTTCT GTTGGTGGAA                                                 20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GAAACACCAG CAAACCAACC                                                20

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATACATGTTG GGTGGCAGG                                                 19

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GTCAAGGAAA GGTGGTATAT CTCA                                           24

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CCTACACCCA GCCAAACTGT                                                20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

ATGGTACCAG AACAGGGCAG                                                20

(2) INFORMATION FOR SEQ ID NO:15:

(i) SEQUENCE CHARACTERISTICS:
        (A) LENGTH: 228 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

-continued

```
GTCCAGAGCA GAGCAAACAG AAAAAAGTGG CTCCCCGCCC AAGTATCCCT GTAAAACAAA         60

AACCAAAAGA AAAGGATGAG CAATTCTTAG GTTTTGGCTC AGATGAAGAA GTCAGAGTGC        120

GAAGTCCCAC AAGGTCTCCT TCAGTTAAAA CTAGTCCTCG AAAACCTCGT GGGAGACCTA        180

GAAGTGGCTC TGACCGAAAT TCAGCTATCC TCTCAGATCC ATCTGTGT                     228
```

(2) INFORMATION FOR SEQ ID NO:16:

(i) SEQUENCE CHARACTERISTICS:
        (A) LENGTH: 495 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

```
GCAAACAGAA AAAGTGGCT CCCCGCCCAA GTATCCCTGT AAAACAAAAA CCAAAAGAAA          60

AGCAGACCTA CTCCAATGAA GTCCATTGTG TTGAAGAGAT TCTGAAGGAA ATGACCCATT        120

CATGGCCGCC TCCTTTGACA GCAATACATA CGCCTAGTAC AGCTGAGCCA TCCAAGTTTC        180

CTTTCCCTAC AAAGGACTCT CAGCATGTCA GTTCTGTAAC CCAAAACCAA AACAATATG         240

ATACATCTTC AAAAACTCAC TCAAATTCTC AGCAAGGAAC GTCATCCATG CTCGAAGACG        300

ACCTTCAGCT CAGTGACAGT GAGGACAGTG ACAGTGAACA AACCCCAGAG AAGCCTCCCT        360

CCTCATCTGC ACCTCCAAGT GCTCCACAGT CCCTTCCAGA ACCAGTGGCA TCAGCACATT        420

CCAGCAGTGC AGAGTCAGAA AGCACCAGTG ACTCAGACAG TTCCTCAGAC TCAGAGAGCG        480

AGAGCAGTTC AAGTG                                                         495
```

(2) INFORMATION FOR SEQ ID NO:17:

(i) SEQUENCE CHARACTERISTICS:
        (A) LENGTH: 3441 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

```
GGATCCGTGG TCATCCCGCC TCAGCCACCT ACTACAGGAC CGCCAAGAAA AGAAGTTCCC         60

AAAACCACTC CTAGTGAGCC AAGAAAAAG CAGCCTCCAC CACCAGAATC AGGTGAGTGA        120

GGAGGGCAAG AAGGAATTGC TGAACCACAG GTACTAACAA AAAAGCACTG ATGTCTCAAA       180

CAGCATTTGA AAGCAGGAAA TGTATGATTT GAAGTCTTCA GTTCAAGAAA ATCAGCTCTC       240

TTTCTAACTA TTATGTTTAA TAATAAAGAA ACAGAAACAA AAAACAGTT AAATTGGAGG        300

TATTGTTTTA ATTTCCTGTT CGAAGCCTAG AGTTTAAATA GTTTTTTTTT TTTTTTTCTA       360

ATGGCCCTTT CTTCACAGGT CAGTCAGTAC TAAAGTAGTC GTTGCCAGCA TCTGACTGCA       420

ATTTATTCTG AATTTTTTAG GTCCAGAGCA GAGCAAACAG AAAAAAGTGG CTCCCCGCCC       480

AAGTATCCCT GTAAAACAAA AACCAAAAGA AAAGGTGAGG AGAGATTTGT TTCTCTGCCA       540

TTTCTCAGGG GTGTATTCTA TTTTGTAGGA AAAGCCTTAT CCTTGACTTC TATGTAGATG       600

GCAGTGGAAT TCTTAAAAT TAAGAAACTT CAAGTTTAGG CTTTTAGCTG GCACGGTGG         660

CTCACGCTGG TAATCCCAAC ACTTAGTGAG GCTGAGGTGG GAGGATTGCT TGAGGCCAGC       720

AGTTCAAGAC CAGCCTGGGC AACATAGCAA GACCCTGTCT TTATTTAAAC AAAAAAAAAA       780
```

```
AAAGAAGAAG AAGAAGAAGT TAGCCAGGCA TGGTGGCAGT TGCGTGTAGT CCCAGGTACT     840
CAGGAGGCTG AGATAGAAGG ATTGCCTTGA GCCCAGGAAT TCAAGGCTGT AGTGAGCTAT     900
GATTGTACCA CTGCAGTCCA GCCTGGGTGA CAAAGCAAAA CACTGTCTCC AAAAAAAATT     960
TAGGCTTGGC AAGGCGCAGC GGCTCACGCC TGTGATCCCA GCACTTTGGG AAGCCGAAGC    1020
AGGCAGATCA CTTGAGGTCA GGAGTTGGAG ACCAGCCTGG CCAACATGGT GAAACCCTGT    1080
CTCTACTGAA AATACAAAAA TTAGCCGGTT GTGGTAGTGG GTGCTTGTAA TCCTAGCTAC    1140
TTGGGAGGCT GAGGCAGGGG AATTGCCTGA ACCTGCGAGG CGGAGGCTGC AGTGAGCCGA    1200
GATTGCATCA TTGCACTCTA GCCTGGACAA CAGAGCTAGA CTCCATCCCA AAAAAAAAAA    1260
AGTAGCCGGG CACGGTGGCT CACGCCTGTA ATCCCAGCAC TTTGGGAGGC CGAGGCGGGC    1320
GGATCATGAG GGCACCTCAT GTGAGCCACC TCGTCCTGCC CCTATACATT CTTAAAAGTA    1380
AGAATCATAT TGTGTAATTC TTTGAAGTCC CTCAGTATTT TCTACTATAG TACTATTACC    1440
ACAGTAGGTA TTTAATGTTC TTAAAACAAG TTTATTGCAT TTCTTTTATT TTCATTTTAC    1500
AAACATTTAT TGGGTGCCAA ATTTGTGCTA GATATTAGAA ATACAAAAAT GAATAGGAAA    1560
ACTGTTTCTA TCCTCAGAGT ACACACTCTA AAGAAGACAA ATGTGTGAAC ACATTTTTA     1620
AAATTCCTTC TGCTAATACT AGTAATTATG TGAGCATGTC TTTAAGGTGC AACATTAAGA    1680
CCTTGGTATT TTGAAGCTTG TAGCAGTAGC CACAAGGGGA AATGTGCCAG CTGAAGTGAT    1740
AGCTACCTGG AATAAATTCC CAAAGGGGAA GTGGTATTCT TTTTAAACTT ATCGCTGCCA    1800
AGATGCACAG TTTGCCTCCT GGATATTTCT TCAACTTTAG TTGTTCTCAG TAATTTTGTT    1860
AGTTCTCCTG TGGCCTCCTC ATTTGATGGA ATGATATATA ATGGTACTAG AAGCCTTCAA    1920
AACAAAGTAT TTCAAAAAAC AAGTGCATCA GGAGTGATTT TGATACTGTC TATGGTATTG    1980
ATGTTATTTT CAATTGATTC ATTGAAATTT GTTTTGTAAT TGAAGGGATT TGATTTTTCA    2040
AACTCTTTTT TTTCCCCCCT TTGAGACAGA GTCTTGCTCT GTTACCCAGG CTGGAGTGCA    2100
GTGCACAATC TCAGCTCACT GCAACCTCTG CCTCCTGGGT TCAAGTGATT CTTGTGCATC    2160
AGCCACCCAA GAAGCTGGGA TTAAAGGCAT GTGCCACTAT GCCCACCAAA TTTTTATTTT    2220
TGGTAGAGAC AGGGTTTCAC CATGTTGGCC AGGCTGATCT TGAACTCTGG CCTCAAGTGA    2280
TCCATCCATC TCAGCCTCCC AAAGTGCTGG GATTACAGGT GTGAGCCACC ATGCCAGGCC    2340
CTGATTTTTC ATAAGACTAA AAATTTTGGA AACAGAAGAA TGCTAAGATA TAGCTGCTAA    2400
AGGGCATGTT TGAGATGCCT ACCACTTAAT TAAGTGCTGT GAAGTACCTA GGAGTCTCTT    2460
GCTAGAAAAG GAAGGTGAGG GTGTGAGCAA AGTCATCCTA GGCTGTATTC ATCTGAGGCC    2520
AGGAGTATTG GAGCTTATTC AATAGAGGAA TTCTCAAAGT AGCTCTGGAG CCTCCATCTT    2580
AGCCTGGTAG GTAAAGAACT CTAGGCGGGT GATTTTGCT CTGACTATGG TATATTGAAA     2640
ATAATTTTTT TTTTTTGAAA TGGAGTCTTG CTCCGTTGCC CAGGCTGGAG TACAGTGGCA    2700
TGAGCTCTTG GCTCACTGCA ACCTCTACCC GGCCTCCCAA CCCCCGCCC CGGGTTCAAG     2760
CAATTCTCCT TCCTCAGCCT CCCGAGTAGC TAGGATTACA GGCGGGCACT ACCACGCCCG    2820
GCTAATTTTT GTATTTTTGG TAGAGACAGG GTTTCACCAT GTCTCTGGTC ATGTCAGGAT    2880
GGTCTCAAAC TCCTGACCTC AAGTGATCTG CCTGCCTTGG CCTCCAAAG TGCTGGGATT      2940
ACAGGCTTGA GCCACTGCCT CAGGCCCAAT TGGGAAGAAT TAAGGGAGG AACTAAAAGC     3000
TATGCATTTT AGTTGGGGAT AGGGAAGAAA ACATTACAGT TTATCAGTTG AAATTTTATC    3060
AGATCAGTGG TATTACTAGA AACTGTGTCA CATCTAGTTA CTATAGATAA TTTAGGTCTT    3120
GATTGCCTAA ACTCTGATTT CTAGCTCTGG AGTGCCTAGT TACAATACTG AGGAATGGAG    3180
```

```
ATATACATTG CCATCCTTTG GAAGAATTTT GAAATTTGAA TATTTCTCCA TGAACCACAT      3240

ACTAATATAG AAGGAAGAAT AGACTTTTTC TTTTTTCTGA GATAGGGACT TGCTTTGTCA      3300

CCCAGGCTGG AGTGCAGTGG CACGATCTCA GCCCACTGCA ACCTCCGTCC CCCAGGCTCA      3360

GGGATCGAAG CTAGAGTGGT GGCCTGTTTG GATTCAGGCC CAGGGGCCGA GACATTCCCT      3420

TCTTCACTCT TTTCCGGATC C                                               3441
```

(2) INFORMATION FOR SEQ ID NO:18:

(i) SEQUENCE CHARACTERISTICS:
      (A) LENGTH: 2598 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:18:

```
GGATCCGTGG TCATCCCGCC TCAGCCACCT ACTACAGGAC CGCCAAGAAA AGAAGTTCCC       60

AAAACCACTC CTAGTGAGCC CAAGAAAAAG CAGCCTCCAC CACCAGAATC AGGTGAGTGA      120

GGAGGGCAAG AAGGAATTGC TGAACCACAA GTACTAACAA AAAAGCACTG ATGTCTCAAA      180

CAGCATTTGA AAGCAGGAAA TGTATGATTT GAAGTCTTCA GTTCAAGAAA ATCAGCTCTC      240

TTTCTAACTA TTATGTTTAA TAATAAAGAA ACAGAAACAA AAAAAACAGT TAAATTGGAG      300

GTATTGTTTT AATTTCCTGT TCGAAGCCTA GAGTTTAAAT AGTTTTTTTT TTTTTTTCTA      360

ATGGCCCTTT CTTCACAGGT CAGTCAGTAC TAAAGTAGTC GTTGCCAGCA TCTGACTGCA      420

ATTTATTCTG AATTTTTTAG GTCCAGGGCA GAGCAAACAG AAAAAAGTGG CTCCCCGCCC      480

AAGTATCCCT GTAAAACAAA AACCAAAAGA AAAGGTGAGG AGAGATTTGT TTCTCTGCCA      540

TTTCTCAGGG ATGTATTCTA TTTTGTAGGG AAAAGCCTTA TCCTTGACTT CTATGTAGAT      600

GGCAGTGGAA TTTCTTAAAA TTAAGAAACT TCAAGTTTAG GCTTTTAGCT GGGCACGGTG      660

GCTCATGCTG GTAATCCCAA CACTTATTGA GGCTGAGGTG GGAGGATTGC TTGAGGCCAG      720

CAGTTCAAGA CCAGCCTGGG CAACATAGCA AGACCCTGTC TTTATTTAAA CCAAAAAAAA      780

AAAAGAAGA AGAAGAAGAA GTTAGCCAGG CATGGTGGCA GTTGCGTGTA GTCCCAGGTA      840

CTCAGGAGGC TGAGATAGAA GGATTGTCTT GAGCCCAGGA ATTCAAGGCT GTAGTGAGCT      900

ATGATTGTAC CACTGCAGTC CAGCCTGGGT GACAAAGCAA AACACTGTCT CCAAAAAAAA      960

TTTAGGCTTG GCAAGGCGCA GCGGCTCACG CCTGTGATCC CAGCACTTTG GGAAGCCGAA     1020

GCAGGCAGAT CACTTGAGGT CAGGAGTTGG AGACCAGCCT GGCCAACATG GTGAAACCCT     1080

GTCTCTACTG AAAATACAAA AATTAGCCGG TTGTGGTAGT GGGTGCTTGT AATCCTAGCT     1140

ACTTGGGAGG CTGAGGCAGG GAATTGCCT GAACCTGCGA GGCGGAGGCT GCAGTGAGCC     1200

GAGATTGCAT CATTGCACTC TAGCCTGGAC AACAGAGCTA GACTCCATCC CAAAAAAAA     1260

AAGTAGCCGG GCACGGTGGC TCACGCCTGT AATCCCAGCA CTTTGGGAGG CCGAGGCGGG     1320

CGGATCATGA GGGCAGGAGA TCGAGACCAT CCTGGCTAAC ACGGTGAAAC CCTGTCTCTA     1380

CTAAAAATAC AAAAAATTAG CCCGGCGAGG TGGCGGGCGC CTGTAGTCCC AGCTACTCAG     1440

GAGAGTGAGG CAGGAGAATG GCGTGAACCC GGGGGGCGGA GCCTGCAGTG AGCCGAGATC     1500

GCGCCACTGC ACTCCAGCTT GGGTGACACC GAGACTCCGT CTCAAAAAAA AATAAAAAGT     1560

TTAGGCTTTA GCCTGTTTCT TTTTTGGTTT CTTCCTTGTT GCTTTTCCCT TCTTTGTGGC     1620

CCCACATGTT CTAGCCTAGG AATCTGCTTA TTCTAAAGGC CATTTGGCGT AATTATTTTT     1680
```

```
TGACCCCAAC ATCCTTTAGC AATTATTTGT CTGTAAAAAT CACCCTTCCC TGTATTCACT      1740

ATTTTTATTT ATTATGGATA AAGAGATAGT GTGGTGGCTC ACATCTATAA TCCCAGCACT      1800

TTGGGGGGCC AAGGCGGGAG GATCACTTGA GGGCAGGAGC TGGAGACCAG CCTGGGCAGC      1860

ACAGTGACAC ACAGTTGCTA TAAAAAATTT AAAAATCAAC TAGGCATGGT GGCATGCACC      1920

TGTAGTCCCA GCTACTCTTG AGAAGCTGAG GCAGGAGGAT CACGAGCCCA CAAGGTCTAG      1980

GCTGCAGTGA GCTGTGACTG TGGCAATCTT TAGAGTTTCT CTCTCTCACC CGGGCTGGAA      2040

TGCAGTAGCA CGATCACAGC TCACTTCAGC CTTGAACTCC TGGGTCCAAG CAATGCCCAC      2100

TTTTCCATCC TGAGTAGCTA GGACTGCAGG CACATGGCAG CATGCTTGGC TGATTTATTT      2160

TTATTTTTTG TAGAGACAAG GTCTTGGGGT GTTGCCCAGG CTGAACCTGG CAATCTTATG      2220

AAGAAACACT TTAAACTCTG AAGGAAACTT TTTAAGTAAT ATAGACACAA TATTTTTGAA      2280

AAGCTCTTAA ATTGCTAAAA ATTAATGCAA AGAATAGAAT TGCTTATAGT AGCCCAAGAG      2340

GAAAGCATAA AATTGAAACT GGAAGAACTT TTTGGGTGGT ATTAATTGGA GTTGTTTTTA      2400

CTTTGTGCAT TTCACTTTCT ATTCCTTCTC GGAAATGCCA GAAGTACATT TGGTACCAGG      2460

ATGAGAAATT CCTGTTCCTC CTTGTTTTCA CACTTGAGAT GTTTGTGGAT GGTTATTGGA      2520

TCGGAAGCTG GAGTGGTGGC CTGTTTGGAT TCAGGCCCAG GGGCCGAGAC ATTCCCTTCT      2580

TCACTCTTTT CCGGATCC                                                   2598

(2) INFORMATION FOR SEQ ID NO:19:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TCCCTTCTTC ACTCTTTTCC TCGATGGCGT AATCATGGTC ATAGC                        45

(2) INFORMATION FOR SEQ ID NO:20:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TCCCTTCTTC ACTCTTTTCC TCGACATGCC TGCAGGTCGA CTCTAGAG                     48

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

ACATTCCCTT CTTCACTCTT TTCCTGGCGT AATCATGGTC ATAGC                        45
```

(2) INFORMATION FOR SEQ ID NO:22:

(i) SEQUENCE CHARACTERISTICS:
  (A) LENGTH: 41 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:22:

```
GTGGCTGAGG CGGGATGACC ACCATGCCTG CAGGTCGACT C                 41
```

(2) INFORMATION FOR SEQ ID NO:23:

(i) SEQUENCE CHARACTERISTICS:
  (A) LENGTH: 6990 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:23:

```
GGATCCGTGG TCATCCCGCC TCAGCCACCT ACTACAGGAC CGCCAAGAAA AGAAGTTCCC    60

AAAACCACTC CTAGTGAGCC CAAGAAAAAG CAGCCTCCAC CACCGAATC  AGGTGAGTGA   120

GGAGGGCAAG AAGGAATTGC TGACCCACAA GTACTAACAA AAAAGCACTG ATGTCTCAAA   180

CAGCATTTGA AAGCAGGAAA TGTATGATTT GAAGTCTTCA GTTCAAGAAA ATCAGCTCTC   240

TTTCTAACTA TTATGTTTAA TAATAAAGAA ACAGAAACAA AAAAAACAGT TAAATTGGAG   300

GTATTGTTTT AATTTCCTGT TCGAAGCCTA GAGTTTAAAT AGTTTTTTTT TTTTTTTTCT   360

AATGGCCCTT TCTTCACAGG TCAGTCAGTA CTAAAGTAGT CGTTGCCAGC ATCTGACTGC   420

AATTTATTCT GAATTTTTTA GGTCCAGAGC AGAGCAAACA GAAAAAAGTG GCTCCCCGCC   480

CAAGTATCCC TGTAAAACAA AAACCAAAAG AAAAGGTGAG GAGAGATTTG TTTCTCTGCC   540

ATTTCTCAGG GATGTATTCT ATTTTGTAGG GAAAAGCCTT ATCCTTGACT TCTATGTAGA   600

TGGCAGTGGA ATTTCTTAAA ATTAAGAAAC TTCAAGTTTA GGCTTTTAGC TGGGCACGGT   660

GGCTCACGCT GGTAATCCCA ACACTTAGTG AGGCTGAGGT GGGAGGATTG CTTGAGGCCA   720

GCAGTTCAAG ACCAGCCTGG GCAACATAGC AAGACCCTGT CTTTATTTAA ACCAAAAAAA   780

AAAAAGAAG  AAGAAGAAGT TAGCCAGGCA TGGTGGCAGT TGCGTGTAGT CCCAGGTACT   840

CAGGAGGCTG AGATAGAAGG ATTGTCTTGA GCCCAGGAAT TCAAGGCTGT AGTGAGCTAT   900

GATTGTACCA CTGCAGTCCA GCCTGGGTGA CAAAGCAAAA CACTGTCTCC AAAAAAAATT   960

TAGGCTTGGC AAGGCGCAGC GGCTCACGCC TGTGATCCCA GCACTTTGGG AAGCCGAAGC  1020

AGGCAGATCA CTTGAGGTCA GGAGTTGGAG ACCAGCCTGG CCAACATGGT GAAACCCTGT  1080

CTCTACTGAA AATACAAAAA TTAGCCGGTT GTGGTAGTGG GTGCTTGGTA ATCCTAGCTA  1140

CTTGGGAGGC TGAGGCAGGG GGAATTGCCT GAAACCTGCG AGGCGGAGGC TGCAGTGAGC  1200

CGAGATTGCA TCATTGCACT CTAGCCTGGA CAACAGAGCT AGACTCCATC CCAAAAAAAA  1260

AAAAAAAAG  TAGCCGGGCA CGGTGGCTCA CGCCTGTAAT CCCAGCACTT TGGGAGGCCG  1320

AGGCGGGCGG ATCATGAGGG CAGGAGATCG AGACCATCCT GGCTAACACG GTGAAACCCT  1380

GTCTCTACTA AAAATACAAA AAATTAGCCC GGCGAGGTGG CGGGCGCCTG TAGTCCCAGC  1440

TACTCAGGAG AGTGAGCCAG GAGAATGGCG TGAACCCGGG GGCGGAGCC  TGCAGTGAGC  1500

CGAGATCGCG CCACTGCACT CCAGCTTGGG TGACACCGAG ACTCCGTCTC AAAAAAAAAT  1560
```

```
AAAAAGTTTA GGCTTTAGCC TGTTTCTTTT TTGGTTTCTT CCTTGTTGCT TTTCCCTTCT   1620
TTGTGGCCCC ACATGTTCTA GCCTAGGAAT CTGCTTATTC TAAAGGCCAT TTGGCGTAAT   1680
TATTTTTTGA CCCCAACATC CTTTAGCAAT TATTTGTCTG TAAAAATCAC CCTTCCCTGT   1740
ATTCACTATT TTTATTTATT ATGGATAAAG AGATAGTGTG GTGGCTCACA TCTATAATCC   1800
CAGCACTTTG GGGGCCCAAG GCGGGAGGAT CACTTGAGGG CAGGAGCTGG AGACCAGCCT   1860
GGGCAGCACA GTGACACACA GTTGCTATAA AAAATTTAAA ACCCAACTAG GCATGGTGGC   1920
ATGCACCTGT AGTCCCAGCT ACTCTTGAGA AGCTGAGGCA GGAGGATCAC GAGCCCACAA   1980
GGTCTAGGCT GCAGTGAGCT GTGACTGTGC CACTGTATTG CAGCCTAGGC AACAAAGCAA   2040
GACCCAGTCT CTTTTAAAAA AAATTCAAA GATTATTGTT TATGTTGGAA ACATGTTTTT    2100
TAGATCTATT AATAAAATTT GTCATTTGCA TTATTATCTG TTGCAAATGT GAAGGCAAAT   2160
AGGGTGTGAT TTTGTTCTAT ATTCATCTTT TGTCTCCTTA GGAAAAACCA CCTCCGGTCA   2220
ATAAGCAGGA GAATGCAGGC ACTTTGAACA TCCTCAGCAC TCTCTCCAAT GGCAATAGTT   2280
CTAAGCAAAA AATTCCAGCA GATGGAGTCC ACAGGATCAG AGTGGACTTT AAGGTAAAGG   2340
TGTTCAGTGA TCATAAAGTA TATTGAGTGT CAAAGACTTT AAATAAAGAA AATGCTACTA   2400
CCAAAGGTGT TGAAAGAGGA AATCAGCACC AACTGGGGGA ATGAATAAGA ACTCCCATTA   2460
GCAGGTGGGT TTAGCGCTGG GAGAGCTTTG GACAGTGTTG TTAGGTCACT GTTTGTGAAC   2520
TGACTGCAGA ACATACATAA TGAAACATTC CTATCCATCC TGAGGAGTAT CAGAGGAAGT   2580
AATTCCTTCA CATGGAAAGT ATCAAACCAT GATGATTCCT TGAGTCAGCA AAACTGTAAG   2640
AGAAATTCAA TCCCAGTGTA TTTTCGCAAT ATCTTCACTA TGAATTGAAC AACTAGGTGA   2700
GCCTTTTAAT AGTCCGTGTC TGAGATTAAA ACTTTTTAAA GCAGCAGTTA TTTTTGGACT   2760
CATTGAAATG AAATACTCTG ACATTGTGAT GTCACACTAA TTTTATGCTT TTCATCCTTA   2820
TTTTCCATCC AAAGTTGTGT AATTGTAAAA CTTTCCTAAG TGACCTTTCT CTCTCCACAG   2880
GAGGATTGTG AAGCAGAAAA TGTGTGGGAG ATGGGAGGCT TAGGAATCTT GACTTCTGTT   2940
CCTATAACAC CCAGGGTGGT TTGCTTTCTC TGTGCCAGTA GTGGGCATGT AGAGGTAAGG   3000
CATCCTGCTT CTTTGTACCC CAGGAAGTAC ATAAATGATT GATCTGGGGA TGAGATTACT   3060
ATAGTCTGTT TTGTTGGTAT TTAGCAGGTA CTATTCCCTG TTTAAACCAG CTAAAGAAAT   3120
GTTTTGAAGT ATTTTAGAGA TTTTAGGAAG GAATCTGCTA TTAGAGTAGC AAAGTTATTG   3180
AGAGTGAAAA GATCAATAAT CCCATCTCTC TTAAATTCAG TCTTTATTAG AGTTCTGATC   3240
TTTCTGTTAG ATGTCTAAAT AAGAGAAAAA ATTATACAGT GGTCTATTAA AAGGGATGCT   3300
ATTGATGGTT ATTTTATATT GTATATCAAA GCCTCTTCAT CTATAAGGAG CTCTTACCAA   3360
TTAATAAGAA AAAGGAATGA CATCCAGAAA AAAAAATAGG CAAAAGACAG AAATAGATAA   3420
TTCACAAAAT TAGAAATAAA TACATGTTGG GTGGCAGGGG GAGGTGAAGG GAGGGTGTCT   3480
GTTTTTTAGC CCTCTAGTGA CCAAAAACTG GAAATTAAAG CATGATAAAA AAAGAATCCT   3540
GAATAAATGG GGACTTTCTG TTGGTGGAAA GAAATATAGA TTAGTTACAA TCTTTCTTTC   3600
TGAGGGAATT ATTTGGAAAT ATATATATCT ATCTTTAAAA TAGGTATATC CGAATATTAT   3660
GGCTTTAAGA AAATATGAGT GGGAAATAAT GTTTCTAATG GACAGAGCTA TGGAGTTAGA   3720
ATGCATGGGT TCATTCTACT TCACATTTAA ATGGGACAGT ATTTCCTGAG CTAGAGGGCT   3780
GTTGTGAGAA TTAAATGGGA TATGTTTGCC TGACATTTAG TATATTGTGA GATATACCAC   3840
CTTTCCTTGA CATATTGTGT TAGTAAAAGA AAATTTATGC TGTAGGAAAA TTGTATATTA   3900
TCCATCTTCA AGTAGTCTGT ATAGATGTTA CAGCTGTGCC TAGAAGTCAG CAGAATCCCA   3960
```

-continued

```
AGAAATATCT TTGTGTTTTA GGTTGGTTTG CTGGTGTTTC ACAGTTGTTG TGATGAAGTA      4020

ATGAAACTCT GTGTCATGGA TTTAATTTTA GTCAAGTTTT TAAATGTTAC ACTTTTTCAA      4080

TAAGAGACTT GAATAGATAT TTTATGCCCT AATAAAGTAC TGAATACTTG CTGTAGTTTC      4140

AGGATTCCAG AATTGCATTA GTTGTGAGAA GTATATGGGG CAAGGGCTAG TGTGTAAAGG      4200

GCTTTTTGAG CCCCGTCACA TTTGAGCATT GTGACAAATA GAAAAAATTA TAGTACTGAA      4260

CTGAACACTG ATGTATAAAG TGTTAATTCT GTGACCTGGG TCACAAATTT AGTAAGGAAA      4320

GGTGTAAGAT TAAACATATT TTCATGGAAT CTCTGAAGGT TCCTGAATCC AATATAGAAG      4380

ATAGGCAACA TTTGTATTGA CTGATAGAGT AAGATGGTTT TACAGGGTAG GAAGCTGGAA      4440

TGTCCCAAGA TATTCATTCA GTTTTTGGTT CACATAGTAT TGATGAGTAT ATAAACTTCT      4500

TTAAAATAGT ATGGAGGCCA GGCACAGTGG CTCACGCCTG TAATCCCAAC ACTTTGGGAA      4560

GCCGAGGCAG GAGGATTCCT CGAGCCCAGG AGTTTGAGAC CAACCTGGAC AACATGGTGA      4620

GACTGTCTCT ACAAAACATT TTAAAAATTA GCGGCTGGGC ACGGTGGCTC ATGTCTATAA      4680

TCTCAGCACT TTGGGAGGCT GAGGTGGGTG GATCATCTGA GGTCAGGAAT TCGAGACCAG      4740

CCTGGGCAAC AGGGTGAAAC CCTGTCTCTA CTAAAAATGC AAAAATTAGC CAGGCATGGT      4800

GGTGGGTGCC TGTAATCCTC AGGAGGCTGA GGAAGGAGAA TTGCTTGAAC CCAGGAAGCG      4860

GAGGTTGCAG TAAAGTCGAG ATCGCGTCAT TGCACTCCAG CCTGGGCAAC AAGAGTGAAA      4920

TTCCGTCTCA AAAGAAAAAA AAAAAAAAGC CGGGTGTTGT GGCATGCACC TGCGGTCCCA      4980

GCTGCTCAGG AGGCTGAGGT AGGAGGATCA CTTGAGCACA GGAAGTGTAG GCTGCAGTGA      5040

GCTGTGTTCG TGCCACTGCA CTCCAGCCTG GCTGACAGAC TCTGTCACAA GAAAAAATAA      5100

TATAGTGTGG GGACACCAAC CTTTATTTTA TGTGTCTTAA TGTGGTGCAT TAGTCTGCTT      5160

TCACACTGCT GATAAAGACA TACCTGAGAC TGGGCAATTT ACAAAGGAAA GAGGTTTAGT      5220

GGAGAACTCA CAGTTCCACA TGGAAGCCTC ACAGTCATGC GGAAGGCAAG GAGGAGCAGG      5280

TCACGTCTAC GTGAGTGGCG GCAAAGAGAG AGGTTGTGCA GGGAAACTCC TGTTTTTAAA      5340

ACCATCAGAT CTCATGAGAC TCACTGTTAC AAGAACAGCA CGGGAAAGAC CTGCCCCCAT      5400

GATCGAATTA CCTCCCACCA GCTCCCTCCC ACAACACATG GGAATTCAAG ATGAGATTTG      5460

GGTGGGGACA CAGCCAAATC ATGTCATGTG AATTAGGAAG AAATATAAAC CAGCATATCA      5520

AACAAACCTA GGGTTTCACA ATATTGCTT AGGATGAGGT GAGGTAAAAA AAAAAAAAGT      5580

GGGTTGATCA TAAACTGATC TAAAAAAATA GTACAAGTAG TATTATGACG CAGTGCCGCT      5640

ATCAAAGTAG TATAGAAATG ACCGAAGTTT GGGAAAAACT GTTTTGGACT GTCCTCATAT      5700

CATGGAGGAA AGACTGGTTA AAGATGGGGC AGTGTCAGAA GAAAAATAAG TTTTAGGCCG      5760

GAGGTAATTT TAAACATTTT CTTGCCTTAC CAGCGGATGG CTTCCTTGTG CTTAAAGAAC      5820

TTAAACAGTT GAGAATTAAA TTTTGCCCAT TATTTTTCCC CCCCCTTTCT CTGTGCAACC      5880

TCTCTGCCCC TTAATAAATG TTTTTGGTAC TGACTACTGC TGCTCCTGCT AATACCATCC      5940

TGTAGAAATT TTTCTTGAGT GAGGAATAGT TTTTAGAAGG CTTTTATGAT GATAACTTTT      6000

AAATTTATTT TTAACTATGC CAGCAGGTTA TTAGATATAT AGGTTCAAAG GAGATTGAGG      6060

CTGGAGTCTG TTCAAACATT TTCAGAGGTG AAGATGACAC AGGGTTCATG GAGATTTCCT      6120

TCATGGTACC AGAACAGGGC AGGGTTTCAC TGCATGATAA TACCCATGTT CCATTGCTT      6180

GTAGACCTAA TCATTTTTAC TTATTGATTG GCACTGTGGG CCAAGATCGT GACATCCATC      6240

CTAATAAGCA GGTCTCATCA AAAGCCTTAG AATGGAGAAA ATTTTAATAA TGCTTTATTA      6300
```

|                                                                                  |      |
| -------------------------------------------------------------------------------- | ---- |
| GTTGGTTAAG TAAGCCCTGA TGTTTGGCTT TCTAGTGACC GGTCATTGCC CTGCAGACTC                 | 6360 |
| TGTAATGGGA CAGTTTGGCT GGGTGTAGGG GGTCATGCCA GGCTGAGGTG GGAGGATTAC                 | 6420 |
| TGTAGGCCAG GAGTTTTGAG ACTAGCCTAG GCAACATAGA CCGCCCCCCA TCCCTATAAA                 | 6480 |
| TATTTAACAA TTAGCTGAGC ATAATGGTGT GTGTGCTTGT AGTCTTAGCT GCTGAGGAGG                 | 6540 |
| CTGAGGTGAG AGGATCACTT CAGCTCAAGA GCTTGAGGTT ACAGTGAGCT ATATGATTGC                 | 6600 |
| ACCAGTGAAC TCCAGCCTGG GCAACACAGT GAGACCCTGT CTCAAAACAA AAACAAAAAC                 | 6660 |
| AAAAACAGGT AGGGAGAGAC AAGGAGAAGG GTAGTACTGA CATGGCCTGT CTTTACTTTC                 | 6720 |
| CCCTCTCAGC CCTGGAACTC TCCACAGGGA AAGGTTTTTT GTTCCTTCTT CTTGTCTAAT                 | 6780 |
| AAATGGCTTG ACTTGAGGGG TATCTTGGAG GCATTCTCAA CCCAACCCTG AAGGTTTATC                 | 6840 |
| AGCACTTTCC TGGTGGACAG CACCTCAGCC TCTGCCCTGG CTCCTTTCAT CCTCATCCCC                 | 6900 |
| TAGAGCCAGG ATCGGGAAGC TGGAGTGGTG GCCTGTTTGG ATTCAGGCCC AGGGGCCGAG                 | 6960 |
| ACATTCCCTT CTTCACTCTT TTCCGGATCC                                                 | 6990 |